United States Patent
Yuan et al.

(10) Patent No.: US 12,215,133 B2
(45) Date of Patent: Feb. 4, 2025

(54) GIP AND GLP-1 DUAL RECEPTOR AGONIST, PHARMACEUTICAL COMPOSITION, AND USE

(71) Applicants: BrightGene Bio-Medical Technology Co., Ltd., Jiangsu (CN); BRIGHTGENE PHARMACEUTICAL (SUZHOU) CO. LTD., Jiangsu (CN)

(72) Inventors: Jiandong Yuan, Jiangsu (CN); Yunsong Song, Jiangsu (CN); Wenteng Zhen, Jiangsu (CN); Yue Cai, Jiangsu (CN); Jianing Gu, Jiangsu (CN); Yangqing Huang, Jiangsu (CN)

(73) Assignees: BrightGene Bio-Medical Technology Co., Ltd., Suzhou (CN); BRIGHTGENE PHARMACEUTICAL (SUZHOU) CO. LTD., Suzhou (CN)

( * ) Notice: Subject to any disclaimer, the term of this patent is extended or adjusted under 35 U.S.C. 154(b) by 0 days.

(21) Appl. No.: 18/540,219

(22) Filed: Dec. 14, 2023

(65) Prior Publication Data

US 2024/0150425 A1   May 9, 2024

Related U.S. Application Data

(63) Continuation of application No. 18/283,164, filed as application No. PCT/CN2022/082552 on Mar. 23, 2022.

(30) Foreign Application Priority Data

Mar. 25, 2021 (CN) .......... 202110321851.6
May 20, 2021 (CN) .......... 202110553745.0

(51) Int. Cl.
  *C07K 14/605* (2006.01)
  *A61K 38/00* (2006.01)
  *A61P 3/10* (2006.01)

(52) U.S. Cl.
  CPC .......... *C07K 14/605* (2013.01); *A61P 3/10* (2018.01); *A61K 38/00* (2013.01)

(58) Field of Classification Search
  CPC .......... C07K 14/605; A61P 3/10; A61K 38/00
  See application file for complete search history.

(56) References Cited

U.S. PATENT DOCUMENTS

| | | |
|---|---|---|
| 2014/0162945 A1 | 6/2014 | Ma et al. |
| 2014/0206608 A1 | 7/2014 | Haack et al. |
| 2014/0213513 A1 | 7/2014 | Haack et al. |
| 2016/0199438 A1* | 7/2016 | Bokvist ............... A61K 38/16 530/324 |
| 2016/0199468 A1 | 7/2016 | Xu |
| 2017/0216406 A1 | 8/2017 | Haack et al. |
| 2020/0101162 A1 | 4/2020 | Yuan et al. |
| 2022/0168396 A1* | 6/2022 | Wu .......................... A61P 3/04 |

FOREIGN PATENT DOCUMENTS

| | | |
|---|---|---|
| CN | 103764673 A | 4/2014 |
| CN | 104870009 A | 8/2015 |
| CN | 104945499 A | 9/2015 |
| CN | 106554403 A | 4/2017 |
| CN | 106554404 A | 4/2017 |
| CN | 107207576 A | 9/2017 |
| WO | WO-2006/097538 A1 | 9/2006 |
| WO | WO-2015/149627 A1 | 10/2015 |
| WO | WO-2016/111971 A1 | 7/2016 |
| WO | WO-2020/023386 A1 | 1/2020 |
| WO | WO-2020/159949 A1 | 8/2020 |
| WO | WO-2020/207477 A1 | 10/2020 |

OTHER PUBLICATIONS

Lau et al., J. Med. Chem. 2015, 58, 7370-7380 (Year: 2015).*
Coskun et al., "LY3298176, a novel dual GIP and GLP-1 receptor agonist for the treatment of type 2 diabetes mellitus: From discovery to clinical proof of concept," Molecular Metabolism, Oct. 3, 2018, 18:3-14.

* cited by examiner

*Primary Examiner* — Melissa L Fisher
*Assistant Examiner* — Joseph Fischer
(74) *Attorney, Agent, or Firm* — Foley & Lardner LLP

(57) ABSTRACT

A GIP and GLP-1 dual receptor agonist, a pharmaceutical composition, and the use. In particular, the present application relates to a compound represented by formula I, a pharmaceutical composition comprising the compound, and the use of the compound as a GIP and GLP-1 dual receptor agonist in the field of medicine. The compound represented by formula I exhibits excellent GIPR and GLP-1R agonist activity and excellent pharmaceutical activity in reducing blood sugar and controlling body weight, is a therapeutic drug having a clinical application prospect, and can be used for preventing and treating diseases such as diabetes, diabetes complications, obesity, or obesity complications.

8 Claims, 19 Drawing Sheets

Specification includes a Sequence Listing.

SEQUENCE LISTING

```
Sequence total quantity: 18
SEQ ID NO: 1             moltype = AA  length = 39
FEATURE                  Location/Qualifiers
REGION                   1..39
                         note = polypeptide sequence
SITE                     2
                         note = 2-Aminoisobutyric acid
SITE                     13
                         note = 2-Aminoisobutyric acid
source                   1..39
                         mol_type = protein
                         organism = synthetic construct
SEQUENCE: 1
YXEGTFTSDY SIXLDKIAQK AFVQWLIAGG PSSGAPPPS                             39

SEQ ID NO: 2             moltype = AA  length = 40
FEATURE                  Location/Qualifiers
```

```
SITE                     2
                         note = 2-Aminoisobutyric acid
SITE                     13
                         note = 2-Aminoisobutyric acid
VARIANT                  40
                         note = (R1)-amide modified Lysine residue, wherein R1 may
                         be seleted from (1,20-Eicosanedioic Acid)-amide,
                         (1,18-Octadecanedioic Acid)-amide, (1,20-Eicosanedioic
                         Acid-gammaGlu-2-[2-[2-[2-(Fmoc-amino)ethoxy]ethoxy]a
                         cetic acid- 2-[2-[2-[2-(Fmoc-amino)ethoxy]
                         ethoxy]ethoxy]acetic acid)-amide, [1,20-Eicosanedioic
                         Acid-(3-Sulfamoylpropionic
                         Acid)-2-[2-[2-[2-(Fmoc-amino)ethoxy]ethoxy]ethoxy]acetic
                         acid-2-[2-[2-[2-(Fmoc-amino)ethoxy]ethoxy]ethoxy]acetic
                         acid]-amide, [1,18-Octadecanedioic Acid-gammaGlu-(NH-4x
                         Polyethylene glycol-PA)]-amide, [1,18-Octadecanedioic
                         Acid-gammaGlu-(NH-8x Polyethylene glycol-PA)]-amide,
                         (1,18-Octadecanedioic
                         Acid-gammaGlu-Aminoethylethanolamine-Aminoethylethanolamine
                         )-amide, [1,18-Octadecanedioic Acid-(4-Sulfamoylbutyric
                         Acid)-Aminoethylethanolamine-Aminoethylethanolamine]-amide,
                         [1,18-Octadecanedioic Acid-(6-sulfamoylhexanoic
                         Acid)-Aminoethylethanolamine-Aminoethylethanolamine]-amide,
                         (1,18-Octadecanedioic Acid-[4-(((2-carboxy
                         note = CONT. FROM ABOVE: ethyl)amino)methyl)benzoic
                         acid]-Aminoethylethanolamine-Aminoethylethanolamine)-amide,
                         (1,18-Octadecanedioic
                         Acid-(gammaGlu-Asp)-Aminoethylethanolamine-Aminoethylethano
                         lamine)-amide, [Asp-(1,18-Octadecanedioic
                         Acid)-gammaGlu-Aminoethylethanolamine-Aminoethylethanolamin
                         e]-amide, (1,20-Eicosanedioic
                         Acid-gammaGlu-gammaGlu-Aminoethylethanolamine-
                         Aminoethylethanolamine)-amide,or 1,20-Eicosanedioic
                         Acid-gammaGlu-Aminoethylethanolamine-
                         Aminoethylethanolamine
source                   1..40
                         mol_type = protein
                         organism = synthetic construct
SEQUENCE: 2
YXEGTFTSDY SIXLDKIAQK AFVQWLIAGG PSSGAPPPSK                                      40

SEQ ID NO: 3             moltype = AA  length = 40
FEATURE                  Location/Qualifiers
SITE                     2
                         note = 2-Aminoisobutyric acid
SITE                     13
                         note = 2-Aminoisobutyric acid
SITE                     40
                         note = (1,20-Eicosanedioic Acid)-amide modified residue
source                   1..40
                         mol_type = protein
                         organism = synthetic construct
SEQUENCE: 3
YXEGTFTSDY SIXLDKIAQK AFVQWLIAGG PSSGAPPPSK                                      40

SEQ ID NO: 4             moltype = AA  length = 40
FEATURE                  Location/Qualifiers
SITE                     2
                         note = 2-Aminoisobutyric acid
SITE                     13
                         note = 2-Aminoisobutyric acid
SITE                     40
                         note = (1,18-Octadecanedioic Acid)-amide modified residue
source                   1..40
                         mol_type = protein
                         organism = synthetic construct
SEQUENCE: 4
YXEGTFTSDY SIXLDKIAQK AFVQWLIAGG PSSGAPPPSK                                      40

SEQ ID NO: 5             moltype = AA  length = 40
FEATURE                  Location/Qualifiers
SITE                     2
                         note = 2-Aminoisobutyric acid
SITE                     13
                         note = 2-Aminoisobutyric acid
SITE                     40
                         note = (1,20-Eicosanedioic
                         Acid-gammaGlu-2-[2-[2-[2-(Fmoc-amino)ethoxy]ethoxy]ethoxy]a
                         cetic
```

```
                              acid-2-[2-[2-[2-(Fmoc-amino)ethoxy]ethoxy]ethoxy]acetic
                              acid)-amide modified residue
source                        1..40
                              mol_type = protein
                              organism = synthetic construct
SEQUENCE: 5
YXEGTFTSDY SIXLDKIAQK AFVQWLIAGG PSSGAPPPSK                              40

SEQ ID NO: 6                  moltype = AA   length = 40
FEATURE                       Location/Qualifiers
SITE                          2
                              note = 2-Aminoisobutyric acid
SITE                          13
                              note = 2-Aminoisobutyric acid
SITE                          40
                              note = [1,20-Eicosanedioic Acid-(3-Sulfamoylpropionic
                              Acid)-2-[2-[2-[2-(Fmoc-amino)ethoxy]ethoxy]ethoxy]acetic
                              acid-2-[2-[2-[2-(Fmoc-amino)ethoxy]ethoxy]ethoxy]acetic
                              acid]-amide modified residue
source                        1..40
                              mol_type = protein
                              organism = synthetic construct
SEQUENCE: 6
YXEGTFTSDY SIXLDKIAQK AFVQWLIAGG PSSGAPPPSK                              40

SEQ ID NO: 7                  moltype = AA   length = 40
FEATURE                       Location/Qualifiers
SITE                          2
                              note = 2-Aminoisobutyric acid
SITE                          13
                              note = 2-Aminoisobutyric acid
SITE                          40
                              note = [1,18-Octadecanedioic Acid-gammaGlu-(NH-4x
                              polyethylene glycol- PA)]-amide modified residue
source                        1..40
                              mol_type = protein
                              organism = synthetic construct
SEQUENCE: 7
YXEGTFTSDY SIXLDKIAQK AFVQWLIAGG PSSGAPPPSK                              40

SEQ ID NO: 8                  moltype = AA   length = 40
FEATURE                       Location/Qualifiers
SITE                          2
                              note = 2-Aminoisobutyric acid
SITE                          13
                              note = 2-Aminoisobutyric acid
SITE                          40
                              note = [1,18-Octadecanedioic Acid-gammaGlu-(NH-8x
                              Polyethylene glycol- PA)]-amide modified residue
source                        1..40
                              mol_type = protein
                              organism = synthetic construct
SEQUENCE: 8
YXEGTFTSDY SIXLDKIAQK AFVQWLIAGG PSSGAPPPSK                              40

SEQ ID NO: 9                  moltype = AA   length = 40
FEATURE                       Location/Qualifiers
SITE                          2
                              note = 2-Aminoisobutyric acid
SITE                          13
                              note = 2-Aminoisobutyric acid
SITE                          40
                              note = (1,18-Octadecanedioic
                              Acid-gammaGlu-Aminoethylethanolamine-Amino
                              ethylethanolamine)-amide modified residue
source                        1..40
                              mol_type = protein
                              organism = synthetic construct
SEQUENCE: 9
YXEGTFTSDY SIXLDKIAQK AFVQWLIAGG PSSGAPPPSK                              40

SEQ ID NO: 10                 moltype = AA   length = 40
FEATURE                       Location/Qualifiers
SITE                          2
                              note = 2-Aminoisobutyric acid
SITE                          13
                              note = 2-Aminoisobutyric acid
SITE                          40
                              note = [1,18-Octadecanedioic Acid-(4-Sulfamoylbutyric
```

```
                            Acid)-Aminoethyl
                            ethanolamine-Aminoethylethanolamine]-amide modified residue
source                      1..40
                            mol_type = protein
                            organism = synthetic construct
SEQUENCE: 10
YXEGTFTSDY SIXLDKIAQK AFVQWLIAGG PSSGAPPPSK                                          40

SEQ ID NO: 11               moltype = AA  length = 40
FEATURE                     Location/Qualifiers
SITE                        2
                            note = 2-Aminoisobutyric acid
SITE                        13
                            note = 2-Aminoisobutyric acid
SITE                        40
                            note = [1,18-Octadecanedioic Acid-(6-sulfamoylhexanoic
                            Acid)-Aminoethyl
                            ethanolamine-Aminoethylethanolamine]-amide modified residue
source                      1..40
                            mol_type = protein
                            organism = synthetic construct
SEQUENCE: 11
YXEGTFTSDY SIXLDKIAQK AFVQWLIAGG PSSGAPPPSK                                          40

SEQ ID NO: 12               moltype = AA  length = 40
FEATURE                     Location/Qualifiers
SITE                        2
                            note = 2-Aminoisobutyric acid
SITE                        13
                            note = 2-Aminoisobutyric acid
SITE                        40
                            note = (1,18-Octadecanedioic
                            Acid-[4-(((2-carboxyethyl)amino)methyl) benzoic
                            acid]-Aminoethylethanolamine-Aminoethylethanolamine)-
                            amide modified residue
source                      1..40
                            mol_type = protein
                            organism = synthetic construct
SEQUENCE: 12
YXEGTFTSDY SIXLDKIAQK AFVQWLIAGG PSSGAPPPSK                                          40

SEQ ID NO: 13               moltype = AA  length = 40
FEATURE                     Location/Qualifiers
SITE                        2
                            note = 2-Aminoisobutyric acid
SITE                        13
                            note = 2-Aminoisobutyric acid
SITE                        40
                            note = (1,18-Octadecanedioic
                            Acid-(gammaGlu-Asp)-Aminoethylethanol
                            amine-Aminoethylethanolamine)-amide modified residue
source                      1..40
                            mol_type = protein
                            organism = synthetic construct
SEQUENCE: 13
YXEGTFTSDY SIXLDKIAQK AFVQWLIAGG PSSGAPPPSK                                          40

SEQ ID NO: 14               moltype = AA  length = 40
FEATURE                     Location/Qualifiers
SITE                        2
                            note = 2-Aminoisobutyric acid
SITE                        13
                            note = 2-Aminoisobutyric acid
SITE                        40
                            note = [Asp-(1,18-Octadecanedioic
                            Acid)-gammaGlu-Aminoethylethanol
                            amine-Aminoethylethanolamine]-amide modified residue
source                      1..40
                            mol_type = protein
                            organism = synthetic construct
SEQUENCE: 14
YXEGTFTSDY SIXLDKIAQK AFVQWLIAGG PSSGAPPPSK                                          40

SEQ ID NO: 15               moltype = AA  length = 40
FEATURE                     Location/Qualifiers
SITE                        2
                            note = 2-Aminoisobutyric acid
SITE                        13
                            note = 2-Aminoisobutyric acid
```

```
SITE                    40
                        note = (1,20-Eicosanedioic
                         Acid-gammaGlu-Aminoethylethanolamine-Amino
                         ethylethanolamine)-amide modified residue
source                  1..40
                        mol_type = protein
                        organism = synthetic construct
SEQUENCE: 15
YXEGTFTSDY SIXLDKIAQK AFVQWLIAGG PSSGAPPPSK                              40

SEQ ID NO: 16           moltype = AA  length = 40
FEATURE                 Location/Qualifiers
SITE                    2
                        note = 2-Aminoisobutyric acid
SITE                    13
                        note = 2-Aminoisobutyric acid
SITE                    40
                        note = (1,20-Eicosanedioic
                         Acid-gammaGlu-gammaGlu-Aminoethylethanol
                         amine-Aminoethylethanolamine)-amide modified residue
source                  1..40
                        mol_type = protein
                        organism = synthetic construct
SEQUENCE: 16
YXEGTFTSDY SIXLDKIAQK AFVQWLIAGG PSSGAPPPSK                              40

SEQ ID NO: 17           moltype = AA  length = 40
FEATURE                 Location/Qualifiers
SITE                    2
                        note = 2-Aminoisobutyric acid
SITE                    13
                        note = 2-Aminoisobutyric acid
SITE                    40
                        note = (1,20-Eicosanedioic
                         Acid-gammaGlu-2-[2-[2-[2-(Fmoc-amino)ethoxy]ethoxy]ethoxy]a
                         cetic
                         acid-2-[2-[2-[2-(Fmoc-amino)ethoxy]ethoxy]ethoxy]acetic
                         acid)-amide modified residue
source                  1..40
                        mol_type = protein
                        organism = synthetic construct
SEQUENCE: 17
YXEGTFTSDY SIXLDKIAQK AFVQWLIAGG PSSGAPPPSK                              40

SEQ ID NO: 18           moltype = AA  length = 39
FEATURE                 Location/Qualifiers
SITE                    2
                        note = 2-Aminoisobutyric acid
SITE                    13
                        note = 2-Aminoisobutyric acid
SITE                    16
                        note = (1,20-Eicosanedioic
                         Acid-gammaGlu-2-[2-[2-[2-(Fmoc-amino)ethoxy]ethoxy]ethoxy]a
                         cetic
                         acid-2-[2-[2-[2-(Fmoc-amino)ethoxy]ethoxy]ethoxy]acetic
                         acid) modified residue
SITE                    39
                        note = Amidated residue
source                  1..39
                        mol_type = protein
                        organism = synthetic construct
SEQUENCE: 18
YXEGTFTSDY SIXLDKIAQK AFVQWLIAGG PSSGAPPPS                               39
```

GIP AND GLP-1 DUAL RECEPTOR AGONIST, PHARMACEUTICAL COMPOSITION, AND USE

CROSS-REFERENCE TO RELATED APPLICATIONS

The present disclosure is a Continuation of U.S. application Ser. No. 18/283,164, which is the U.S. National Stage of PCT/CN2022/082552, filed Mar. 23, 2022, which claims the right of priority for the following patent applications: a Chinese patent application of the application number 202110321851.6, filed with the State Intellectual Property Office of China on 25 Mar. 2021 and a Chinese patent application of the application number 202110553745.0, filed with the State Intellectual Property Office of China on 20 May 2021; and the entire contents of the above-mentioned patent applications are incorporated in the present disclosure by reference.

The instant application contains a Sequence Listing which has been submitted in XML format via Patent Center and is hereby incorporated by reference in its entirety. Said XML copy, created on Oct. 17, 2024, is named 125310-0104_SL.xml and is 40,998 bytes.

The present disclosure claims the right of priority for the following patent applications: a Chinese patent application of the application number 202110321851.6, filed with the State Intellectual Property Office of China on 25 Mar. 2021 and a Chinese patent application of the application number 202110553745.0, filed with the State Intellectual Property Office of China on 20 May 2021; and the entire contents of the above-mentioned patent applications are incorporated in the present disclosure by reference.

TECHNICAL FIELD

The present disclosure belongs to the technical field of medicine, and specifically, the present disclosure relates to a polypeptide represented by formula I, a GIP and GLP-1 dual receptor agonist, a pharmaceutical composition and the use thereof in preventing and/or treating diseases associated with metabolic disorders.

BACKGROUND ART

Obesity and diabetes are growing global health problems and are associated with a variety of other diseases, including cardiovascular diseases (CVDs), obstructive primary sleep apnea, stroke, peripheral arterial diseases, microvascular complications, osteoarthritis, etc. Therefore, developing a new therapy and a therapeutic drug for obesity, diabetes and complications thereof is of great significance for improving human health.

Glucose-dependent insulinotropic peptide (GIP) is a gastrointestinal regulatory peptide having 42 amino acids and plays a physiological role in glucose homeostasis by stimulating insulin secretion from pancreatic R cells in the presence of glucose and protecting pancreatic R cells. Glucagon-like peptide-1 (GLP-1) is a peptide having 37 amino acids and stimulates insulin secretion, protects pancreatic p cells, and inhibits glucagon secretion, gastric emptying, and food intake, thereby leading to body weight loss. GIP and GLP-1 are secreted by K cells and L cells of the small intestinal endothelium, respectively, and are referred to as incretins, and incretin receptor signaling plays a key physiologically relevant role in glucose homeostasis.

GIP and GLP-1 produce corresponding physiological effects by binding to specific receptors thereof, and bind to GIP (GIPR) receptor and GLP-1 receptor (GLP-1R), respectively. The two receptors belong to the G protein-coupled receptor family. In normal physiology, GIP and GLP-1 are secreted from the gut after a meal, and the incretins enhance physiological responses to food, including inducing satiety, promoting insulin secretion, protecting pancreas R cells and nutrient disposition. It has been found that a patient with type 2 diabetics has an impaired incretin response.

Despite GIP and GLP-1 have a potential antidiabetic activity, it has been found that administration of GLP-1 analog is limited by side effects such as nausea and vomiting, and therefore the most common is that administration may not achieve full glycemic control and body weight loss. GIP alone has very limited glucose-lowering ability in type 2 diabetics. Both native GIP and GLP-1 can be rapidly inactivated by ubiquitous protease DPP IV and therefore may only be used for short-term metabolic control.

Generally, a diabetic patient can develop tolerance to GIP, and even GIP above the physiological level has little hypoglycemic effect. However, GLP-1 is different, and most diabetic patients maintain sensitivity to GLP-1. The relationship between GIP and GLP-1 is similar to that of the other two important hormones insulin and leptin. Diabetic patients are sensitive to insulin, but obese patients are resistant to leptin. Therefore, although field of GLP-1 is booming and GLP-1 has become the most important class of hypoglycemic drugs, the development of GIP is very slow. Studies have shown that if the blood sugar is reduced to a certain level, the sensitivity to GIP can be restored, which indicates that co-activation of GLP-1R/GIPR can exert a synergistic hypoglycemic effect, and GIP and GLP-1 dual receptor agonist can produce more excellent hypoglycemic effect and stimulation of insulin secretion.

The prior art document WO 2016111971 A1 discloses a GIP/GLP dual agonist, LY3298176. LY3298176 mainly has the amino acid sequence of GIP, and the lysine at position 20 is modified by means of GLP-1 drug modification. At present, LY3298176 is in a phase II clinical trial of hypoglycemic and body weight loss efficacy, and the results showed that the efficacy and tolerability are improved when the initial dose is low and the subsequent dose increase is small; and after just 8 weeks of treatment, patients with type 2 diabetes showed significant reductions in A1C and body weight.

It is an important problem to be solved urgently in the art to develop a GIP and GLP-1 dual receptor agonist having a novel structure to provide a safe and effective new treatment method for obesity, diabetes and complications thereof.

SUMMARY OF THE INVENTION

Problems to be Solved by the Invention

In view of the problems existing in the prior art, for example, there are many limitations in the therapeutic application prospect of administering GIP or GLP-1 alone as an antidiabetic drug, the present disclosure provides a compound having a novel structure represented by formula I, which has both GLP-1R agonist activity and GIPR agonist activity. As a GLP-1 and GIP dual receptor agonist, the compound exhibits excellent hypoglycemic effect and has good clinical application prospects.

Solution to Problems

The present disclosure first provides a compound represented by formula I (SEQ ID NO: 2) or a pharmaceutically acceptable salt, ester, solvate, optical isomer, tautomer, isotopically labeled compound or prodrug thereof:

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser-A$_{40}$   I;

wherein, A$_{40}$ is the following structure connecting to Ser via a peptide bond:

A$_{40}$ is

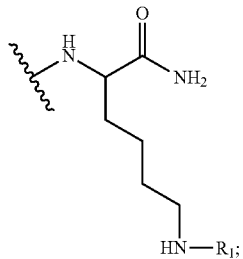

R$_1$ is —(Z$_1$)$_m$—(Z$_2$)$_n$—C(=O)—(CH$_2$)$_o$—C(=O)—Z$_3$;
m is 0 or 1;
if present, Z$_1$ is —C(=O)—(CH$_2$)$_r$—(Z$_4$)$_p$—NH—, wherein p is any integer of 4-8, each Z$_4$ is independently —O-CH$_2$-CH$_2$— or —NH—C(=O)—CH$_2$—, and r is 1 or 2;
n is any integer of 0-2;
if present, each Z$_2$ is independently

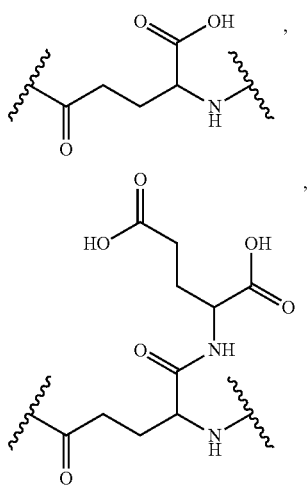

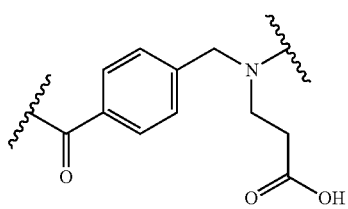

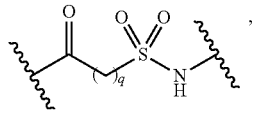

wherein q is any integer of 2-5;
is any integer of 14-18, preferably 18;
and Z$_3$ is hydroxyl or

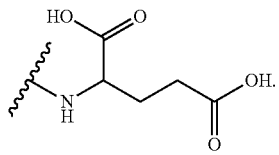 [SMILES: *NC(CCC(=O)O)C(=O)O]

In the present disclosure, the amino acid sequence from position 1-position 39 (Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser) in the compound represented by formula I is shown in SEQ ID NO:1.

In one embodiment, the present disclosure provides the compound or the pharmaceutically acceptable salt, ester, solvate, optical isomer, tautomer, isotopically labeled compound or prodrug thereof of the present disclosure, wherein, R$_1$ is —C(=O)—(CH$_2$)$_o$—C(=O)—Z$_3$;
o is any integer of 14-18, preferably 18;
and Z$_3$ is hydroxyl or

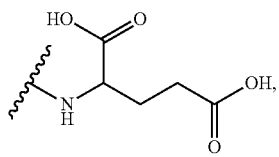 [SMILES: *NC(CCC(=O)O)C(=O)O]

preferably hydroxyl.

In one embodiment, the present disclosure provides the compound or the pharmaceutically acceptable salt, ester, solvate, optical isomer, tautomer, isotopically labeled compound or prodrug thereof of the present disclosure, wherein, R$_1$ is —Z$_1$—Z$_2$—C(=O)—(CH$_2$)$_o$—C(=O)—Z$_3$;
Z$_1$ is —C(=O)—CH$_2$—(Z$_4$)$_7$—NH—, wherein each Z$_4$ is independently —O—CH$_2$—CH$_2$— or —NH—C(=O)—CH$_2$—, preferably —(Z$_4$)$_7$— is —(O—CH$_2$—CH$_2$)$_3$—(NH—C(=O)—CH$_2$)—(O—CH$_2$—CH$_2$)$_3$— or —(O—CH$_2$—CH$_2$)$_7$—;
Z$_2$ is

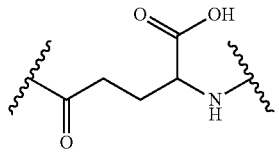

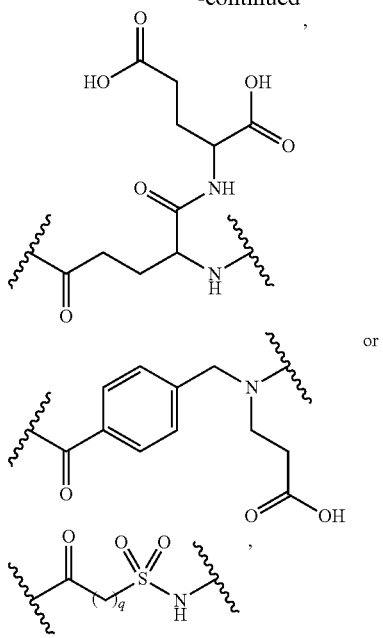

or

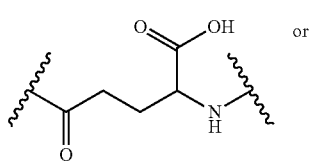

preferably

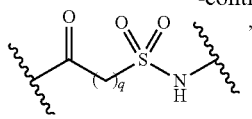

wherein q is any integer of 2-5, preferably 2;
is any integer of 14-18;
and $Z_3$ is hydroxyl or

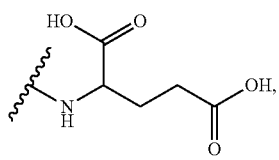

preferably hydroxyl.

In one embodiment, the present disclosure provides the compound or the pharmaceutically acceptable salt, ester, solvate, optical isomer, tautomer, isotopically labeled compound or prodrug thereof according to the present disclosure, wherein, $A_{40}$ is selected from a structure represented by any one of the followings:

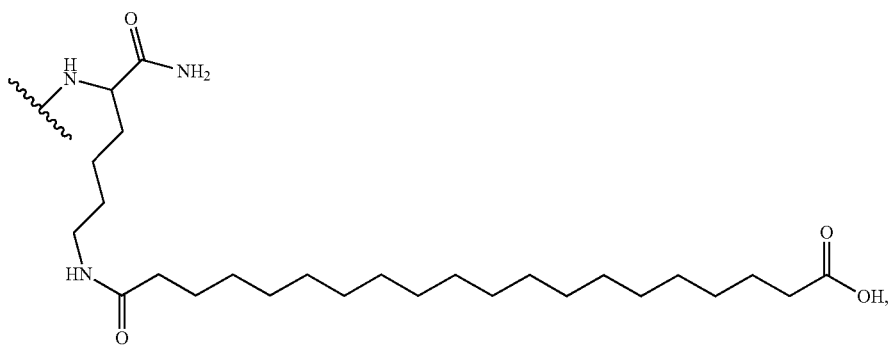

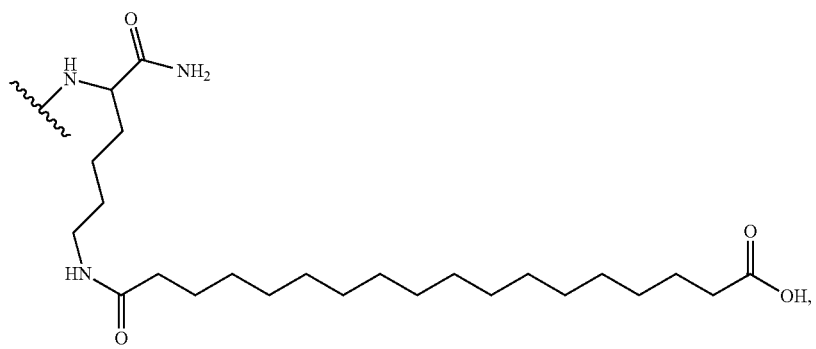

-continued
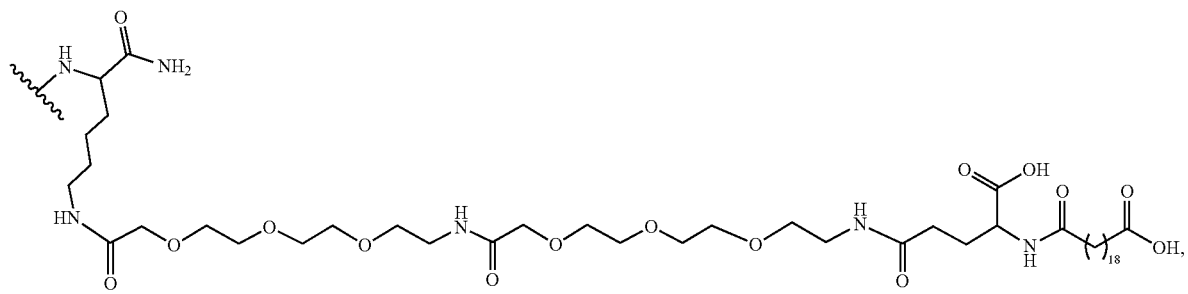
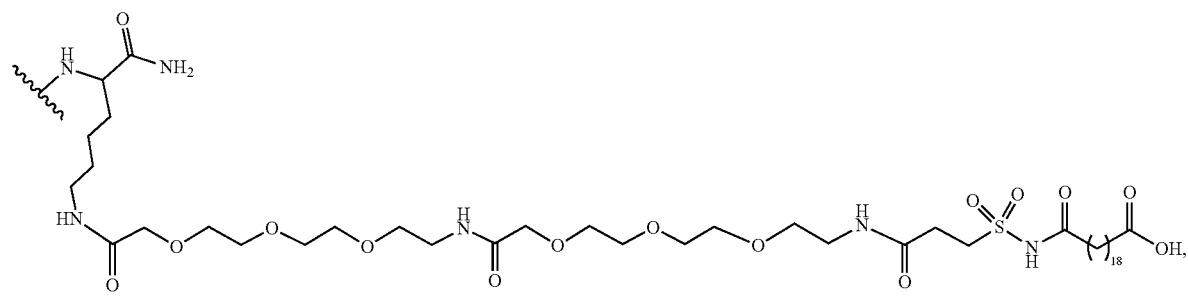
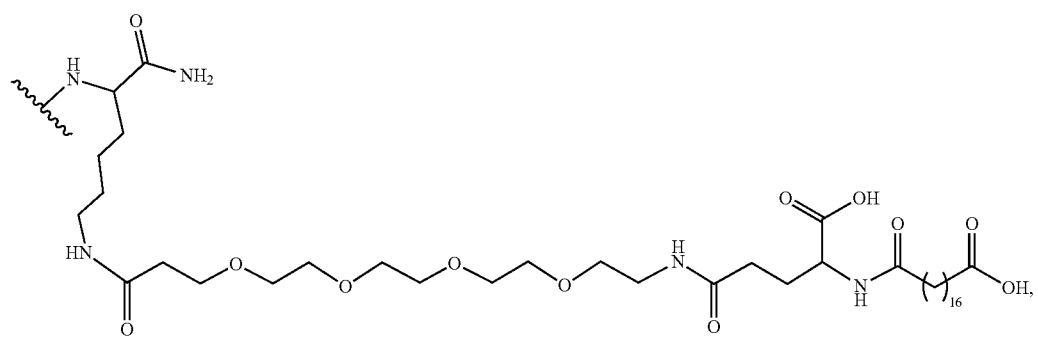
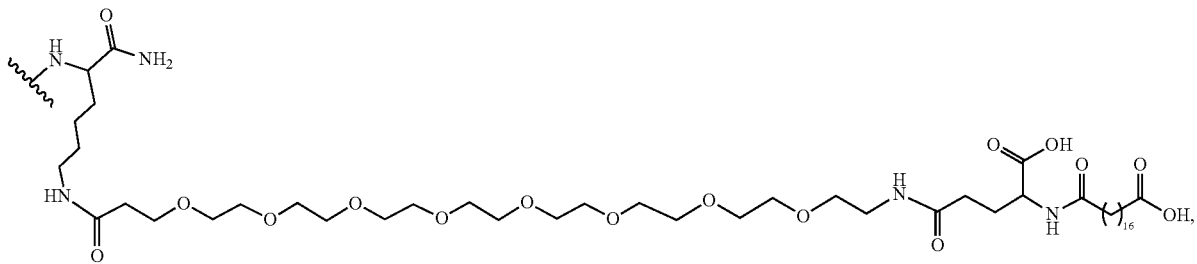
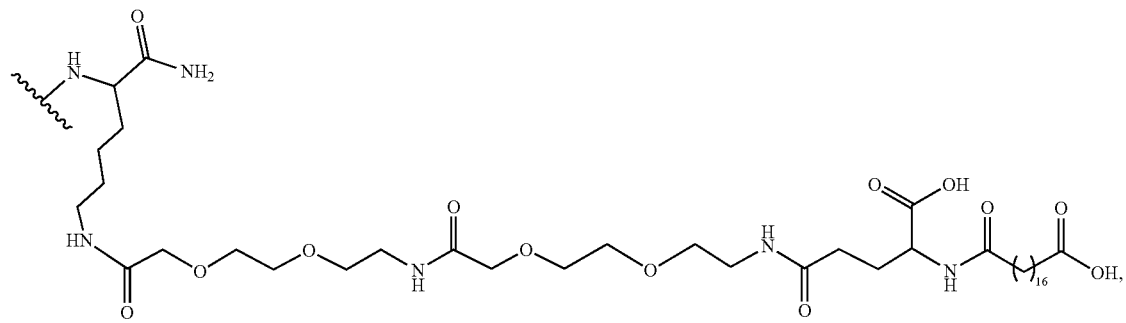

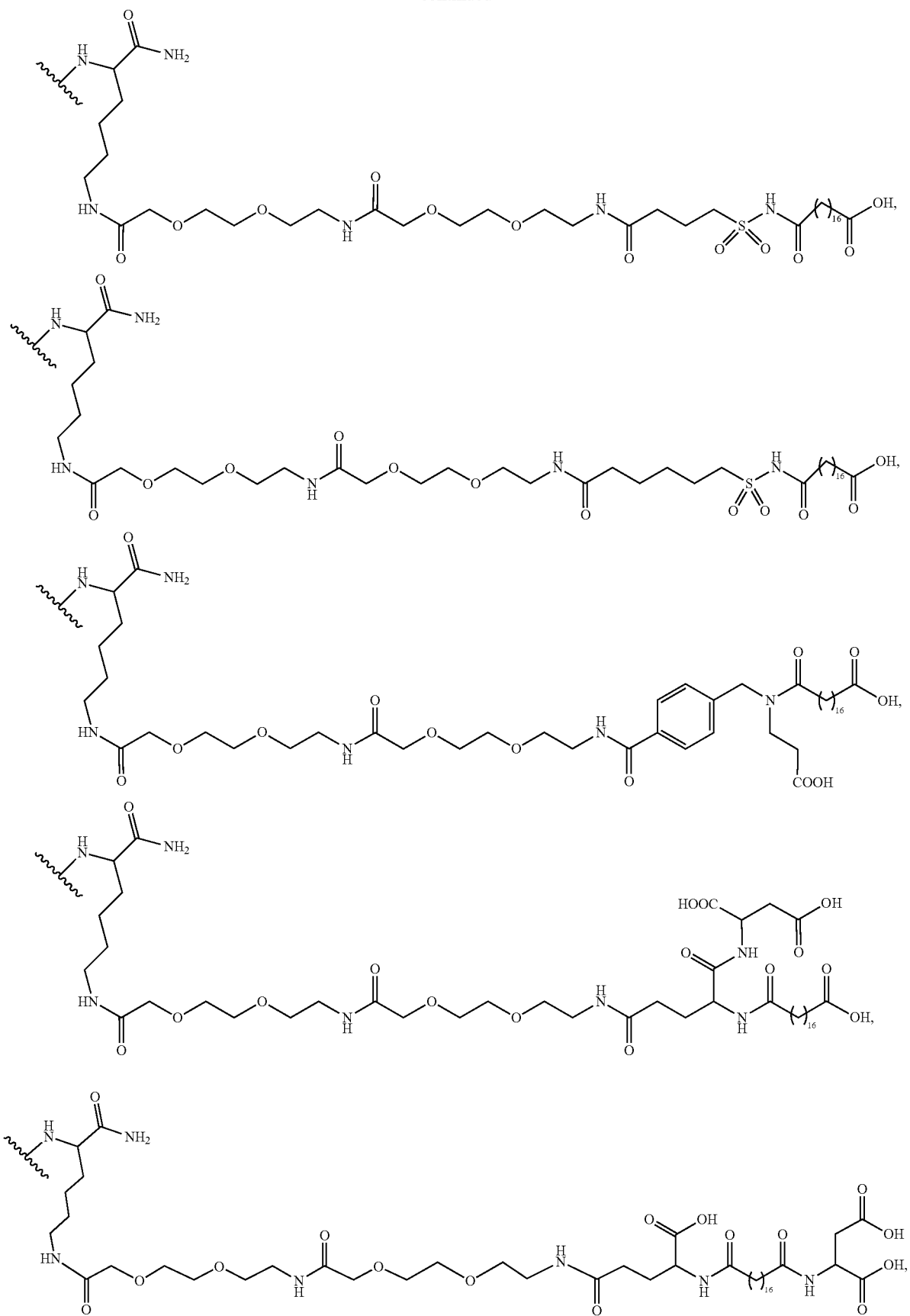

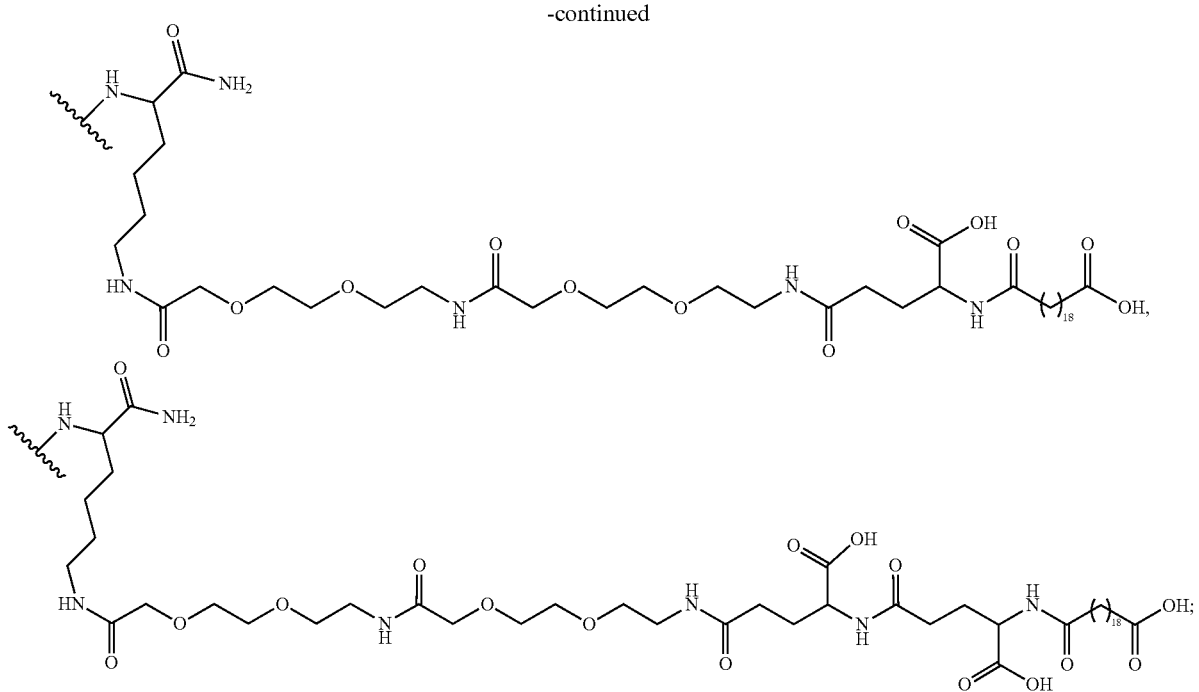
preferably a structure represented by any one of the followings:
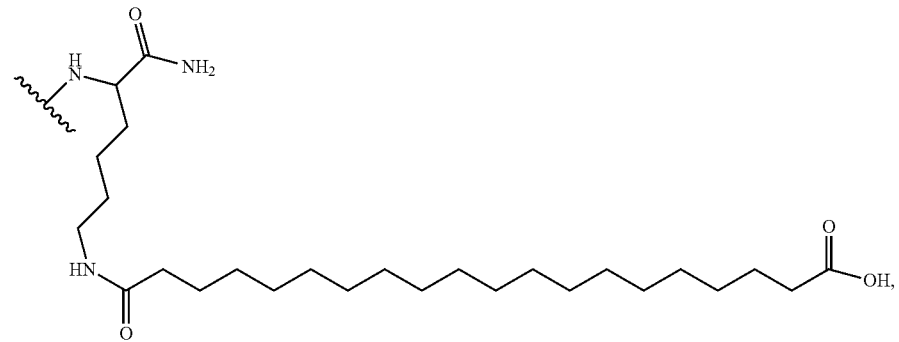
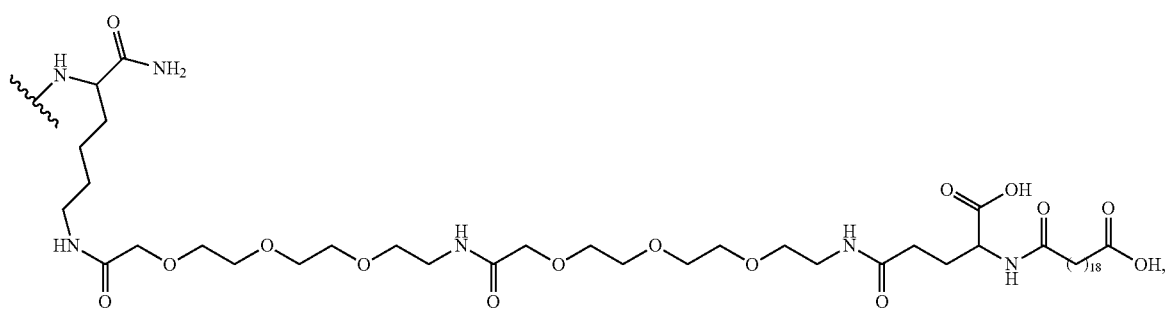

-continued

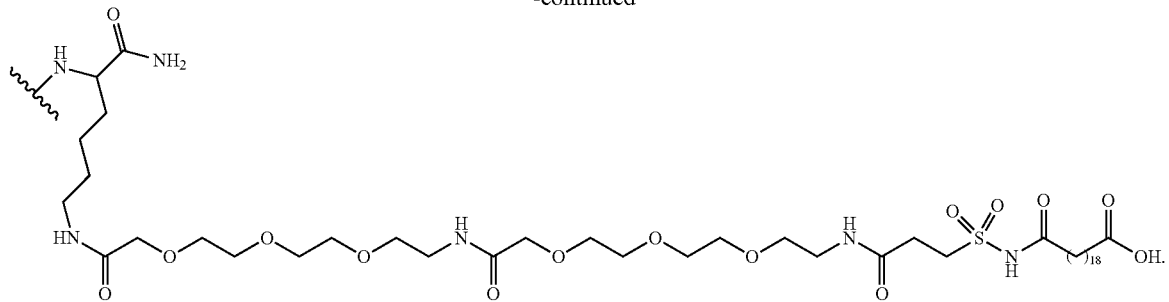

The present disclosure further provides a compound represented by any one of the following formulas I-1-I-14 or a pharmaceutically acceptable salt, ester, solvate, optical isomer, tautomer, isotopically labeled compound or prodrug thereof:

I-1 (SEQ ID NO: 3)

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser

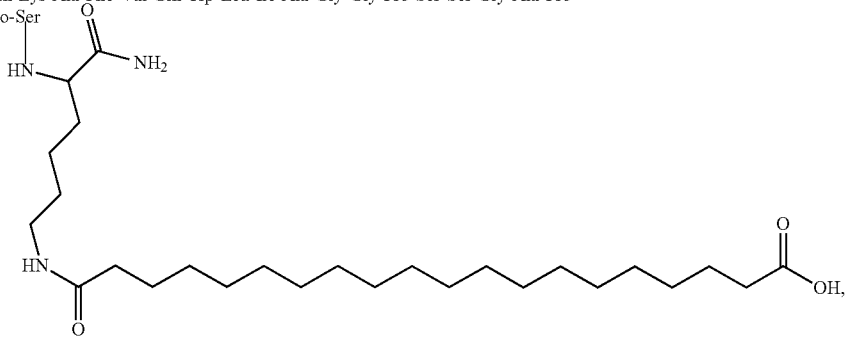

I-2 (SEQ ID NO: 4)

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser

I-3 (SEQ ID NO: 5)

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser

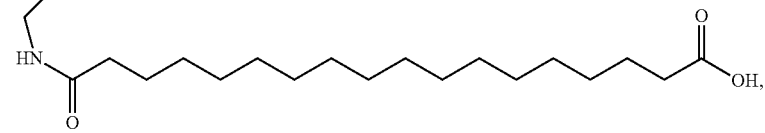

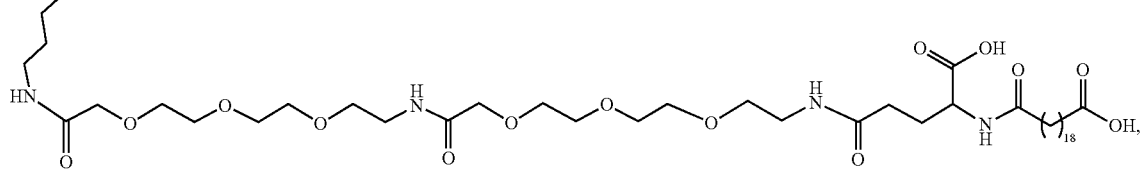

-continued

I-4 (SEQ ID NO: 6)

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser

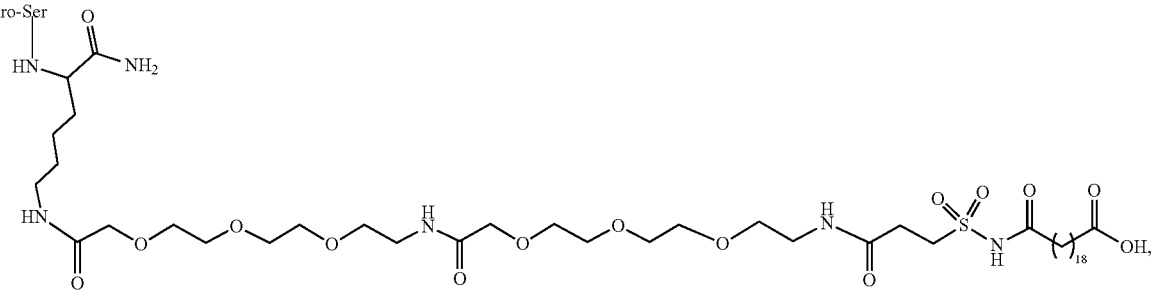

I-5 (SEQ ID NO: 7)

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser

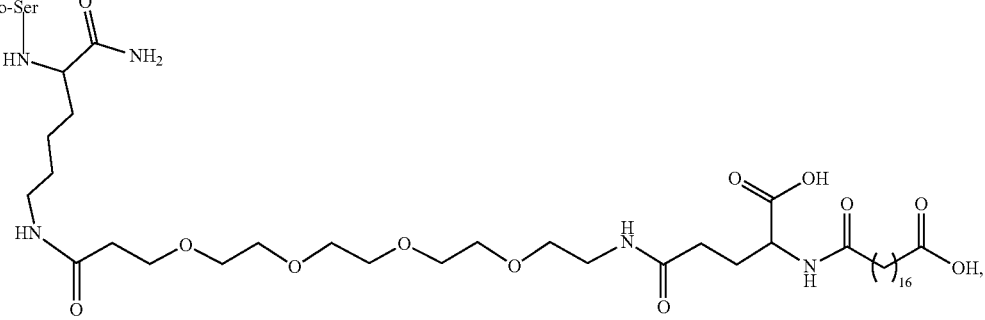

I-6 (SEQ ID NO: 8)

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser

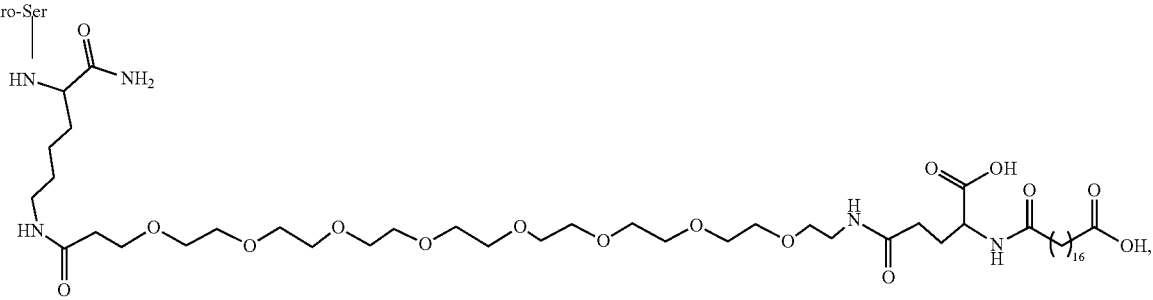

I-7 (SEQ ID NO: 9)

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser

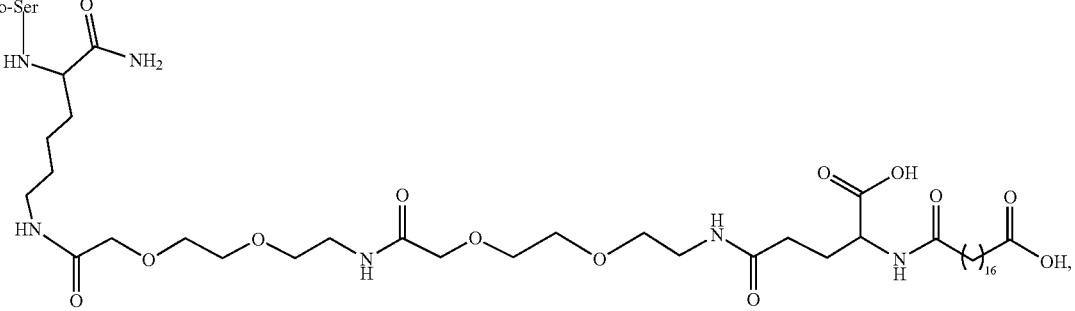

I-8 (SEQ ID NO: 10)

Tyr-Aib-Glu-Gly-Thr-Phe-Thr-Ser-Asp-Tyr-Ser-Ile-Aib-Leu-Asp-Lys-Ile-
Ala-Gln-Lys-Ala-Phe-Val-Gln-Trp-Leu-Ile-Ala-Gly-Gly-Pro-Ser-Ser-Gly-Ala-Pro-
Pro-Pro-Ser

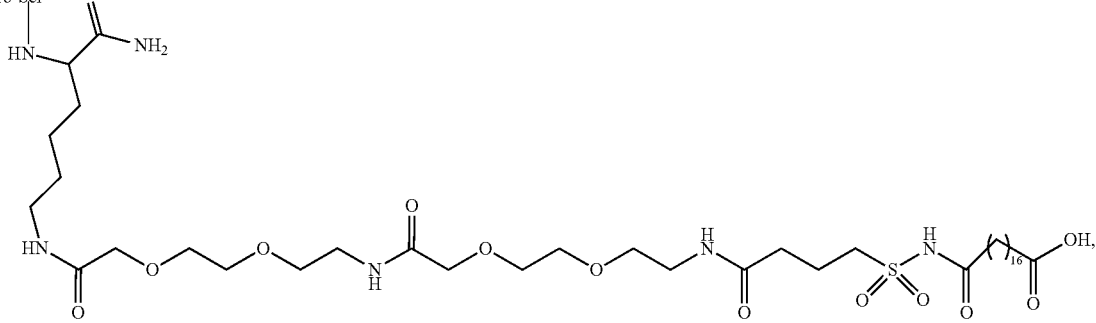

I-9 (SEQ ID NO: 11)

Tyr-Aib-Glu-Gly-Thr-Phe-Thr-Ser-Asp-Tyr-Ser-Ile-Aib-Leu-Asp-Lys-Ile-
Ala-Gln-Lys-Ala-Phe-Val-Gln-Trp-Leu-Ile-Ala-Gly-Gly-Pro-Ser-Ser-Gly-Ala-Pro-
Pro-Pro-Ser

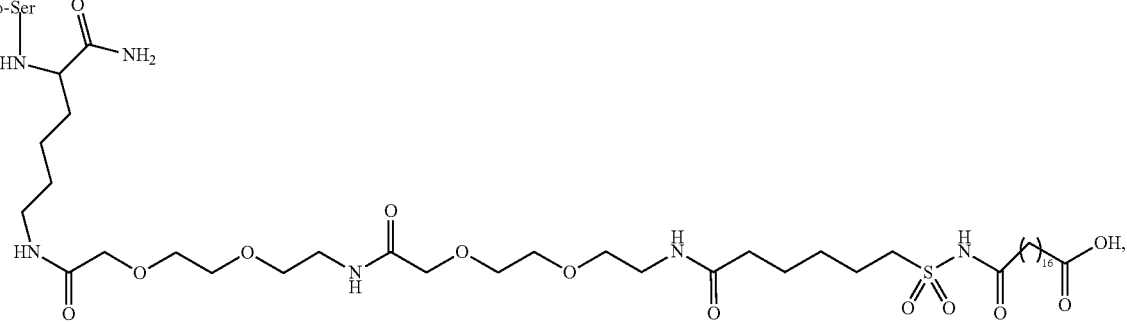

I-10 (SEQ ID NO: 12)

Tyr-Aib-Glu-Gly-Thr-Phe-Thr-Ser-Asp-Tyr-Ser-Ile-Aib-Leu-Asp-Lys-Ile-
Ala-Gln-Lys-Ala-Phe-Val-Gln-Trp-Leu-Ile-Ala-Gly-Gly-Pro-Ser-Ser-Gly-Ala-Pro-
Pro-Pro-Ser

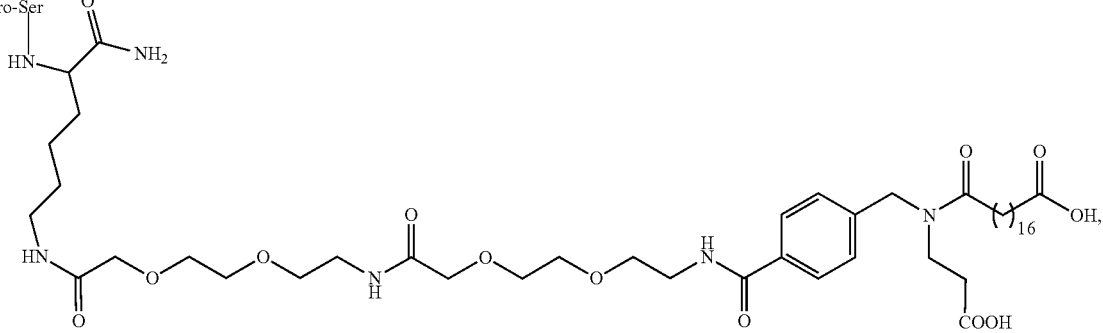

I-11 (SEQ ID NO: 13)

Tyr-Aib-Glu-Gly-Thr-Phe-Thr-Ser-Asp-Tyr-Ser-Ile-Aib-Leu-Asp-Lys-Ile-
Ala-Gln-Lys-Ala-Phe-Val-Gln-Trp-Leu-Ile-Ala-Gly-Gly-Pro-Ser-Ser-Gly-Ala-Pro-
Pro-Pro-Ser

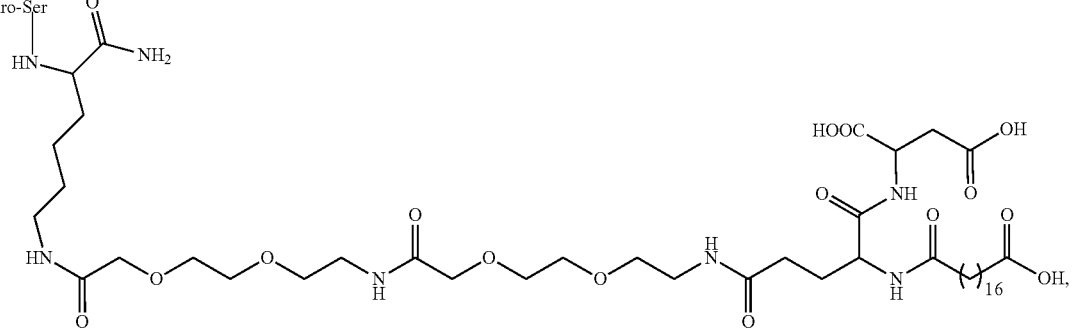

I-12 (SEQ ID NO: 14)

Tyr-Aib-Glu-Gly-Thr-Phe-Thr-Ser-Asp-Tyr-Ser-Ile-Aib-Leu-Asp-Lys-Ile-
Ala-Gln-Lys-Ala-Phe-Val-Gln-Trp-Leu-Ile-Ala-Gly-Gly-Pro-Ser-Ser-Gly-Ala-Pro-
Pro-Pro-Ser

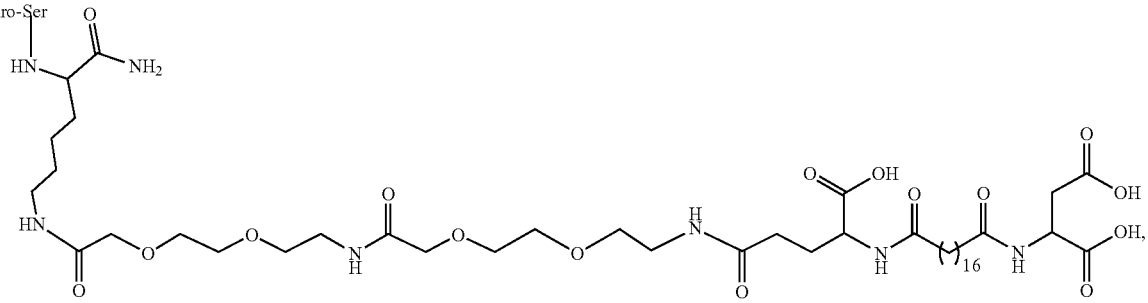

I-13 (SEQ ID NO: 15)

Tyr-Aib-Glu-Gly-Thr-Phe-Thr-Ser-Asp-Tyr-Ser-Ile-Aib-Leu-Asp-Lys-Ile-
Ala-Gln-Lys-Ala-Phe-Val-Gln-Trp-Leu-Ile-Ala-Gly-Gly-Pro-Ser-Ser-Gly-Ala-Pro-
Pro-Pro-Ser

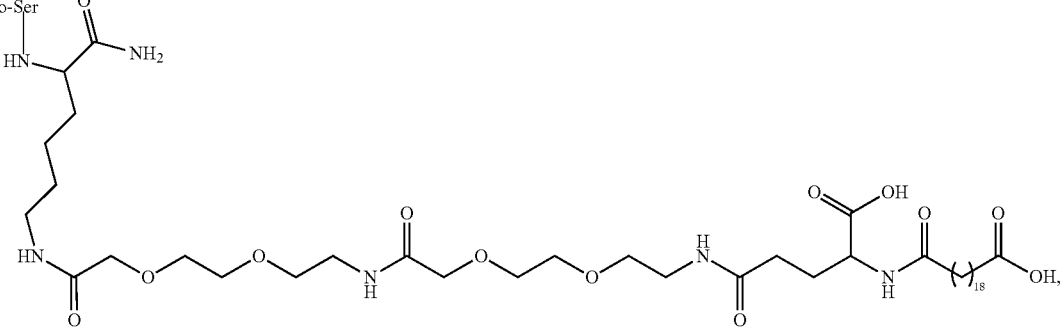

I-14 (SEQ ID NO: 16)

Tyr-Aib-Glu-Gly-Thr-Phe-Thr-Ser-Asp-Tyr-Ser-Ile-Aib-Leu-Asp-Lys-Ile-
Ala-Gln-Lys-Ala-Phe-Val-Gln-Trp-Leu-Ile-Ala-Gly-Gly-Pro-Ser-Ser-Gly-Ala-Pro-
Pro-Pro-Ser

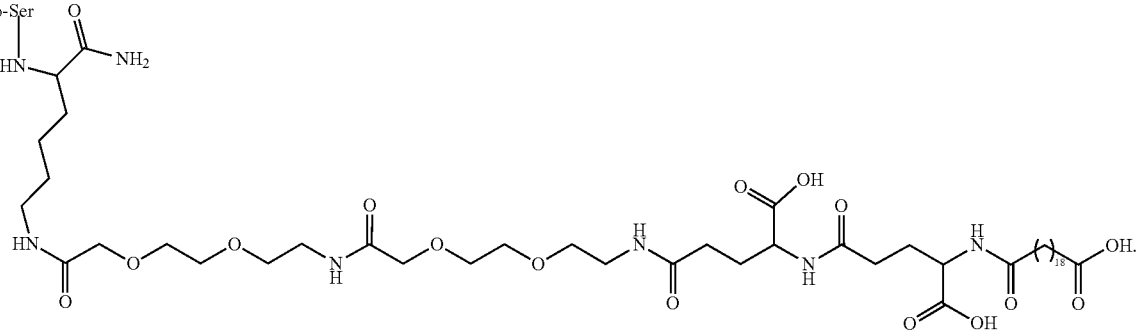

The present disclosure further provides a GIP and GLP-1 dual receptor agonist, wherein the GIP and GLP-1 dual receptor agonist is a compound represented by formula I-3 or a pharmaceutically acceptable salt, ester, solvate, optical isomer, tautomer, isotopically labeled compound or prodrug thereof:

I-3 (SEQ ID NO: 5)

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser

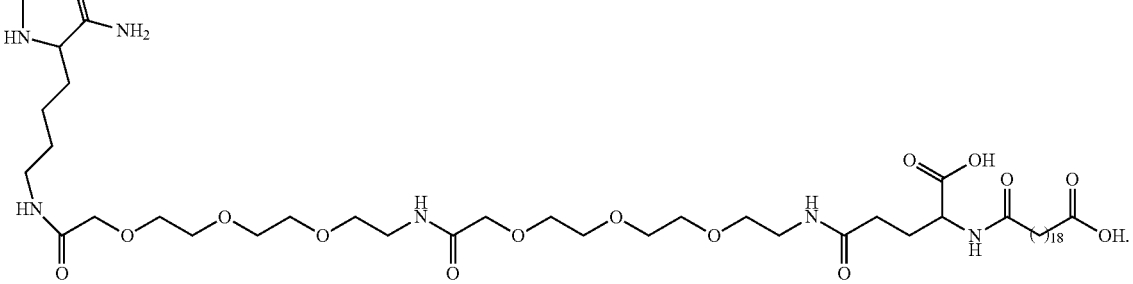

The length and specific structure of the fatty side chain of the peptide in the present disclosure do not affect the effect of lowering blood sugar, but mainly affects the metabolic rate of the compound in the body, that is, the sustained-release time of the drug molecule in the body, that is, affects the total effective time of the efficacy. Namely, compounds I-1, I-2, I-3, I-4, I-5, I-6, I-7, I-8, I-9, I-10, I-11, I-12, I-13 and I-14 have comparable hypoglycemic effects, and the metabolic rates thereof in the body are also similar. The prior art documents WO 2016111971 A1 and WO 2006097537 $A_2$ discloses the effect of the fatty side chain on the metabolism of the active agent of GLP agonist, and the entire contents of the above-mentioned patents are taken as a part of the present disclosure by reference.

The present disclosure further provides a pharmaceutical composition comprising the compound or the pharmaceutically acceptable salt, ester, solvate, optical isomer, tautomer, isotopically labeled compound or prodrug thereof according to the present disclosure, or the GIP and GLP-1 dual receptor agonist according to the present disclosure;
  optionally, the pharmaceutical composition further comprises one or more pharmaceutically acceptable carriers.

The present disclosure further provides the use of the compound or the pharmaceutically acceptable salt, ester, solvate, optical isomer, tautomer, isotopically labeled compound or prodrug thereof according to the present disclosure, the GIP and GLP-1 dual receptor agonist according to the present disclosure, or the pharmaceutical composition according the present disclosure in the preparation of a drug for preventing and/or treating diseases associated with metabolic disorders;
  optionally, the diseases associated with metabolic disorders are diabetes, diabetes complications, obesity, or obesity complications.

In one embodiment, the present disclosure provides the compound or the pharmaceutically acceptable salt, ester, solvate, optical isomer, tautomer, isotopically labeled compound or prodrug thereof according to the present disclosure, the GIP and GLP-1 dual receptor agonist according to the present disclosure, or the pharmaceutical composition according the present disclosure, for preventing and/or treating diseases associated with metabolic disorders;
  optionally, the diseases associated with metabolic disorders are diabetes, diabetes complications, obesity, or obesity complications.

The present disclosure further provides a method for preventing and/or treating diseases associated with metabolic disorders, which comprises administering a prophylactically and/or therapeutically effective amount of the compound or the pharmaceutically acceptable salt, ester, solvate, optical isomer, tautomer, isotopically labeled compound or prodrug thereof according the present disclosure, the GIP and GLP-1 dual receptor agonist according the present disclosure, or the pharmaceutical composition according the present disclosure to a subject;
  optionally, the diseases associated with metabolic disorders are diabetes, diabetes complications, obesity, or obesity complications.

Effects of the Invention

The present disclosure provides a compound having a novel structure represented by formula I, wherein the lysine residue thereof at position 40 is modified with $R_1$ group. It is found in the present disclosure by the experiment that the compound represented by formula I has both GIP and GLP-1 polypeptide activities, and is a GIP and GLP-1 dual receptor agonist. Compared with the compound LY3298176 having the modified lysine residue at position 20, the compound represented by formula I shows equivalent or reduced $EC_{50}$ value.

The side chain connection position has a significant effect on the hypoglycemic effect of the compound. The compound represented by formula I, as a GIP and GLP-1 dual receptor agonist, shows significant hypoglycemic effect and body weight loss effect in the type 2 diabetes model (db/db) mice, provides a therapeutic drug with great clinical application prospects for the prevention and treatment of diseases associated with metabolic disorders, and can be used for preventing and treating diabetes, such as diabetes, diabetes complications, obesity, or obesity complications.

In one embodiment, the present disclosure provides a compound represented by formula I-3. It is found in cell experiments in the present disclosure that compared with the GIP and GLP-1 dual receptor agonist LY3298176, the compound represented by formula I-3 has lower $EC_{50}$ values against both GIPR and GLP-1R and compared the marketed Semaglutide, the compound represented by formula I-3 has significantly lower $EC_{50}$ value against GIPR, which indicates that the compound represented by formula I-3 has a significantly better activation effect on both GIPR and GLP-1R, and the activity of the compound represented by formula I-3 as a GIP and GLP-1 dual receptor agonist is better than that of currently developed compounds. In addition, the compound represented by formula I-3 can effectively reduce the blood sugar content and the glycosylated hemoglobin content of type 2 diabetes model (db/db) mice, control the body weight growth of mice, and also shows a better effect on affecting insulin secretion in mice. Moreover, the compound represented by formula I-3 is more effective than compound LY3298176 in reducing blood sugar and controlling body weight of type 2 diabetes model mice. The compound represented by formula I-3 shows important clinical application prospects in preventing and treating diseases associated with metabolic disorders, such as diabetes, diabetes complications, obesity, or obesity complications.

In one embodiment, the compound represented by formula I-3 (BG128) can cause acute decreases in body weight and food intake of type 2 diabetes model (db/db) mice, which remain relatively stable in the later period of administration. After the first administration, the compound represented by formula I-3 significantly reduces the non-fasting blood glucose and fasting blood glucose of db/db mice, and reduces insulin and glycosylated hemoglobin contents in peripheral blood. Moreover, the effect of the compound represented by formula I-3 on the non-fasting blood glucose, serum insulin, and body weight loss rate of mice is better than that of a positive drug Tirzepatide at an equal dose.

In one embodiment, the compound represented by formula I-3 (BG128) has obvious therapeutic effect on model C57BL/6 mice having STZ-HFD-induced diabetes combined NASH, and each dose group of BG128 can significantly reduce the fasting blood glucose, insulin and peripheral blood HbA1c % of the model mice, and has a certain protective effect on the model mice. In addition, the compound represented by formula I-3 improves liver function and blood lipid-related clinical biochemical indicators, reduces liver NAS score and fibrosis rate, and significantly delays the progress of NASH and fibrosis process. The compound represented by formula I-3 has better effect compared with the positive drug Tirzepatide at an equal dose.

DETAILED DESCRIPTION OF EMBODIMENTS

Definitions

Figure 1:
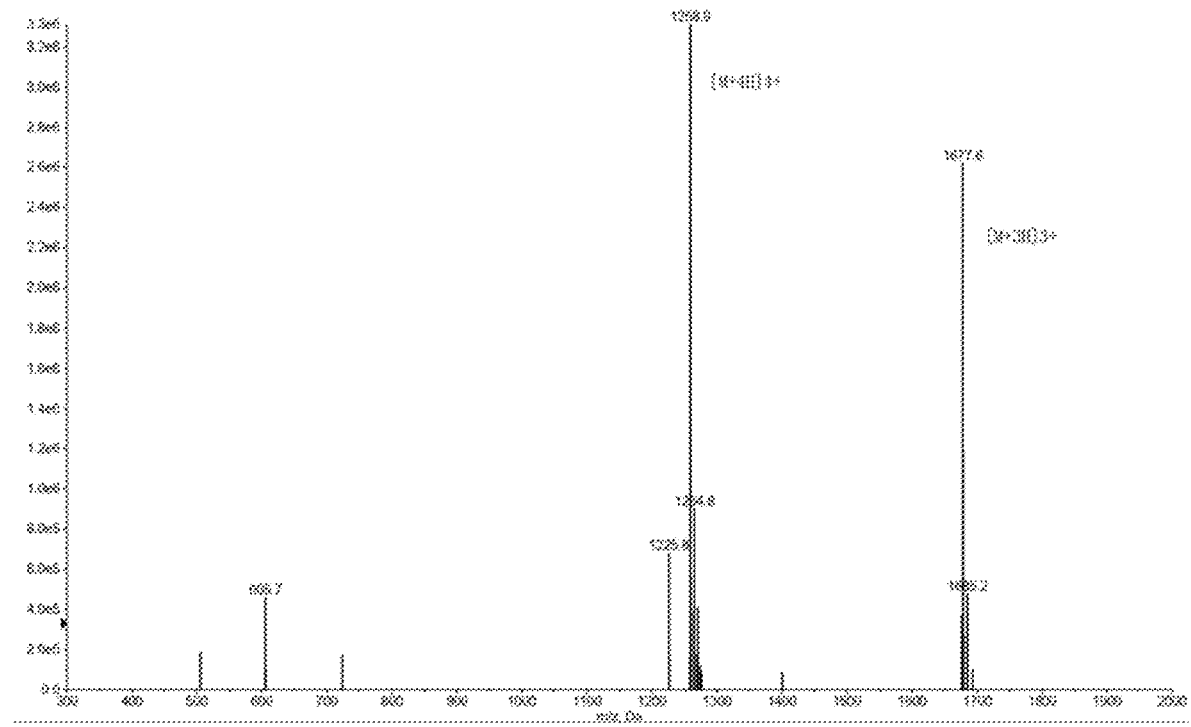
FIG. 1 shows the mass spectrum of compound BG128.

Unless stated to the contrary, the terms used in the present disclosure have the following meanings.

In the claims and/or specification of the present disclosure, the words "a", "an" or "the" can refer to "one", but can also refer to "one or more", "at least one" and "one or more than one".

As used in the claims and the description, the words "comprising", "having", "including" or "containing" refer to an inclusive and open-ended expression, which does not exclude additional, unquoted elements or method steps. Moreover, "comprising", "having", "including" or "containing" may also refer to a closed expression, which excludes additional, unquoted elements or method steps.

In the application document, the term "about" means a value comprising the standard deviation in the error caused by the device or method used to determine the value.

The term "agonist" used in the context of the present disclosure refers to a substance (ligand) that activates a signaling pathway through the targeted receptor type. For example, if a GLP-1 receptor is a target receptor, the agonist has the activation activity of GLP-1 receptor, and is such as a GLP-1 polypeptide or an analog thereof.

The term "$EC_{50}$" used in the context of the present disclosure refers to the half effective concentration, and in the present disclosure, the agonist activity of the compound is evaluated by $EC_{50}$. For example, with the GIP receptor as the target, the $EC_{50}$ of the compound on the GIP receptor is determined and used as the evaluation data of the agonist activity of the compound on GIP receptor.

The term "treating" used in the context of the present disclosure refer to: contacting (e.g., administering to) a subject suffering from a disease with the compound of the present disclosure, or the pharmaceutically acceptable salt, ester, solvate, optical isomer, tautomer, isotopically labeled compound or prodrug thereof or the pharmaceutical composition containing same (hereinafter also referred to as "the pharmaceutical composition of the present disclosure"), thereby reducing the symptoms of the disease compared with those without the contacting, and it does not mean that the symptoms of the disease must be completely suppressed. Suffering from a disease refers to: the body has symptoms of the disease.

The term "preventing" used in the context of the present disclosure refer to: contacting (e.g., administering to) a subject before suffering from a disease with the compound of the present disclosure, or the pharmaceutically acceptable salt, ester, solvate, optical isomer, tautomer, isotopically labeled compound or prodrug thereof or the pharmaceutical composition of the present disclosure, thereby reducing the symptoms after suffering from the disease compared with those without the contacting, and it does not mean that the disease must be completely prevented.

The terms "individual", "patient" or "subject" used in the context of the present disclosure include mammals. Mammals include, but are not limited to, domesticated animal (e.g., cow, sheep, cat, dog, and horse), primate (e.g., human and non-human primate, such as monkey), rabbit, and rodent (e.g., mouse and rat).

The term "therapeutically effective amount" used in the context of the present disclosure refers to an amount effective to achieve the desired therapeutic result at a dose and for periods of time desired. The therapeutically effective amount of the compound or pharmaceutical composition of the present disclosure can vary depending on factors such as disease state, age, sex and weight of an individual, and the ability of an immune adjuvant or the pharmaceutical composition to activate a desired response in an individual.

The term "pharmaceutically acceptable salt" used in the context of the present disclosure refers to a salt prepared from the compound of the present disclosure with a relatively non-toxic acid or base. When the compound of the present disclosure contains a relatively acidic functional group (such as carboxy or sulfonic acid group), a base addition salt can be obtained by contacting the free form of the compound with a sufficient amount of base, either in a pure solution or a suitable inert solvent. Non-limiting examples of pharmaceutically acceptable base addition salts include, but are not limited to, sodium salts, potassium salts, ammonium salts, calcium salts, magnesium salts, organic amine salts, or similar salts. When the compound of the present disclosure contains a relatively basic functional group (such as amino or guanidyl), an acid addition salt can be obtained by contacting the free form of the compound with a sufficient amount of acid, either in a pure solution or a suitable inert solvent. Non-limiting examples of pharmaceutically acceptable acid addition salts include, but are not limited to, inorganic acid salts (e.g., hydrochloride, hydrobromide, hydroiodide, nitrate, carbonate, bicarbonate, phosphate, monohydrogen phosphate, dihydrogen phosphate, phosphite, sulfate, bisulfate salts, etc.), organic acid salts (such as acetate, propionate, isobutyrate, malonate, succinate, suberate, maleate, fumarate, citrate, tartrate, lactate, mandelate, benzoate, phthalate, mesylate, besylate, p-tosylate glucuronate salts, etc.) and amino acid salts (such as arginine salt, etc.). For specific forms of pharmaceutically acceptable salts, also see Berge et al., "Pharmaceutical Salts", *Journal of Pharmaceutical Science,* 1977, 66:1-19.

The term "pharmaceutical composition" used in the context of the present disclosure refers to a pharmaceutically acceptable composition comprising one or more compounds represented by formula I or pharmaceutically acceptable forms thereof (such as a salt, hydrate, solvate, stereoisomer, tautomer, metabolite, prodrug, etc.), and other components (such as pharmaceutically acceptable excipient, etc.).

The term "pharmaceutically acceptable excipient" used in the context of the present disclosure refers to an auxiliary material widely used in the field of pharmaceutical production. The main purpose of using an excipient is to provide a pharmaceutical composition that is safe to use, stable in nature and/or has specific functionality, and also to provide a method for dissolving the active ingredient at a desired rate after the drug is administered to the subject or for promoting the effective absorption of the active ingredient in the subject receiving the administration. The pharmaceutically acceptable excipient can be an inert filler or a functional ingredient that provides certain functions for the pharmaceutical composition, such as stabilizing the overall pH value of the composition or preventing the degradation of the active ingredients of the composition. Non-limiting examples of the pharmaceutically acceptable excipient include, but are not limited to, binders, suspending agents, emulsifiers, diluents (or fillers), granulating agents, adhesives, disintegrating agents, lubricants, anti-adhesive agents, glidants, wetting agents, gelling agents, absorption delaying agents, dissolution inhibitors, reinforcing agents, adsorbents, buffers, chelating agents, preservatives, colorants, flavoring agents and sweetening agents.

The pharmaceutical compositions of the present disclosure can be prepared using any methods known to a person skilled in the art, such as, conventional mixing, dissolving, granulating, emulsifying, grinding, encapsulating, embedding and/or lyophilizing processes.

In the present disclosure, the purpose of using a pharmaceutical composition is to promote the administration to organism, and facilitate absorption of the active ingredient, thereby exerting biological activity. The pharmaceutical compositions of the present disclosure can be administered via any route, including injection administration (intraarterial, intravenous, intramuscular, intraperitoneal and subcutaneous), mucosal administration, oral administration (oral solid preparation and oral liquid preparation), rectal administration, inhalation administration, implantation administration, topical administration (e.g., eye), etc. Non-limiting examples of oral solid preparations include, but are not limited to, powders, capsules, troches, granules, tablets, etc. Non-limiting examples of liquid preparations for oral or mucosal administration include, but are not limited to, suspensions, tinctures, elixirs, solutions, etc. Non-limiting examples of preparations for topical administration include, but are not limited to, emulsions, gels, ointments, creams, patches, pastes, foams, lotions, drops, or serum preparations. Non-limiting examples of preparations for parenteral administration include, but are not limited to, solutions for injection, dry powders for injection, suspensions for injection, emulsions for injection, etc. The pharmaceutical composition of the present disclosure can also be formulated as a controlled release or delayed release dosage form (such as liposome or microsphere).

In the present disclosure, the routes of administration can be varied or adjusted in any suitable manner to meet the needs of the drug nature, the convenience of the patient and medical personnel, and other relevant factors.

The term "metabolic disorder" used in the context of the present disclosure can refer to disorders of glucose metabolism, such as diabetes, diabetes complications, obesity and obesity complications. Since the association between obesity, diabetes and blood glucose metabolism is well known, these conditions can, but need not be, separate or mutually exclusive. In some embodiments, diabetes or diabetes complications include insulin resistance, glucose intolerance, elevated fasting blood glucose, prediabetes, type I diabetes, type II diabetes, gestational diabetes hypertension, dyslipidemia, or a combination thereof. In some embodiments, obesity complications include obesity-associated inflammation, obesity-associated gallbladder diseases, or obesity-induced sleep apnea, or may be selected from the following related conditions: atherogenic dyslipidemia, dyslipidemia, increased blood pressure, hypertension, prothrombotic state and proinflammatory state, or a combination thereof.

The compound or the pharmaceutically acceptable salt, hydrate, solvate, stereoisomer, tautomer, metabolite or prodrug thereof or the pharmaceutical composition comprising same of the present disclosure has excellent GIPR and GLP-1R dual agonist activity, can effectively reduce blood sugar and control the body weight growth of type 2 diabetes model mice, is used for preventing and/or treating metabolic disorders, and has good clinical and medical uses.

The technical solutions of the present disclosure are described in conjunction with specific examples below. The following examples are provided to further illustrate the present disclosure and are not intended to limit the scope of the present disclosure. Various changes and improvements to the specific embodiments of the present disclosure would be obvious to a person skilled in the art without departing from the spirit and scope of the present disclosure.

The compounds of the present disclosure can be prepared by various synthetic methods well known to a person skilled in the art, including but not limited to the specific embodiments listed below, the embodiments formed by the combination of the specific embodiments with other chemical synthesis methods, and equivalent alternative embodiments well known to a person skilled in the art, wherein the preferred embodiments include but are not limited to the examples of the present disclosure. Known starting materials used in the present disclosure can be synthesized by a method known in the art, or can be purchased by conventional commercial means.

The separation and purification of the compound of the present disclosure can be performed by synthetic methods well known to a person skilled in the art, including but not limited to column chromatography (CC), high performance liquid chromatography (HPLC), ultra-high performance liquid chromatography (UPLC), etc.

Amino acid names and English abbreviations thereof in the present disclosure are as shown in the following table:

| Names and abbreviations of protected amino acids required for Fmoc solid-phase synthesis | | | |
|---|---|---|---|
| Name | Protected amino acid | Three-letter abbreviation | One-letter abbreviation |
| Alanine | Fmoc-Ala-OH | Ala | A |
| Aspartic acid | Fmoc-Asp (OtBu)-OH | Asp | D |
| Glutamic acid | Fmoc-Glu (OtBu)-OH Fmoc-Glu-OtBu | Glu | E |

-continued

| Names and abbreviations of protected amino acids required for Fmoc solid-phase synthesis | | | |
|---|---|---|---|
| Name | Protected amino acid | Three-letter abbreviation | One-letter abbreviation |
| Phenylalanine | Fmoc-Phe-OH | Phe | F |
| Glycine | Fmoc-Gly-OH | Gly | G |
| Isoleucine | Fmoc-Ile-OH | Ile | I |
| Lysine | Fmoc-Lys (Boc)-OH Fmoc-Lys (Alloc)-OH | Lys | K |
| Leucine | Fmoc-Leu-OH | Leu | L |
| Proline | Fmoc-Pro-OH | Pro | P |
| Glutamine | Fmoc-Gln (Trt)-OH | Gln | Q |
| Serine | Fmoc-Ser (tBu)-OH | Ser | S |
| Threonine | Fmoc-Thr (tBu)-OH | Th | T |
| Valine | Fmoc-Val-OH | Val | V |
| Tryptophan | Fmoc-Trp (Boc)-OH | Trp | W |
| Tyrosine | Fmoc-Tyr (tBu)-OH Boc-Tyr (tBu)-OH | Tyr | Y |
| 2-aminoisobutyric acid | Fmoc-Aib-OH | Aib | / |

EXAMPLE

Other objects, features, and advantages of the present disclosure will be apparent from the following detailed description. However, it should be understood that the detailed description and particular example (while indicating the specific implementation manners of the present disclosure) are given for the purpose of explanation only, because various changes and modifications made within the spirit and scope of the present disclosure will become apparent to a person skilled in the art upon reading the detailed specification.

Unless specially indicated, all reagents and materials used in the present disclosure are purchased commercially.

Example 1 Solid-Phase Synthesis of Target Compound BG128 by Fmoc Method

Compound Structure of BG128 (SEQ ID NO: 17):

I-3

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser

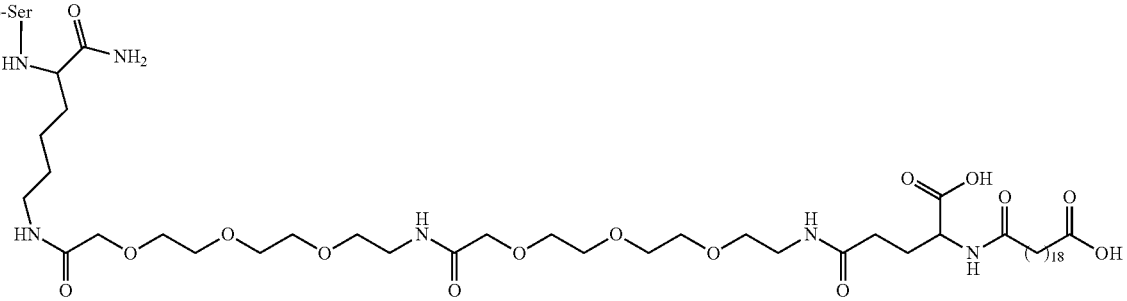

Synthetic Step:

Fmoc-Rink MBHA Amide resin was used, 20% of piperidine/DMF was used to remove Fmoc, HOBT/DIC was used as a coupling reagent, DMF was used as a reaction solvent, and the reaction was monitored by a ninhydrin detection method.

(1) The following protected amino acids were sequentially coupled to Rink MBHA Amide resin:

Fmoc-Lys(Alloc)-OH, Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Ala-OH, Fmoc-Ile-OH, Fmoc-Leu-OH, Fmoc-Trp(Boc)-OH, Fmoc-Gln(Trt)-OH, Fmoc-Val-OH, Fmoc-Phe-OH, Fmoc-Ala-OH, Fmoc-Lys(Boc)-OH, Fmoc-Gln(Trt)-OH, Fmoc-Ala-OH, Fmoc-Ile-OH, Fmoc-Lys(Boc)-OH, Fmoc-Asp(OtBu)-OH, Fmoc-Leu-OH, Fmoc-Aib-OH, Fmoc-Ile-OH, Fmoc-Ser(tBu)-OH, Fmoc-Tyr(tBu)-OH, Fmoc-Asp(OtBu)OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Aib-OH, and Boc-Tyr(tBu)-OH.

(2) Removal of the protecting group: a solution of 3 eq of Pd (PPh$_3$)$_4$ in CHCl$_3$:AcOH:NMM (18:1:0.5) was added, and the mixture was reacted for 2 h, then washed with chloroform (6*30 ml), and washed with a solution of HOAc (20%) in DCM (6*30 ml), DCM (6*30 ml) and DMF (6*30 ml); the ninhydrin detection result of the mixture was positive; and then Fmoc-AEEEA-OH, Fmoc-AEEEA-OH, Fmoc-Glu-OtBu and 20-(tert-butoxy)-20-oxoicosanoic acid were sequentially condensed to obtain a fully protected resin of BG128.

(3) Cleavage from resin: 95% TFA/2.5% water/2.5TIS was used, and then a cold MTBE was used for precipitation and washing. The crude product was purified by HPLC and lyophilized to obtain the target compound BG128. The MS spectrum of the compound BG128 is shown in FIG. 1.

The abbreviations used are as follows:

DMF, N,N-dimethylformamide; Fmoc, 9-fluorenylmethyloxycarbonyl; HOBT, N-hydroxybenzotriazole; DIC, N,N-diisopropylcarbodiimide; NMM, N-methylmorpholine; DCM, dichloromethane; Fmoc-AEEEA-OH, [2-[2-[2-(Fmoc-amino)ethoxy]ethoxy]ethoxy]acetic acid; MTBE, methyl tert-butyl ether; TFA, trifluoroacetic acid; TIS, triisopropylsilane.

Example 2 Solid-Phase Synthesis of the Compound Represented by Formula I-1 by Fmoc Method Structure of the Compound Represented by Formula I-1 (SEQ ID NO: 3):

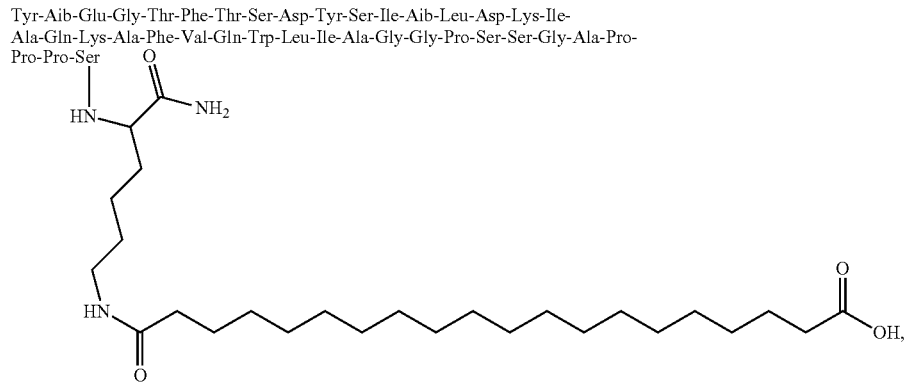

Synthetic Step:

the compound represented by formula I-1 was obtained according to the preparation method as shown in example 1, wherein in step (2), 20-(tert-butoxy)-20-oxoicosanoic acid was condensed at the side chain, and for the compound represented by formula I-1, MS: $[M+3]^{3+}$ is 1508.4.

Example 3 Solid-Phase Synthesis of the Compound Represented by Formula I-2 by Fmoc Method Structure of the Compound Represented by Formula I-2 (SEQ ID NO: 4):

I-2

Tyr-Aib-Glu-Thr-Phe-Thr-Ser-Asp-Tyr-Ser-Ile-Aib-Leu-Asp-Lys-Ile-
Ala-Gln-Lys-Ala-Phe-Val-Gln-Trp-Leu-Ile-Ala-Gly-Gly-Pro-Ser-Ser-Gly-Ala-Pro-
Pro-Pro-Ser

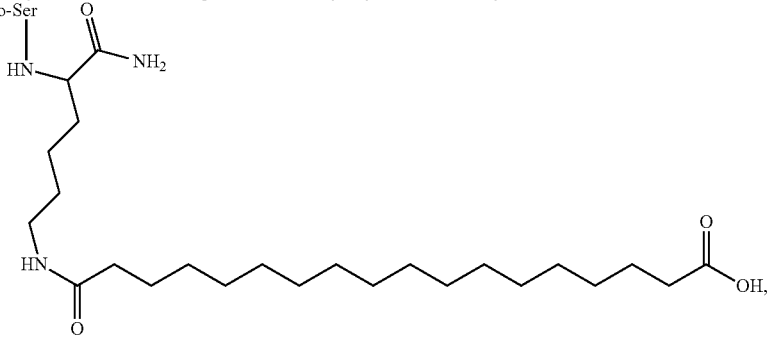

Synthetic Step:
the compound represented by formula I-2 was obtained according to the preparation method as shown in example 1, wherein in step (2), 18-(tert-butoxy)-18-oxooctadecanoic acid was condensed at the side chain, and for the compound represented by formula I-2, MS: $[M+3]^{3+}$ is 1499.0.

Example 4 Solid-Phase Synthesis of the Compound Represented by Formula I-4 by Fmoc Method Structure of the Compound Represented by Formula I-4 (SEQ ID NO: 6):

I-4

Tyr-Aib-Glu-Gly-Thr-Phe-Thr-Ser-Asp-Tyr-Ser-Ile-Aib-Leu-Asp-Lys-Ile-
Ala-Gln-Lys-Ala-Phe-Val-Gln-Trp-Leu-Ile-Ala-Gly-Gly-Pro-Ser-Ser-Gly-Ala-Pro-
Pro-Pro-Ser

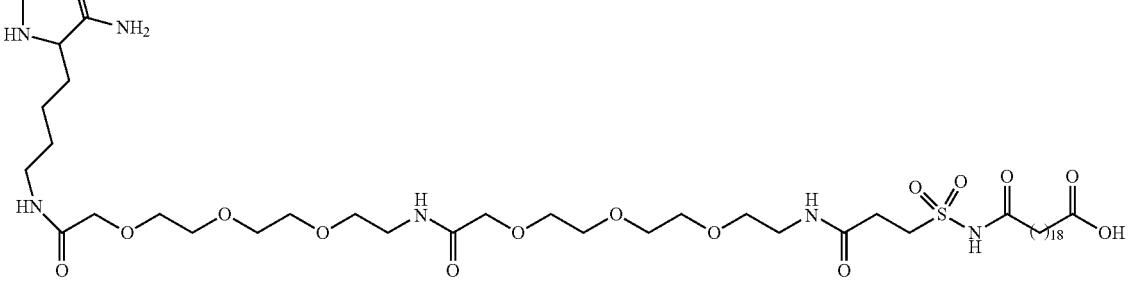

Synthetic Step:
the compound represented by formula I-4 was obtained according to the preparation method as shown in example 1, wherein in step (2), Fmoc-AEEEA-OH, Fmoc-AEEEA-OH and 3-(N-(20-(tert-butoxy)-20-oxoeicosanoyl)sulfamoyl)propionic acid were sequentially condensed at the side chain, and for the compound represented by formula I-4, MS: $[M+3]^{3+}$ is 1679.6.

Example 5 Solid-Phase Synthesis of the Compound Represented by Formula I-5 by Fmoc Method Structure of the Compound Represented by Formula I-5 (SEQ ID NO: 7):

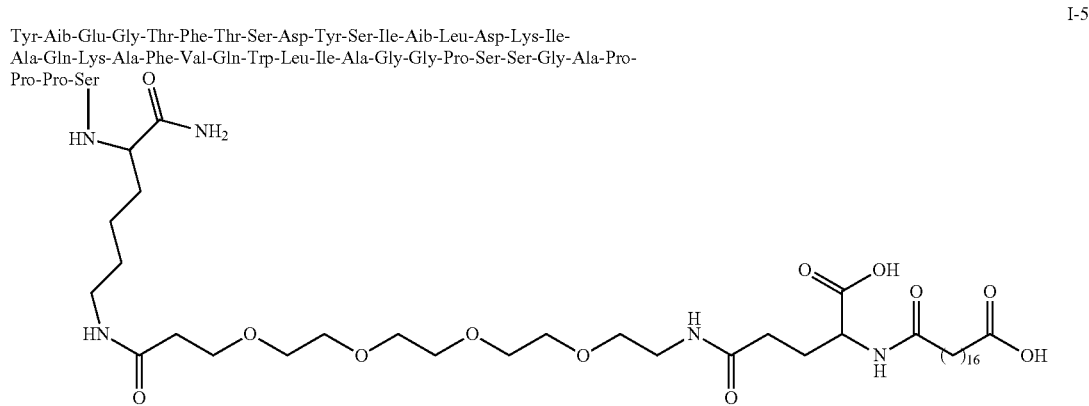

I-5

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser

Synthetic Step:

the compound represented by formula I-5 was obtained according to the preparation method as shown in example 1, wherein in step (2), Fmoc-NH-PEG4-PA, Fmoc-Glu-OtBu and 18-(tert-butoxy)-18-oxooctadecanoic acid were sequentially condensed at the side chain, and for the compound represented by formula I-5, MS: $[M+3]^{3+}$ is 1626.5 and $[M+4]^{4+}$ is 1220.1.

Example 6 Solid-Phase Synthesis of the Compound Represented by Formula I-6 by Fmoc Method Structure of the Compound Represented by Formula I-6 (SEQ ID NO: 8):

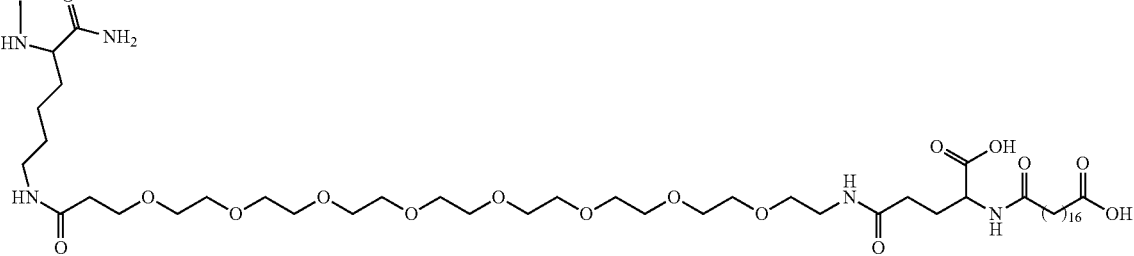

I-6

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser

Synthetic Step:

the compound represented by formula I-6 was obtained according to the preparation method as shown in example 1, wherein in step (2), Fmoc-NH-PEG8-PA, Fmoc-Glu-OtBu and 18-(tert-butoxy)-18-oxooctadecanoic acid were sequentially condensed at the side chain, and for the compound represented by formula I-6, MS: $[M+3]^{3+}$ is 1683.2 and $[M+4]^{4+}$ is 1262.7.

Example 7 Solid-Phase Synthesis of the Compound Represented by Formula I-7 by Fmoc Method Structure of the Compound Represented by Formula I-7 (SEQ ID NO: 9):

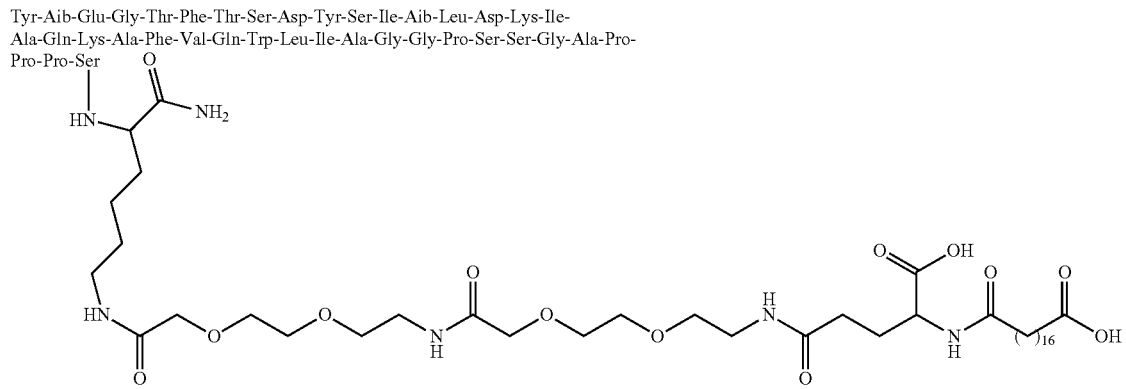

I-7

Synthetic Step:
the compound represented by formula I-7 was obtained according to the preparation method as shown in example 1, wherein in step (2), Fmoc-AEEA-OH, Fmoc-AEEA-OH, Fmoc-Glu-OtBu and 18-(tert-butoxy)-18-oxooctadecanoic acid were sequentially condensed at the side chain, and for the compound represented by formula I-7, MS: $[M+3]^{3+}$ is 1638.8 and $[M+4]^{4+}$ is 1229.4.

Example 8 Solid-Phase Synthesis of the Compound Represented by Formula I-8 by Fmoc Method Structure of the Compound Represented by Formula I-8 (SEQ ID NO: 10):

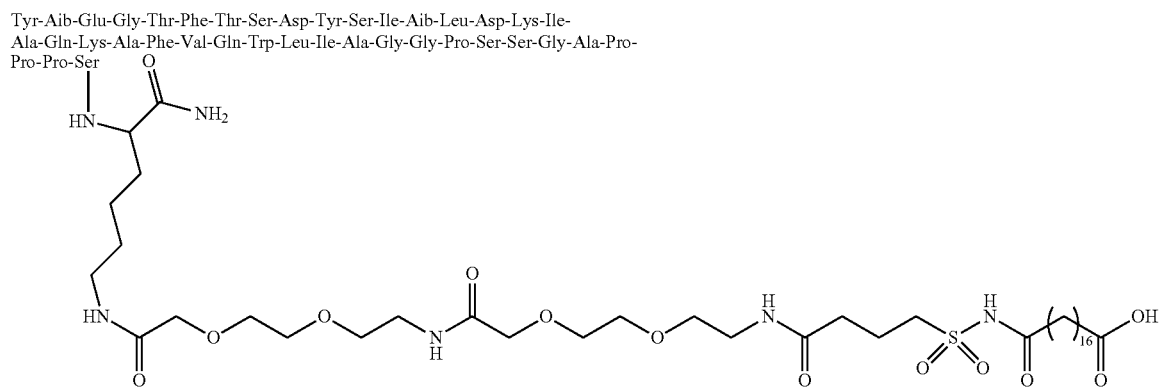

I-8

Synthetic Step:
the compound represented by formula I-8 was obtained according to the preparation method as shown in example 1, wherein in step (2), Fmoc-AEEA-OH, Fmoc-AEEA-OH and 4-(N-(18-(tert-butoxy)-18-oxostearoyl)sulfamoyl)butyric acid were sequentially condensed at the side chain, and for the compound represented by formula I-8, MS: $[M-3]^{3-}$ is 1643.5.

Example 9 Solid-Phase Synthesis of the Compound Represented by Formula I-9 by Fmoc Method Structure of the Compound Represented by Formula I-9 (SEQ ID NO: 11):

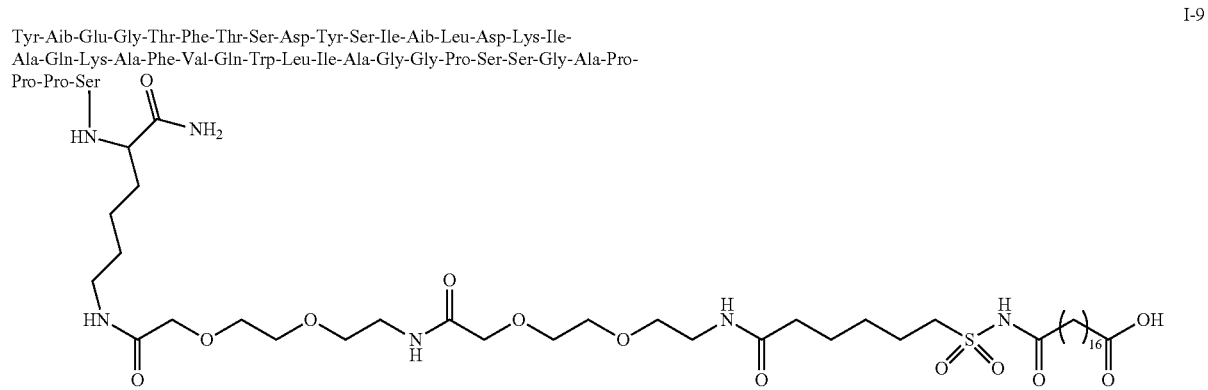

I-9

Synthetic Step:
the compound represented by formula I-9 was obtained according to the preparation method as shown in example 1, wherein in step (2), Fmoc-AEEA-OH, Fmoc-AEEA-OH and 6-(N-(18-((tert-butoxy))-18-oxostearoyl)sulfamoyl)hexanoic acid were sequentially condensed at the side chain, and for the compound represented by formula I-9, MS: $[M-3]^{3-}$ is 1652.9.

Example 10 Solid-Phase Synthesis of the Compound Represented by Formula I-10 by Fmoc Method Structure of the Compound Represented by Formula I-10 (SEQ ID NO: 12):

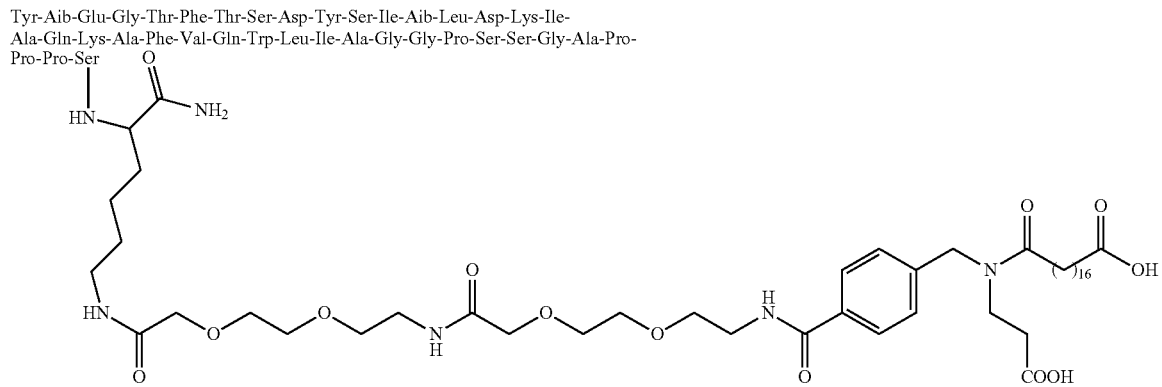

I-10

Synthetic Step:
the compound represented by formula I-10 was obtained according to the preparation method as shown in example 1, wherein in step (2), Fmoc-AEEA-OH, Fmoc-AEEA-OH and 4-((18-(tert-butoxy)-N-(3-(tert-butoxy)-3-oxopropyl)-18-oxostearamide)methyl)benzoic acid were sequentially condensed at the side chain, and for the compound represented by formula I-10, MS: $[M+3]^{3+}$ is 1664.2.

Example 11 Solid-Phase Synthesis of the Compound Represented by Formula I-11 by Fmoc Method Structure of the Compound Represented by Formula I-11 (SEQ ID NO: 13):

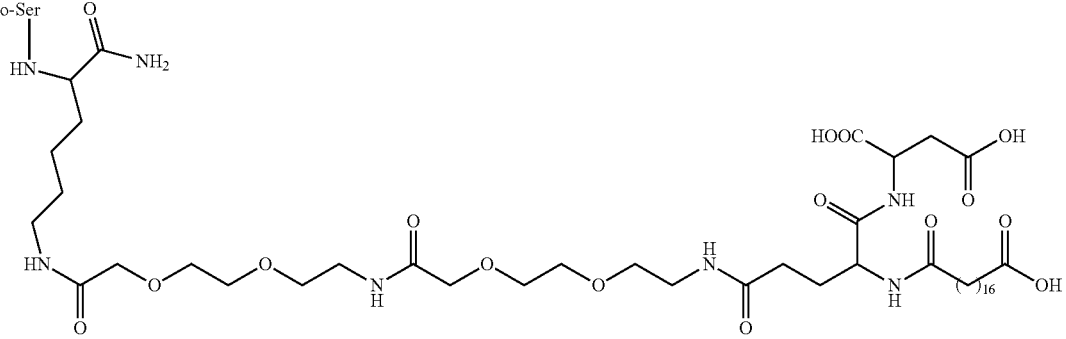

I-11

Synthetic Step:

the compound represented by formula I-11 was obtained according to the preparation method as shown in example 1, wherein in step (2), Fmoc-AEEA-OH, Fmoc-AEEA-OH, Fmoc-Glu-(Asp(OtBu)-OtBu)-OH and 18-(tert-butoxy)-18-oxooctadecanoic acid were sequentially condensed at the side chain, and for the compound represented by formula I-11, MS: $[M+3]^{3+}$ is 1677.2.

Example 12 Solid-Phase Synthesis of the Compound Represented by Formula I-12 by Fmoc Method Structure of the Compound Represented by Formula I-12 (SEQ ID NO: 14):

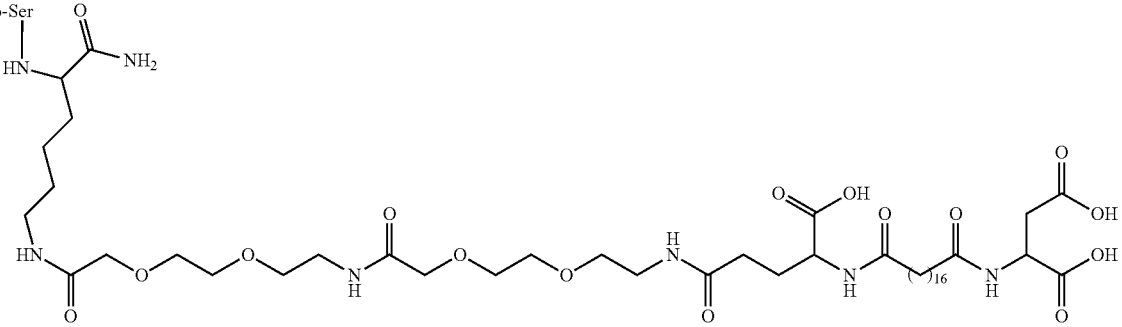

I-12

Synthetic Step:

the compound represented by formula I-12 was obtained according to the preparation method as shown in example 1, wherein in step (2), Fmoc-AEEA-OH, Fmoc-AEEA-OH, Fmoc-Glu-OtBu and Asp[(OtBu)-OtBu]-octadecanedioic acid were sequentially condensed at the side chain, and for the compound represented by formula I-12, MS: $[M+3]^{3+}$ is 1677.2.

Example 13 Solid-Phase Synthesis of the Compound Represented by Formula I-13 by Fmoc Method Structure of the Compound Represented by Formula I-13 (SEQ ID NO: 15):

I-13

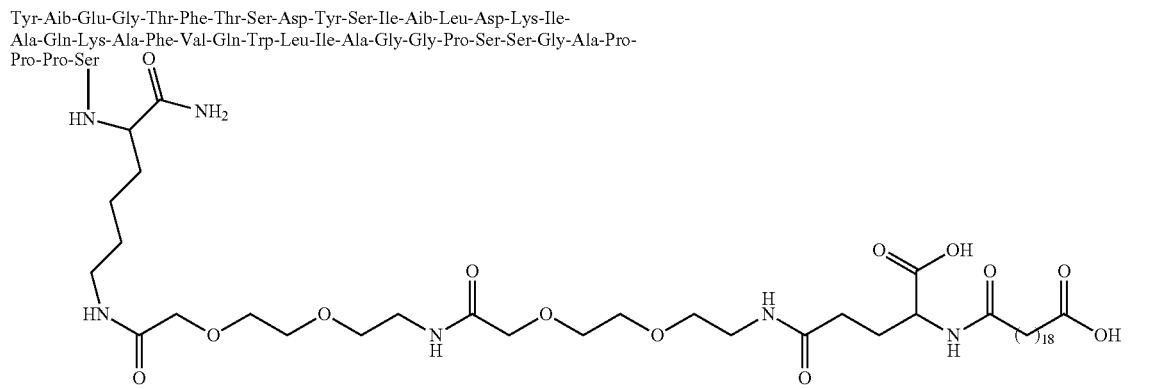

Synthetic Step:

the compound represented by formula I-13 was obtained according to the preparation method as shown in example 1, wherein in step (2), Fmoc-AEEA-OH, Fmoc-AEEA-OH, Fmoc-Glu-OtBu and 20-(tert-Butoxy)-20-oxoicosanoic acid were sequentially condensed at the side chain, and for the compound represented by formula I-13, MS: $[M+3]^{3+}$ is 1648.1.

Example 14 Solid-Phase Synthesis of the Compound Represented by Formula I-14 by Fmoc Method Structure of the Compound Represented by Formula I-14 (SEQ ID NO: 16):

I-14

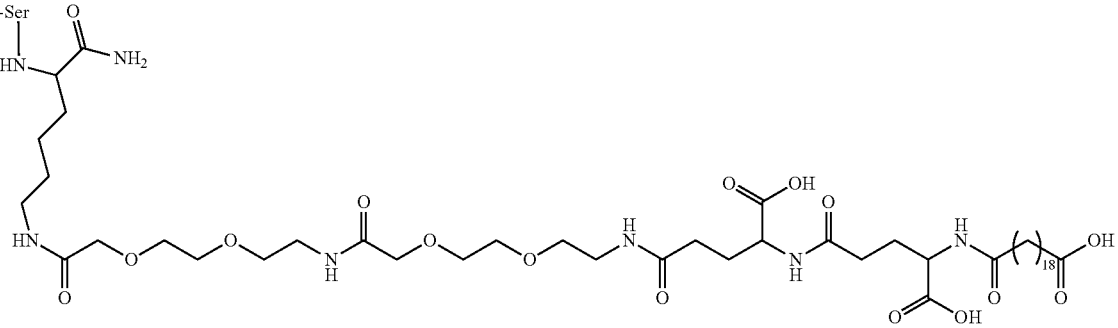

Synthetic Step:

the compound represented by formula I-14 was obtained according to the preparation method as shown in example 1, wherein in step (2), Fmoc-AEEA-OH, Fmoc-AEEA-OH, Fmoc-Glu-OtBu, Fmoc-Glu-OtBu and 20-(tert-Butoxy)-20-oxoicosanoic acid were sequentially condensed at the side chain, and for the compound represented by formula I-14, MS: $[M+3]^{3+}$ is 1691.2.

Comparative Example 1 Solid-Phase Synthesis of Target Compound BGM125 by Fmoc Method Compound structure of BGM125 (SEQ ID NO: 18):

```
1     5    10   15   20   25   30   35  39
YAibEGTFTSDYSIAibLDKIAQKAFVQWLIAGGPSSGAPPPS—NH2
```

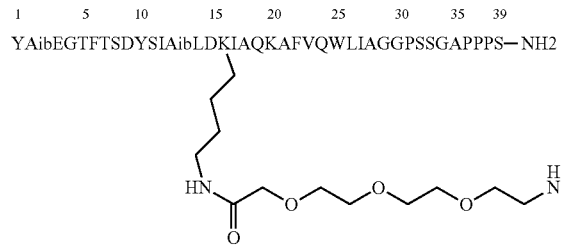

and wherein the amino acid sequence of the polypeptide in the compound BGM125 is as shown in SEQ ID NO: 1.

Synthetic Step:

In the solid-phase peptide synthesis of the target peptide, Fmoc-Rink MBHA Amide resin was used, 20% of piperidine/DMF was used to remove Fmoc, HOBT/DIC was used as a coupling reagent, DMF was used as a reaction solvent, and the reaction was monitored by a ninhydrin detection method:

(1) The following protected amino acids were sequentially coupled to Rink MBHA Amide resin:

Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Ala-OH, Fmoc-Ile-OH, Fmoc-Leu-OH, Fmoc-Trp(Boc)-OH, Fmoc-Gln(Trt)-OH, Fmoc-Val-OH, Fmoc-Phe-OH, Fmoc-Ala-OH, Fmoc-Lys(Boc)-OH, Fmoc-Gln(Trt)-OH, Fmoc-Ala-OH, Fmoc-Ile-OH, Fmoc-Lys(Alloc)-OH, Fmoc-Asp(OtBu)-OH, Fmoc-Leu-OH, Fmoc-Aib-OH, Fmoc-Ile-OH, Fmoc-Ser(tBu)-OH, Fmoc-Tyr(tBu)-OH, Fmoc-Asp(OtBu)OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Aib-OH and Boc-Tyr(tBu)-OH.

(2) Removal of the protecting group: a solution of 3 eq of Pd (PPh$_3$)$_4$ in CHCl$_3$:AcOH:NMM (18:1:0.5) was added, and the mixture was reacted for 2 h, then washed with chloroform (6*30 ml), and washed with a solution of HOAc (20%) in DCM (6*30 ml), DCM (6*30 ml) and DMF (6*30 ml); the ninhydrin detection result of the mixture was positive; and then Fmoc-AEEEA-OH, Fmoc-AEEEA-OH, Fmoc-Glu-OtBu and 20-(tert-butoxy)-20-oxoicosanoic acid were sequentially condensed to obtain a fully protected resin of BGM125.

Figure 2:
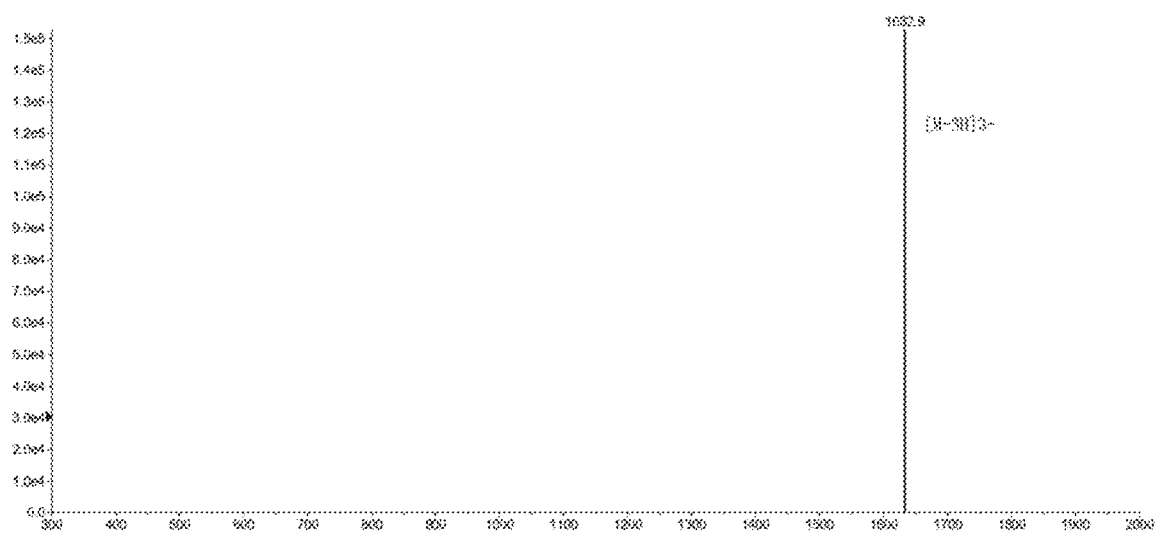
FIG. 2 shows the mass spectrum of compound BGM125.

(3) Cleavage from resin: 95% TFA/2.5% water/2.5TIS was used, and then a cold methyl tert-butyl ether (MTBE) was used for precipitation and washing. The crude product was purified by HPLC and lyophilized to obtain the target compound BGM125. The target compound BGM125 was characterized by MS and the result is shown in FIG. 2.

Experimental Example 1

1. Experiment Materials 1.1 Reagents and Equipments:

cAMP detection kit, Cisbio; 1M HEPES, Invitrogen; 1×HBSS, Invitrogen;
Casein, Sigma; IBMX, Sigma; GIP(GIP), Tocris;
Host cell for GLP-1R: HEK293 cell line, preserved in BRIGHTGENE BIO-MEDICAL TECHNOLOGY CO., LTD.;
Host cell for GIP R: CHO cell line, preserved in BRIGHTGENE BIO-MEDICAL TECHNOLOGY CO., LTD.;
OptiPlate-384 plate, PerkinElmer; 384 Echo plate, Labcyte; EnVision, PerkinElmer; Honeycomb counter, Beckman;

1.2 Test Compounds:

TABLE 1

Test compounds for cell experiment

| Name/Abbreviated name | BG121 (LY3298176) | BG128 | BGM125 | BGM134 (Semaglutide) |
|---|---|---|---|---|
| Specification | 2.69 mg | 2.80 mg | 2.80 mg | 10 mg |
| Content | 96.64% | 95.61% | 95.61% | 95.61% |
| Character | White powder | White powder | White powder | White powder |
| Preservation condition | −20° C. | −20° C. | −20° C. | −20° C. |
| Source | BRIGHTGENE BIO-MEDICAL TECHNOLOGY CO., LTD. | BRIGHTGENE BIO-MEDICAL TECHNOLOGY CO., LTD. | BRIGHTGENE BIO-MEDICAL TECHNOLOGY CO., LTD. | Purchased |

2. Experimental Method a) Preparation of Compound Plate:

(1) The compounds to be tested for the GIPR target were BG121, BG128, BGM125 and BGM134. Each compound was serially 4-fold diluted to make 10 serial concentrations, the starting concentration was 5 μM, and Bravo was used to complete the dilution. Reference compound GIP was serially 4-fold diluted to make 10 serial concentrations, the starting concentration was 5 uM, and Bravo was used to complete the dilution.

(2) The compounds to be tested for the GLP-1R target were BG 121, BG128, BGM125 and BGM134. Each compound was serially 4-fold diluted to make 10 serial concentrations, the starting concentration was 0.5 μM, and Bravo was used to complete the dilution. Reference compound GLP-1 (7-37) was serially 4-fold diluted to make 10 serial concentrations, the starting concentration was 2 μM, and Bravo was used to complete the dilution.

b) Transfer of Compounds:

(1) 100 nL of compound was transferred to OptiPlate-384 plate using an Echo pipette.

(2) OptiPlate-384 plate was centrifuged at 1000 rpm for 5 seconds.

c) Preparation of Cell Suspension (1) One cryopreservation tube each for GLP-1R cells and GIPR cells was taken and placed quickly in warm water at 37° C. to thaw.

(2) The cell suspension was transferred to a 15 mL centrifuge tube and rinsed gently with 10 ml of HBSS.

(3) The centrifuge tube was centrifuged at 1000 rpm for 1 minute at room temperature.

(4) The supernatant was discarded.

(5) The cells at bottom were gently dispersed and gently rinsed with 10 ml of HBSS, the mixture was centrifuged to deposit cells, and finally the cells were resuspended with the experimental buffer.

(6) The cell density and viability were determined using Vi-cell.

(7) The GLP-1R cells were diluted with the experimental buffer to the concentration of $2.0*E^5$/mL.

(8) 100 nL of the diluted cell suspension were transferred into an OptiPlate-384 plate.

(9) The suspension was incubated for 30 minutes at room temperature.

d) Addition of Detection Reagent:

(1) 10 μL of 800 nM gradiently diluted cAMP standard was added to an empty well of the OptiPlate-384 plate.

(2) 10 μL of cAMP detection reagent was added.

(3) The OptiPlate-384 plate was covered with TopSeal-A film and incubated at room temperature for 60 minutes. Top Seal-A was removed, and En Vision was used to read.

3. Experimental Results

TABLE 2

| cAMP experimental result of GIP receptor | | |
|---|---|---|
| No. | Sample name | $EC_{50}$ (nM) |
| 1 | BG121 (LY3298176) | 1.794 |
| 2 | BG128 | 0.2785 |

TABLE 2-continued

| cAMP experimental result of GIP receptor | | |
|---|---|---|
| No. | Sample name | $EC_{50}$ (nM) |
| 3 | BGM125 | 0.6839 |
| 4 | BGM134 (Semaglutide) | >50 |
| Ref | GIP | 0.1397 |

TABLE 3

| cAMP experimental result of GLP-1 receptor | | |
|---|---|---|
| No. | Sample name | $EC_{50}$ (nM) |
| 1 | BG121 (LY3298176) | 0.2273 |
| 2 | BG128 | 0.1097 |
| 3 | BGM125 | 0.06922 |
| 4 | BGM134 (Semaglutide) | 0.01347 |
| Ref | GLP-1 | 0.005069 |

It can be seen from the data in Table 2 and Table 3 that the compound in the present disclosure has high dual receptor agonist activity on GLP-1 receptor and GIP receptor, the agonist activity on the GIP receptor is better than that of the existing dual receptor agonist LY3298176, and GLP-1 receptor agonist semaglutide, and the agonist activity on the GLP-1 receptor is better than that of LY3298176.

Experimental Example 2

1. Experiment Materials 1.1 Solvent

Name: citric acid solution;
Ingredient: 20 mM citric acid with pH 7.0;
Storage condition: 4° C.;
Supplier: Sangon Bioengineering (Shanghai) Co., Ltd.

1.2 Experiment Animals

Germline: BKS mice (db/db mice); source: Gempharmatech Co., Ltd.; license key: SCXK (SU) 2018-0008; certificate number: 202100117; grade: SPF; number: 32; gender: male; age: 8 weeks (at the beginning of modeling); animal identification: ear tag.

Feeding conditions: temperature: 22±2° C.; humidity: 40%-70%; lighting: artificial lighting simulates day and night changes; drinking water: free to drink; feed: mouse breeding feed, wherein the mice were fasted overnight before determining fasting blood sugar, and the mice were free to eat for the rest of the time.

1.3 Test Compounds

TABLE 4

| Test compounds for animal experiment | | |
|---|---|---|
| Name/Abbreviated name | BG121 (LY3298176) | BG128 |
| Specification | 2.69 mg | 2.80 mg |
| Content | 96.64% | 95.61% |
| Character | White powder | White powder |
| Preservation condition | −20° C. | −20° C. |
| Source | BRIGHTGENE BIO-MEDICAL TECHNOLOGY CO., LTD. | BRIGHTGENE BIO-MEDICAL TECHNOLOGY CO., LTD. |

1.4 4. Sample Preparation Method

Formulation of BG121 (1 mg/ml) stock solution: a certain amount of BG121 was weighed, an appropriate volume of solvent (20 mM citric acid, pH 7.0) was added, and the mixture was sub-packaged at 100 μl/tube and frozen at −80° C. for later use;

Formulation of BG128 (1 mg/ml) stock solution: a certain amount of BG128 was weighed, an appropriate volume of solvent (20 mM citric acid, pH 7.0) was added, and the mixture was sub-packaged at 100 μl/tube and frozen at −80° C. for later use;

BG121 (0.0144 mg/ml, for 30 nmol/kg administration): 90 μL of the 1 mg/mL stock solution was taken and added to a 10 mL EP together with 810 μL of the solvent, the mixture was homogeneously mixed in a vortex mixer, then 5333 μL of the solvent was added, and the mixture was homogeneously mixed in a vortex mixer and used up on the same day;

BG128 (0.0151 mg/ml, for 30 nmol/kg administration): 90 μL of the 1 mg/mL stock solution was taken and added to a 10 mL EP together with 810 μL of the solvent, the mixture was homogeneously mixed in a vortex mixer, then 5044 μL of the solvent was added, and the mixture was homogeneously mixed in a vortex mixer and used up on the same day;

BG128 (0.0050 mg/ml, for 10 nmol/kg administration): 2 mL of BG128 (0.0144 mg/ml) were taken, and 4 mL of the solvent was added, and the mixture was homogeneously mixed in a vortex mixer and used up on the same day.

2. Experimental Design and Method

2.1 Experimental Design

32 SPF-grade male BKS-DB mice (db/db mice) were fed adaptively for 1 week. According to the fasting blood glucose level and body weight of the mice, the mice were randomly divided into 4 groups: solvent control group, BG121 (30 nmol/kg) group, BG128 (30 nmol/kg) group, BG128 (10 nmol/kg) group, and the mice were fed with a breeding feed. During the experiment, the experimenters need to observe the signs and health conditions of the experimental animals. Any abnormal manifestations of animals, such as pain, depression, decreased activity, etc., should be recorded in the original experimental records. If the abnormal manifestations of the experimental animals exceed the regulations in relevant documents for animal welfare, the animal can be euthanized after being notified. The experimental design was as shown in the following table.

TABLE 5

Grouping of mice

| Group number | Group | Number | Compound | Concentration (mg/mL) |
|---|---|---|---|---|
| 1 | Solvent control group | 8 | Citric acid | — |
| 2 | BG121 (30 nmol/kg) group | 8 | BG121 | 0.0144 |
| 3 | BG128 (30 nmol/kg) group | 8 | BG128 | 0.0151 |
| 4 | BG128 (10 nmol/kg) group | 8 | BG128 | 0.0050 |

2.2 Experimental Method

Modeling method: db/db mice would develop spontaneous type 2 diabetes after being fed for 6 weeks, and the mice would develop symptoms, such as obesity, insulin resistance and hyperglycemia;

Mode of administration: it was intended to use subcutaneous injection by the clinical route of administration, the volume of administration is: 10 mL/kg, once every 3 days, for 22 consecutive days;

Fasting blood glucose determination: according to the above-mentioned animal grouping and administration dose, the fasting blood glucose of the mice was determined two days before the first administration and the body weight was determined. The 8-week male mice with fasting blood glucose higher than 16.8 mmol/L were randomly grouped according to the blood glucose level. The fasting blood glucose levels were determined on day 7, 13, 19, and 25 after the first administration (changing the bedding and fasting before the fasting blood glucose determination), and the mice were fasted;

Non-fasting blood glucose determination: the blood glucose was determined at time points of 1, 3, 6, 24, 48, and 72 hours after the first administration;

Body weight determination: determined twice a week;

Food intake determination: determined twice a week.

2.3 Blood Biochemical Determination

After 25 days of administration, blood samples were collected by picking the eyeballs, and the serum insulin and glycosylated hemoglobin contents of the mice were determined respectively.

2.4 Statistical Processing

All reported determination data was calculated using GraphPad prism8.0 software for group mean and standard deviation.

3. Experimental Results

3.1 Changes of Non-Fasting Blood Glucose in db/db Mice after Single Administration of BG121 and BG128

Figure 3:
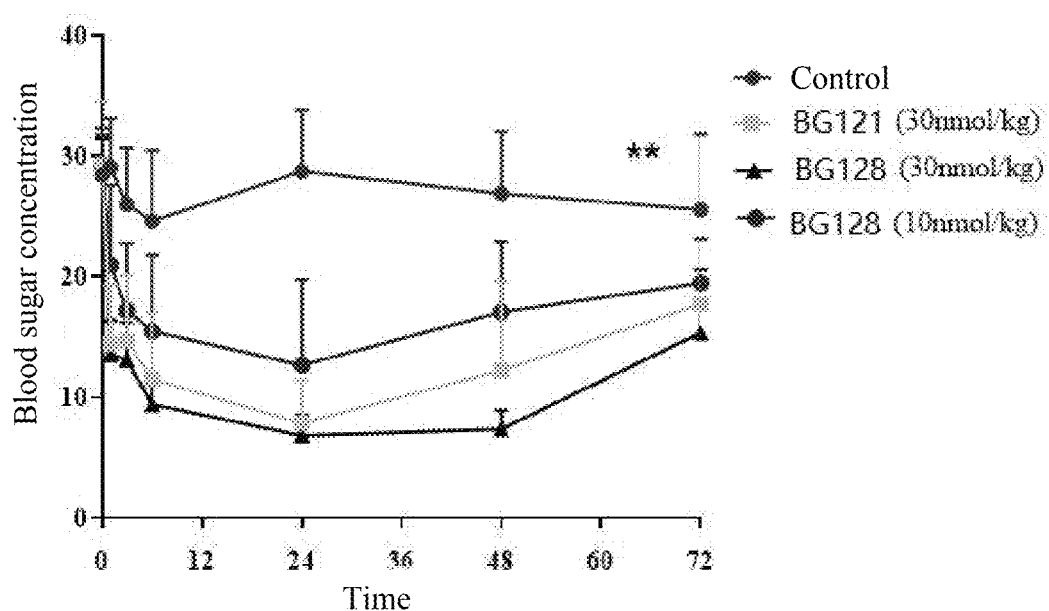
FIG. 3 shows the blood sugar levels determined in the db/db mice subcutaneously injected with BG121 (30 nmol/kg), BG128 (30 nmol/kg), BG128 (10 nmol/kg) and solvent control (Control), 1, 3, 6, 24, 48 and 72 h after administration; **, $P<0.01$ [BG121 (30 nmol/kg), BG128 (30, 10 nmol/kg) VS Control]

The db/db mice were subcutaneously injected with BG121 (30 nmol/kg), BG128 (30 nmol/kg) and BG128 (10 nmol/kg), respectively, and the changes in non-fasting blood glucose of the mice were determined 1, 3, 6, 24, 48 and 72 h after the first administration. The results showed that the blood glucose level at each time point after the administration of BG121 (30 nmol/kg) was lower than that of the solvent control group (Control); the administration of BG128 (30 nmol/kg) and BG128 (10 nmol/kg) can reduce the blood glucose at each time point after the administration in a dose dependent manner (FIG. 3).

3.2 Changes in Fasting Blood Glucose of db/db Mice after Administration of BG121 and BG128

Figure 4:
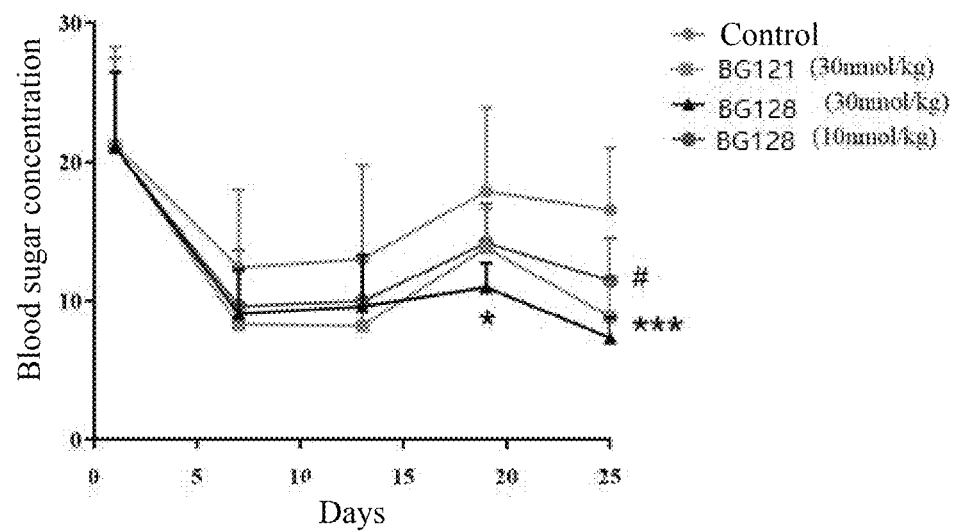
FIG. 4 shows the blood sugar levels determined in the db/db mice subcutaneously injected with BG121 (30 nmol/kg), BG128 (30 nmol/kg), BG128 (10 nmol/kg) and solvent control (Control) every 3 day on day 7, 13, 19 and 25 after first administration; *, $P<0.05$; ***, $P<0.001$ [BG121 (30 nmol/kg) VS Control]; #, $P<0.05$ [BG128 (30 nmol/kg) VS Control]

According to the experimental method, BG121, BG128 and the solvent as a control were subcutaneously administered to the db/db mice continuously, and the fasting blood glucose levels were measured on day 7, 13, 19, and 25 after the first administration. The results showed that on day 25 after the first administration of BG121 (30 nmol/kg) and BG121 (10 nmol/kg), the fasting blood glucose was significantly lower than that of the solvent control (Control), and on day 19 and 25 after the first administration, BG128 (30 nmol/kg) can significantly reduce the fasting blood glucose level, and the hypoglycemic effect is dose-dependent (FIG. 4).

3.3 Changes in Body Weight of db/db Mice after Administration of BG121 and BG128

Figure 5:
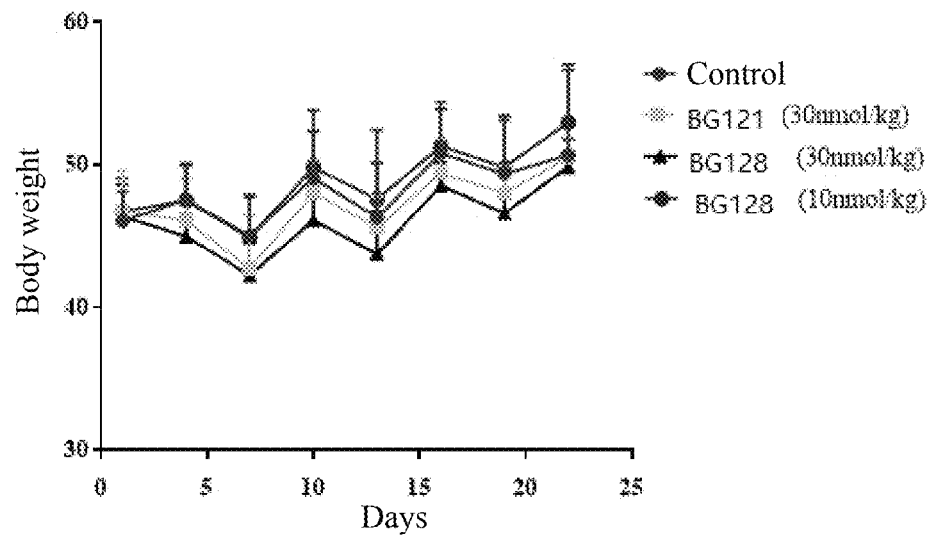
FIG. 5 shows the body weights of db/db mice subcutaneously injected with BG121 (30 nmol/kg), BG128 (30 nmol/kg), BG128 (10 nmol/kg) and solvent control (Control) every 3 day on day 4, 7, 10, 13, 16, 19 and 22 after first administration.

According to the experimental method, BG121, BG128, and the solvent control (Control) were administered to the db/db mice continuously, and the body weight of the mice was weighed on day 4, 7, 10, 13, 16, 19, and 22 after the first administration. The results showed that after administration, the average body weight of the mice in the BG128 (30 nmol/kg) administration group was lower than that in the solvent control group at each time point; while there was no significant difference in the body weight between BG128 (10 nmol/kg) administration group, BG121 (30 nmol/kg)

administration group and solvent control group. The results showed that the body weight of the mice in the BG128 (30 nmol/kg) administration group was significantly lower than that in the solvent control group and the BG121 (30 nmol/kg) administration group (FIG. 5).

3.4 Effects of BG121 and BG128 on Glycosylated Hemoglobin in db/db Mice

Figure 6:
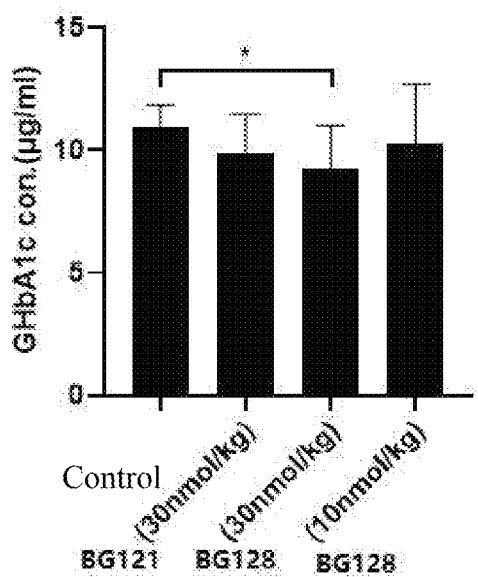
FIG. 6 shows the serum glycosylated hemoglobin contents determined in the db/db mice subcutaneously injected with BG121 (30 nmol/kg), BG128 (30 nmol/kg), BG128 (10 nmol/kg) and solvent control (Control) every 3 day on day 25 after first administration; *, $P<0.05$.

According to the experimental method, after 25 days of administration, the glycosylated hemoglobin content in the mouse serum was determined. The results showed that 25 days after the administration, the glycosylated hemoglobin content in the serum of the mice in the BG128 (30 nmol/kg) administration group was lower than that in the solvent control group, while there was no significant difference in the glycosylated hemoglobin contents between the BG128 (10 nmol/kg) administration group, the BG121 (30 nmol/kg) administration group and the solvent control group. The results showed that the glycosylated hemoglobin content of the mice in the BG128 (30 nmol/kg) administration group was significantly lower than that in the BG121 (30 nmol/kg) administration group and the solvent control group (FIG. 6).

3.5 Effects of BG121 and BG128 on Serum Insulin in db/db Mice

Figure 7:
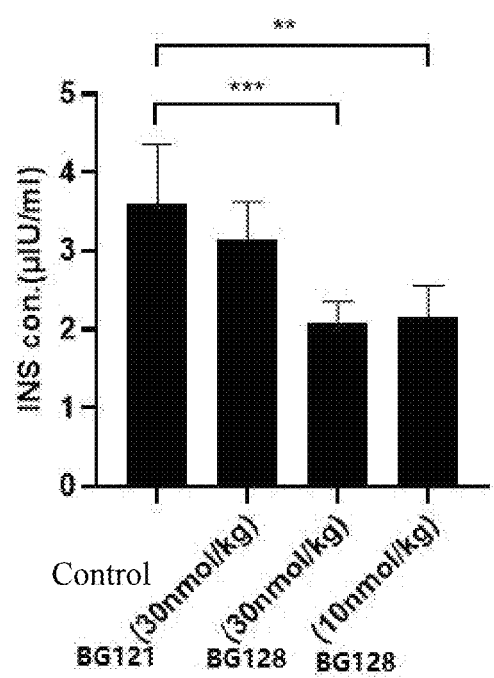
FIG. 7 shows the insulin contents determined in the db/db mice subcutaneously injected with BG121 (30 nmol/kg), BG128 (30 nmol/kg), BG128 (10 nmol/kg) and solvent control (Control) every 3 day on day 25 after first administration; ***, $P<0.001$, $P<0.01$.

According to the experimental method, after 25 days of administration, the insulin content in the mouse serum was determined. The results showed that 25 days after administration, the insulin contents in the serum of the mice in the BG128 (30 nmol/kg) and BG128 (10 nmol/kg) administration groups were significantly lower than that in the solvent control group in a dose dependent manner; while there was no significant difference in the insulin contents between the BG121 (30 nmol/kg) administration group and the solvent control group (FIG. 7). On the one hand, the experiment proved that the compound of the present disclosure does not affect the secretion of insulin when lowering blood sugar, and also confirms that compared with BG121, BG128 has a better effect on insulin when lowering blood sugar.

Experimental Example 3: Test of the Inhibitory Effect of BG128 on Hyperglycemia in db/db Mice 1. Experiment Materials 1.1 Experiment Animals 55 6-8 week-old SPF-grade male db/db mice were purchased from Zhejiang Vital River Experimental Animal Technology Co., Ltd.

1.2 the Information of the Test Sample and Reference Sample is Shown in the Table Below

TABLE 6

Information of the test sample and reference sample

| Name | Test sample (BG128) | Control sample (Tirzepatide, BG121) |
|---|---|---|
| Content | 89.8% | 87.42% |
| Physical state | White solid | White solid |
| Preservation condition | Shading, sealing, storing at −20° C. or lower | Shading, sealing, storing at −20° C. or lower |
| Provider | BRIGHTGENE BIO-MEDICAL TECHNOLOGY CO., LTD. | BRIGHTGENE BIO-MEDICAL TECHNOLOGY CO., LTD. |

1.3 Formulation of the Test Sample and Reference Sample

According to the dosage regimen in Table 7, a certain amount of Tirzepatide and BG128 were weighed and the vehicle (pH=7.0, 20 mM sodium citrate buffer) was added to formulated to the corresponding concentration. The formulation was performed once every 7 days, and the formulated mixture was sub-packaged and stored at 2° C.-8° C. in the dark.

2. Experimental Method 2.1 Experiment Grouping

Before the administration, according to the body weight and fasting blood glucose, the animals were grouped into: db/db-ND group, Tirzepatide—0.15 mg/kg group, BG128—0.05 mg/kg group, BG128—0.15 mg/kg group and BG128—0.5 mg/kg group, and each group have 11 animals; and see Table 7 for details.

2.2 Administration Regimen

The day of the first administration was recorded as d1, and the time was recorded by analogy; Tirzepatide and BG128 were administered once every three days, and the time points were d1, d4, d7, d10, d13, d16, d19, d22, d25 and d28, a total of 10 administrations; and see Table 7 for details.

TABLE 7

Experiment grouping and administration regimen

| Grouping | Number | CPD | Administration regimen | Administration time point |
|---|---|---|---|---|
| Group-1 | 11 | Vehicle | Subcutaneous administration at 10 mL/kg mg/kg | d1, d4, d7, d10, d13, d16, d19, d22, d25 and d28 |
| Group-2 | 11 | Tirzepatide | Subcutaneous administration at 10 mL/kg or 0.15 mg/kg | |
| Group-3 | 11 | BG128 | Subcutaneous administration at 10 mL/kg or 0.05 mg/kg | |
| Group-4 | 11 | BG128 | Subcutaneous administration at 10 mL/kg or 0.15 mg/kg | |
| Group-5 | 11 | BG128 | Subcutaneous administration at 10 mL/kg or 0.5 mg/kg | |

2.3 Test Indicators

Weighing: animals were weighed before administration once every three days until the end of the experiment.

2.3.1 Food Intake of Animal

The food intake of the animals was recorded starting at three days before the grouping for administration until the end of the experiment. The remaining amount was weighed before administration each time.

2.3.2 Blood Sugar of Animal

1) Non-fasting blood glucose determination: first administration 0 h (pre), 1 h, 2 h, 3 h, 6 h, 24 h, 48 h, 72 h;

2) Fasting blood glucose: the determination dates were respectively d-1 (before grouping), d7, d13, d19, d25 and d31. The animals were fasted for 6 hours, and the fasting blood glucose was determined before administration.

2.3.3 Blood Biochemical Determination 3 days after the last administration, the animals were weighed and fasted for 6 hours, and the fasting blood glucose of the animals was determined; after anesthesia, a portion of non-anticoagulated whole blood was collected through the orbital venous plexus, stood at room temperature for 30 minutes, and centrifuged at 5000 rpm for 5 minutes, the serum was separated and frozen at −80° C. for the determination of serum insulin content; a portion of anticoagulated whole blood was collected for the determination of HbA1c content. The serum insulin was determined by Elisa method.

2.4 Data Analysis

The data was organized in Excel 2017 and Prism6.0, and the data was expressed as Mean±SEM (standard error). One-way ANOVA was used for analysis, and Tukey was selected as the analysis method for comparing significance of difference between groups; when the two groups were compared, T-test was used for two-tailed test between the two groups. When $p<0.05$, there was a significant difference between the two groups, and when there are a small number of determination data within the group that have large differences, GraphPad Prism6.0 can be used to analyze the data to identify outliters and eliminate the values with large differences.

3. Results 3.1 Body Weight and Body Weight Growth Rate

The results of changes in animal body weight and body weight growth rate (FIG. 8 and FIG. 9) showed: during the first administration, the body weight of the animals in each administration group showed a trend of significant decrease, and the body weight decrease in the groups administered with different doses of BG128 was positively correlated with the administration dose; and after day 3, the body weight of the animals in each administration group returned to a steady increase. In the later stage of administration, there was no significant difference in the weight changes of the animals in each group ($p>0.05$).

Figure 8:
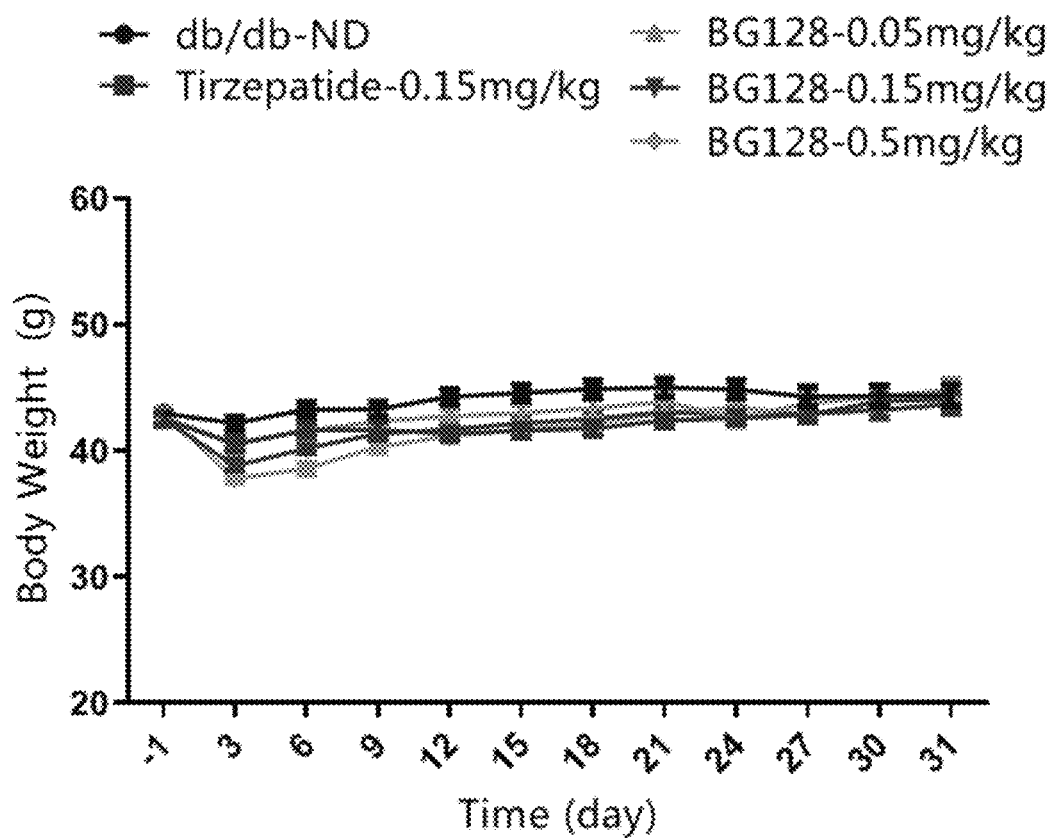
FIG. 8 shows the changes in the body weight of the animals in db/db-ND group, Tirzepatide—0.15 mg/kg group, BG128—0.05 mg/kg group, BG128—0.15 mg/kg group and BG128—0.5 mg/kg group during the experiment.
Figure 9:
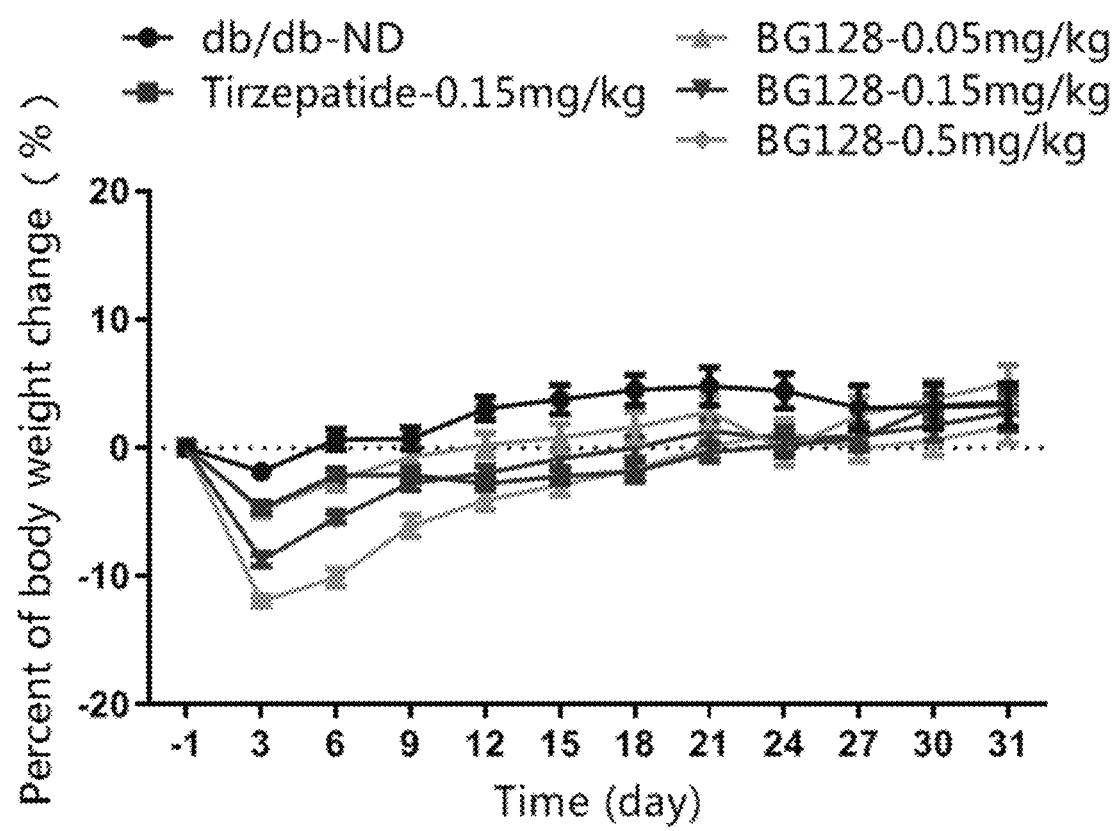
FIG. 9 shows the changes in body weight growth rates of the animals in db/db-ND group, Tirzepatide—0.15 mg/kg group, BG128—0.05 mg/kg group, BG128—0.15 mg/kg group and BG128—0.5 mg/kg group.

It can be seen from FIG. 8 and FIG. 9 that at the equal dose, the animal body weight loss rate of BG128 administration group was better than that of Tirzepatide administration group, that is, the efficacy of BG128 was better than that of the positive control Tirzepatide.

3.2 Food Intake

The results of changes in animal food intake (FIG. 10) showed: compared with the db/db-ND group, the food intake of the animals in each administration group was decreased significantly after the first administration, and the food intake decrease in the groups administered with different doses of BG128 was positively correlated with the administration dose; and after d4, the food intake of the animals in each administration group returned to increase, fluctuated up and down within a small range, and remained relatively stable.

Figure 10:
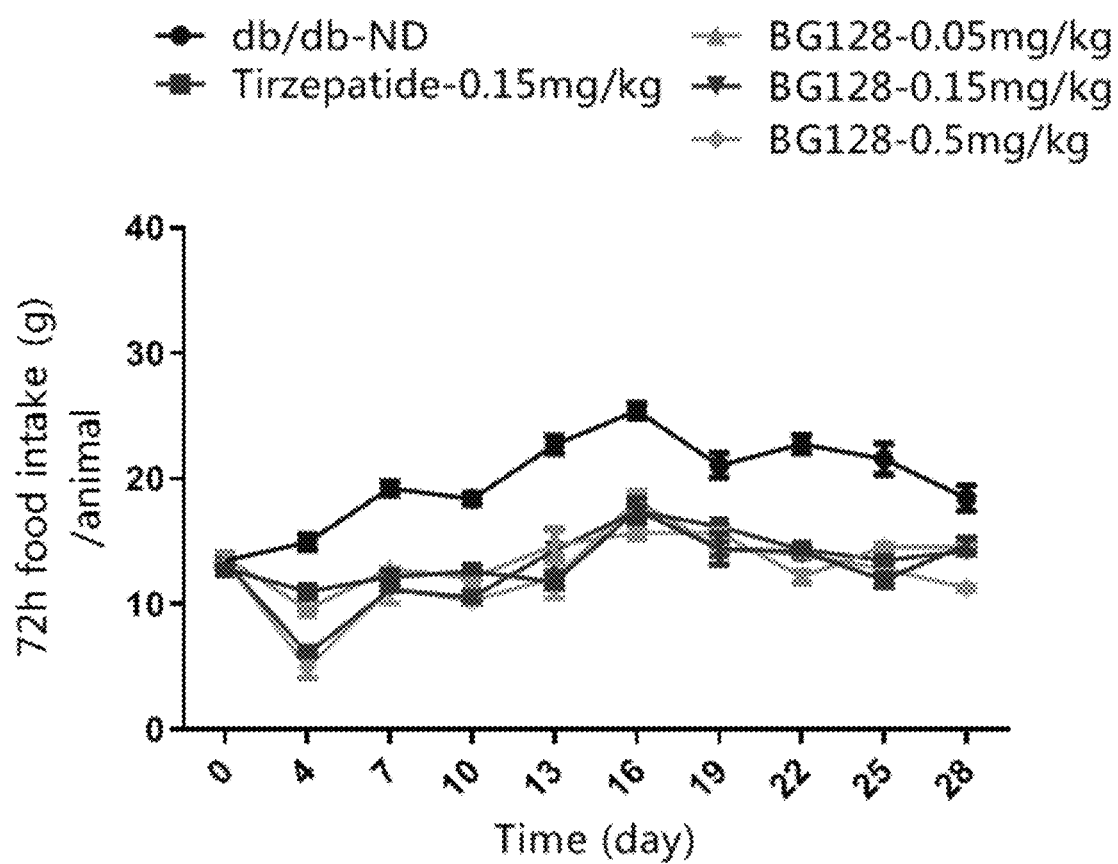
FIG. 10 shows the changes in the food intake of the animals in db/db-ND group, Tirzepatide—0.15 mg/kg group, BG128—0.05 mg/kg group, BG128—0.15 mg/kg group and BG128—0.5 mg/kg group.

It can be seen from FIG. 10 that at the equal dose, the decrease in food intake of the BG128 administration group was significantly greater than that of the positive control group Tirzepatide.

3.3 Non-Fasting Blood Glucose after the First Administration

Figure 11:
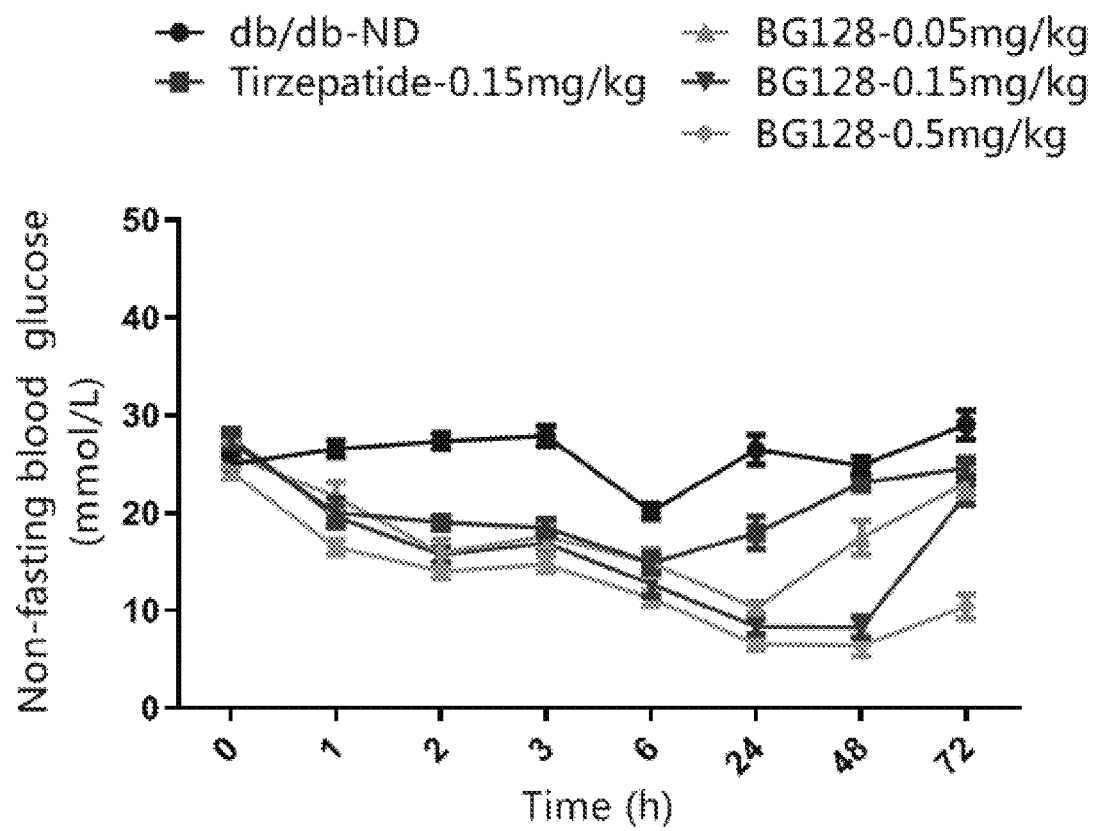
FIG. 11 shows the changes in the non-fasting blood glucose of the animals in db/db-ND group, Tirzepatide—0.15 mg/kg group, BG128—0.05 mg/kg group, BG128—0.15 mg/kg group and BG128—0.5 mg/kg group.

The monitoring results of non-fasting blood glucose of animals (FIG. 11) showed: after the first administration, the non-fasting blood glucose of the animals in the positive drug Tirzepatide—0.15 mg/kg administration group was decreased rapidly within 6 hours after the first administration, and gradually recovered to increase within 6-72 h; the non-fasting blood glucose of the animals in the BG128 administration group was decreased rapidly within 24 h after the first administration, the non-fasting blood glucose of the animals in the low-dose group (0.05 mg/kg) and the middle-dose group (0.15 mg/kg) was gradually recovered to increase within 24 h-72 h after administration, and the non-fasting blood glucose of the animals in high-dose group (0.5 mg/kg) was maintained in a relatively low range within 24 h-72 h after administration; and compared with the db/db-ND group, the Tirzepatide—0.15 mg/kg group and the each dose group of BG128 showed significant blood sugar suppression effect within 72 h of the first administration, and the blood sugar suppression effect of BG128 was dose-dependent and better than that of positive drug Tirzepatide—0.15 mg/kg group at an equal dose.

3.4 Fasting Blood Glucose

Figure 12:
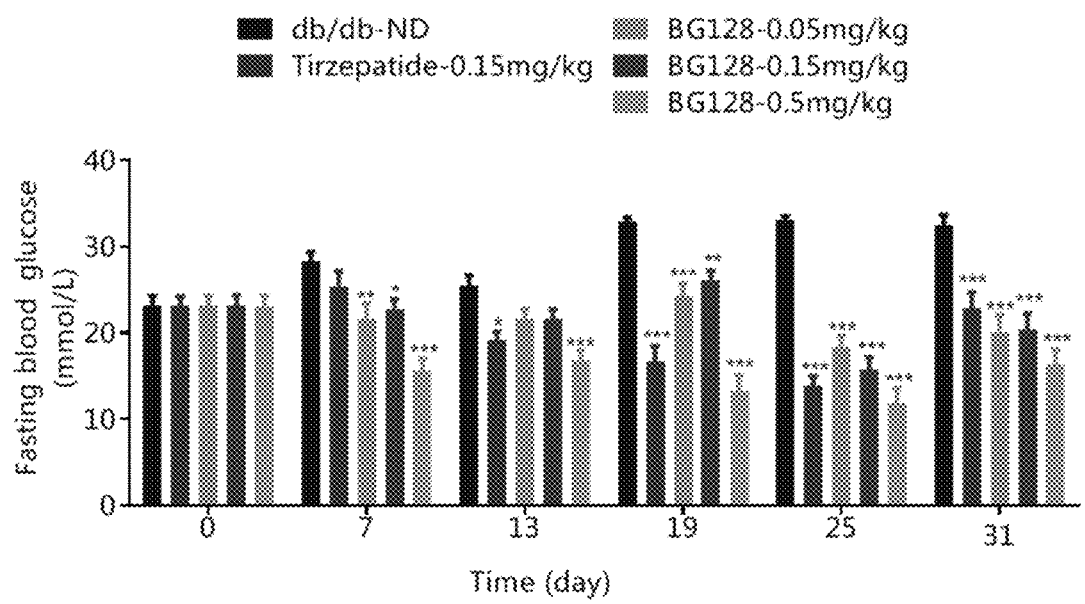
FIG. 12 shows the changes in the fasting blood glucose of the animals in db/db-ND group, Tirzepatide—0.15 mg/kg group, BG128—0.05 mg/kg group, BG128—0.15 mg/kg group and BG128—0.5 mg/kg group; Two-way ANOVA: *$p<0.001$ vs. db/db-ND group; $p<0.01$ vs. db/db-ND group; *$p<0.05$ vs. db/db-ND group; and in FIG. 12, the histograms shown at each time point of 0 day, 7 days, 13 days, 19 days, 25 days, and 31 days sequentially represent b/db-ND group, Tirzepatide—0.15 mg/kg group, BG128—0.05 mg/kg group, BG128—0.15 mg/kg group and BG128—0.5 mg/kg group from left to right.

The monitoring results of fasting blood glucose of animals (FIG. 12 and Table 8) showed: compared with db/db-ND group, the fasting blood glucose of the animals in Tirzepatide—0.15 mg/kg group and each dose group of BG128 was significantly decreased at different periods of administration (p<0.05); and at the end of the experiment, the fasting blood glucose of each dose group of BG128 was significantly decreased compared with that of the db/db-ND group in a dose dependent manner. The high-dose BG128 group has a better effect on suppressing blood sugar than the positive drug Tirzepatide—0.15 mg/kg group.

TABLE 8

Change in fasting blood glucose of animals (mmol/L) (Mean ± SD)

| Group | Number | Day 0 (n = 11) | Day 7 (n = 11) | Day 13 (n = 11) | Day 19 (n = 11) | Day 25 (n = 11) | Day 31 (n = 11) |
|---|---|---|---|---|---|---|---|
| db/db-ND | 11 | 23.15 ± 1.14 | 28.30 ± 1.07 | 25.49 ± 1.18 | 32.93 ± 0.41 | 33.04 ± 0.50 | 32.46 ± 1.20 |
| Tirzepatide 0.15 mg/kg | 11 | 23.16 ± 1.10 | 25.39 ± 1.75 | 19.12 ± 1.02$^a$ | 16.65 ± 1.82$^c$ | 13.86 ± 1.12$^c$ | 22.85 ± 1.86$^c$ |
| BG128 0.05 mg/kg | 11 | 23.18 ± 1.15 | 21.68 ± 1.77$^b$ | 21.68 ± 1.11 | 24.30 ± 1.41$^c$ | 18.32 ± 1.37$^c$ | 20.15 ± 1.91$^c$ |
| BG128 0.15 mg/kg | 11 | 23.17 ± 1.19 | 22.78 ± 1.11$^a$ | 21.58 ± 1.13 | 26.14 ± 1.05$^b$ | 15.70 ± 1.50$^c$ | 20.38 ± 1.87$^c$ |
| BG128 0.5 mg/kg | 11 | 22.99 ± 1.35 | 15.54 ± 1.49$^c$ | 16.79 ± 1.20$^c$ | 13.26 ± 1.91$^c$ | 11.85 ± 1.74$^c$ | 16.41 ± 1.68$^c$ |

$^a$*p < 0.05 vs. db/db-ND, by Two way-ANOVA, Tukey's test
$^b$**p < 0.01 vs. db/db-ND, by Two way-ANOVA, Tukey's test
$^c$***p < 0.001 vs. db/db-ND, by Two way-ANOVA, Tukey's test 3.5 Serum Insulin The determination results of animal serum insulin (FIG. 13 and Table 9) showed: serum insulin concentrations of the animals in the Tirzepatide—0.15 mg/kg group and each dose group of BG128 were decreased, and the serum insulin of each dose group of BG128 has a statistically significant decrease compared with the model group (p= or <0.05).

Figure 13:
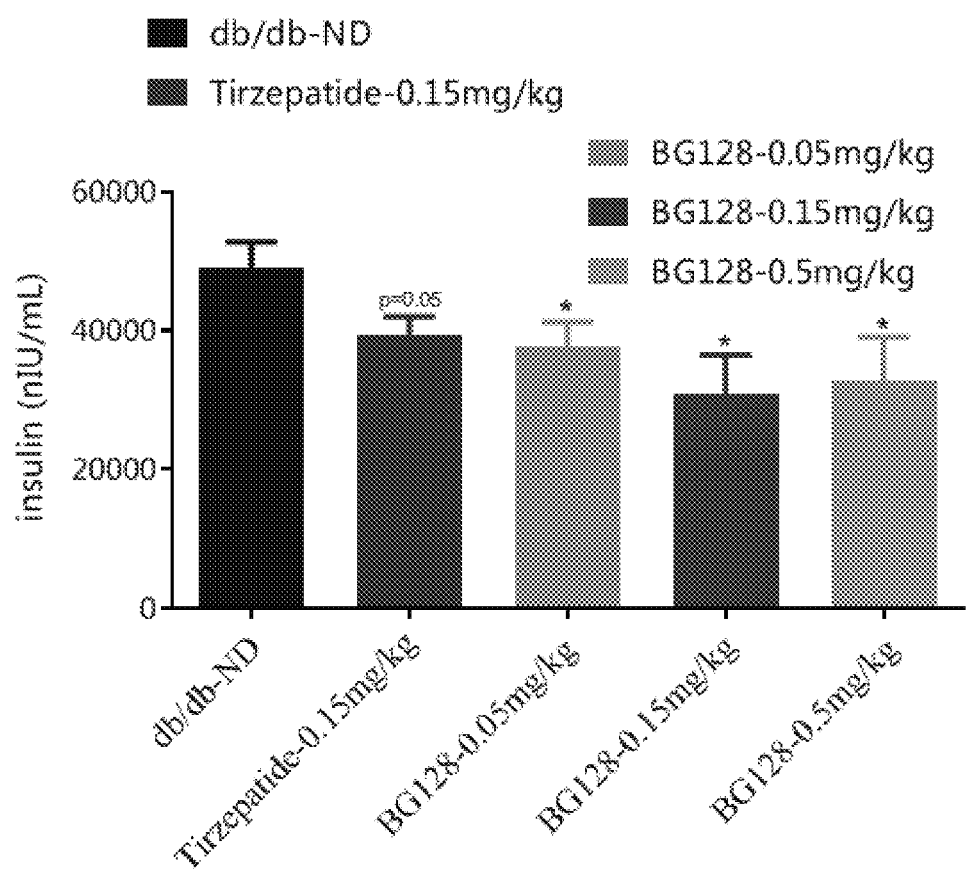
FIG. 13 shows the changes in the serum insulin concentrations of the animals in db/db-ND group, Tirzepatide—0.15 mg/kg group, BG128—0.05 mg/kg group, BG128—0.15 mg/kg group and BG128—0.5 mg/kg group; T-test: *$p<0.05$ vs. db/db-ND group.

It can be seen from FIG. 13 that the decrease of serum insulin concentration of the BG128 group was significantly greater than that of the Tirzepatide—0.15 mg/kg group at an equal dose.

TABLE 9

Insulin change in serum (nIU/mL) (Mean ± SD)

| Group | db/db-ND (n = 11) | Tirzepatide-0.15 mg/kg (n = 11) | BG128-0.05 mg/kg (n = 11) | BG128-0.15 mg/kg (n = 11) | BG128-0.5 mg/kg (n = 11) |
|---|---|---|---|---|---|
| Insulin (nIU/mL) | 48991.0 ± 3768.0 | 39227.0 ± 2788.0 | 37649.0 ± 3597.0$^a$ | 30897.0 ± 5634.0$^a$ | 32774.0 ± 6290.0$^a$ |

$^a$*p < 0.05 vs. db/db-ND, by T-test analysis 3.6 Whole Blood HbA1C Percentage (%)

Figure 14:
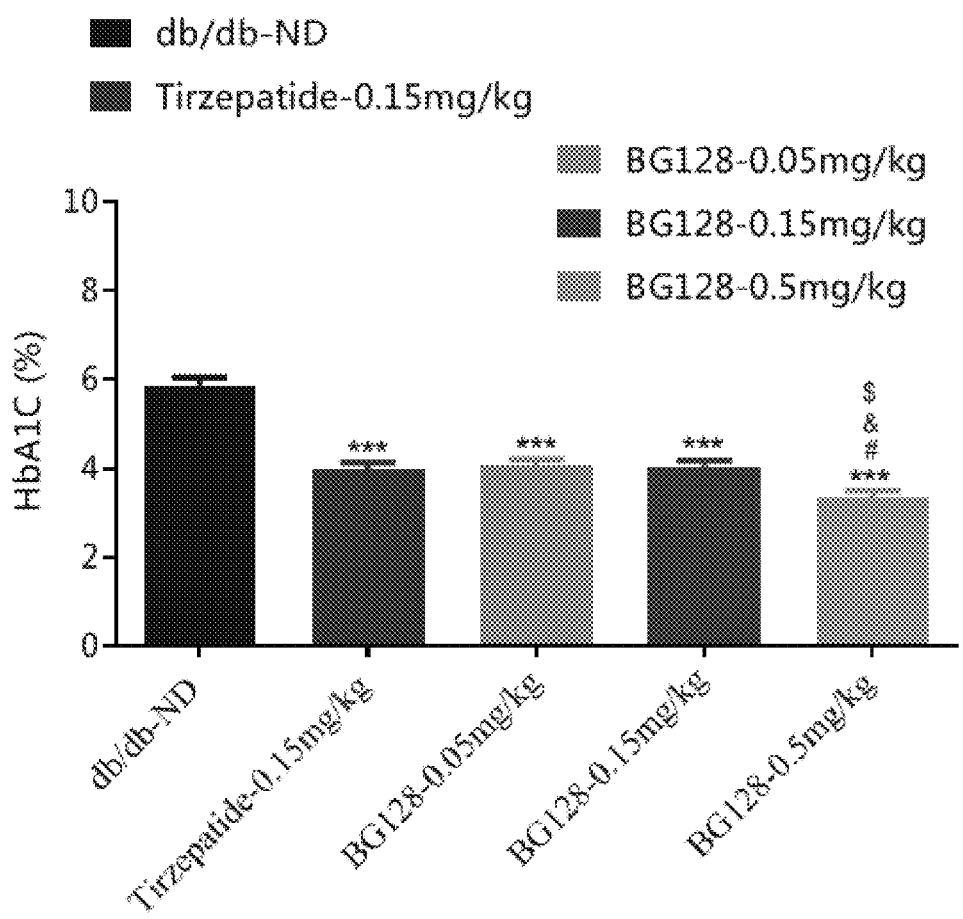
FIG. 14 shows the percentage of HbA1C in the anticoagulated whole blood of the animals in db/db-ND group, Tirzepatide—0.15 mg/kg group, BG128—0.05 mg/kg group, BG128—0.15 mg/kg group and BG128—0.5 mg/kg group; One-way ANOVA: ***$p<0.001$ vs. db/db-ND group; #$p<0.05$ vs. Tirzepatide—0.15 mg/kg; &$p<0.05$ vs. BG128—0.05 mg/kg; \$$p<0.05$ vs. BG128—0.15 mg/kg.

The results of whole blood HbA1C % (FIG. 14 and Table 10) showed: compared with the db/db-ND group, the HbA1C percentages in the anticoagulated whole blood of the animals in the Tirzepatide—0.15 mg/kg group and each dose group of BG128 were significantly decreased (p<0.001), HbA1C % in the anticoagulated whole blood of the Tirzepatide—0.15 mg/kg group, BG128—0.05 mg/kg group, BG128—0.15 mg/kg group and BG128—0.5 mg/kg group was decreased by 1.88%, 1.80%, 1.83% and 2.54%, respectively in a dose dependent manner.

Figure 15:
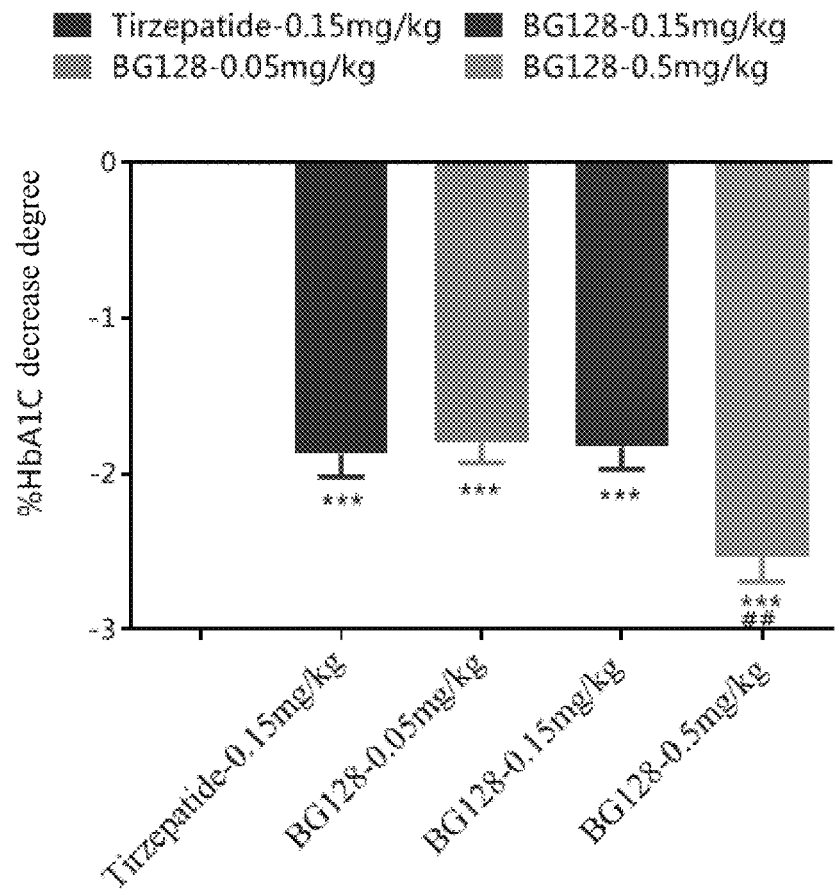
FIG. 15 shows the HbA1C percentage reduction results of the animals in Tirzepatide—0.15 mg/kg group, BG128—0.05 mg/kg group, BG128—0.15 mg/kg group and BG128—0.5 mg/kg group compared with the model group; One-way ANOVA: ***$p<0.001$ vs. db/db-ND group, ##$p<0.001$ vs. Tirzepatide—0.15 mg/kg.

It can be seen from FIG. 15 that the effects of the BG128 group and the Tirzepatide group at an equal dose are comparable. The decrease in the high-dose BG128 group was significantly greater than that in the Tirzepatide—0.15 mg/kg group and the BG128—0.15 mg/kg group (p<0.01).

TABLE 10

Change in glycosylated hemoglobin (Mean ± SEM)

| Group | db/db-ND (n = 11) | Tirzepatide- 0.15 mg/kg (n = 11) | BG128-0.05 mg/kg (n = 11) | BG128-0.15 mg/kg (n = 11) | BG128-0.5 mg/kg (n = 11) |
|---|---|---|---|---|---|
| Hb | 134.40 ± 1.46 | 129.30 ± 1.38 | 128.10 ± 5.30 | 131.60 ± 1.23 | 140.80 ± 2.02* |
| HbA1C | 7.87 ± 0.24 | 5.16 ± 0.19*** | 5.18 ± 0.23*** | 5.31 ± 0.19*** | 4.68 ± 0.20*** |
| HbA1C% | 5.87 ± 0.18 | 3.99 ± 0.14$^a$ | 4.07 ± 0.13$^a$ | 4.04 ± 0.14$^a$ | 3.33 ± 0.16$^{abde}$ |
| % HbA1C decrease | NA | 1.88% ± 0.14$^a$ | 1.80% ± 0.13$^a$ | 1.83% ± 0.14$^a$ | 2.54% ± 0.16$^{ab}$ |

$^{a}$*** $p < 0.001$ vs. db/db-ND, by One-way ANOVA, Tukey's test
$^{b}$# $p < 0.05$ vs. Tirzepatide-0.15 mg/kg, by One-way ANOVA, Tukey's test
$^{c}$## $p < 0.01$ vs. Tirzepatide-0.15 mg/kg, by One-way ANOVA, Tukey's test
$^{d}$& $p < 0.05$ vs. BG128-0.05 mg/kg, by One-way ANOVA, Tukey's test
$^{e}$$ $p < 0.05$ vs. BG128-0.15 mg/kg, by One-way ANOVA, Tukey's test 4. Conclusion db/db mice are derived from autosomal recessive inheritance of C57BL/KsJ inbred strain, and belong to type II diabetes model animals. Under the conditions of the present experiment, the blood glucose of the animals before grouping was greater than 16.7 mmol/L, and treatment with the positive control Tirzepatide can significantly inhibit hyperglycemia in db/db mice, and reduce the insulin and glycosylated hemoglobin contents in peripheral blood, indicating that the model is stable and reliable.

BG128 can cause acute decreases in body weight and food intake of db/db mice, which can remain relatively stable after administration. BG128 can significantly reduce the non-fasting blood glucose after the first administration, and the efficacy of BG128 is better than that of Tirzepatide at an equal dose, and BG128 can significantly inhibit fasting blood glucose of db/db mice and reduce insulin and glycosylated hemoglobin contents in peripheral blood.

Experimental Example 4: Test of the Pharmacodynamic Effect of BG128 on C57BL/6 Mouse Model Having STZ-HFD Feed-Induced Diabetes Combined NASH 1. Experiment Materials 1.1 the Information of the Test Sample and Reference Sample is Shown in the Table 11 Below

TABLE 11

Information of the test sample and reference sample

| Name | Test sample (BG128) | Control sample (Tirzepatide) |
|---|---|---|
| Content | 79.0% | 87.4% |
| Physical state | White solid | White solid |
| Preservation condition | Shading, sealing, storing at −20° C. or lower | Shading, sealing, storing at −20° C. or lower |
| Provider | BRIGHTGENE BIO-MEDICAL TECHNOLOGY CO., LTD. | BRIGHTGENE BIO-MEDICAL TECHNOLOGY CO., LTD. |

1.2 Formulation of the Test Sample and Reference Sample

According to the dosage regimen, a certain amount of Tirzepatide and BG128 were weighed and the vehicle (pH=7.0, 20 mM sodium citrate buffer) was added to formulated to the corresponding concentration.

1.3 Experiment System 1.3.1 Experiment Animal Information

Germline: C57BL/6
Grade: SPF level
Number and gender: 30 pregnant female mice
Supplier: Shanghai Jihui Laboratory Animal Care Co., Ltd.

1.3.2 Animal Feeding Management

Animals were kept in the barrier system, the environmental conditions in the animal room were controlled as room temperature of 20° C.-26° C. and humidity of 40%-70%, and the breeders recorded once every morning and afternoon. Free drinking and normal feeding.

2. Experiment Design 2.1 Modeling Method

Newborn male mice were subcutaneously injected with STZ (100 μg/mouse) within 48 h of birth and fed by the female mice for four weeks, then the fasting blood glucose of the male mice was determined. By using the fasting blood glucose level greater than or equal to 12 mmol/L as the standard, 65 diabetic male mice were selected as the experimental animals, and fed with HFD feed for 8 weeks to establish a male C57BL/6 mouse model having STZ+HFD-induced diabetes combined with NASH.

2.2 Experiment Grouping 10 newborn male mice were selected, without STZ injection, and fed by the female mice for four weeks. The male mice were separated into cages and fed with normal maintenance feed and used as the normal control group; other mice were fed with HFD feed for one week, the fasting blood glucose of the animals was determined, and according to the fasting blood glucose and body weight, the animals were randomly grouped into: normal control group, model group, Tirzepatide—0.15 mg/kg group, BG128—0.05 mg/kg group, BG128—0.15 mg/kg group, and BG128—0.5 mg/kg group, and see Table 12 for details.

2.3 Administration Regimen

Administration began on the first day of week 2 of HFD feed feeding, and the experiment was ended after 7 weeks of continuous administration. The specific administration regimen is shown in Table 12.

TABLE 12

Experiment grouping and administration regimen

| Grouping | Number | STZ + HFD | Compound | Administration regimen |
|---|---|---|---|---|
| Group-1 | 10 | NO | Vehicle | Subcutaneous administration at 10 mL/kg, once every three days |
| Group-2 | 13 | Yes | Vehicle | Subcutaneous administration at 10 mL/kg, once every three days |
| Group-3 | 13 | Yes | Tirzepatide | Subcutaneous administration at 10 mL/kg or 0.15 mg/kg, once every three days |
| Group-4 | 13 | Yes | BG128 | Subcutaneous administration at 10 mL/kg or 0.05 mg/kg, once every three days |
| Group-5 | 13 | Yes | BG128 | Subcutaneous administration at 10 mL/kg or 0.15 mg/kg, once every three days |
| Group-6 | 13 | Yes | BG128 | Subcutaneous administration at 10 mL/kg or 0.5 mg/kg, once every three days |

2.4 Test Indicators 2.4.1 General Observation

Observation was performed at the start of the experiment once a day until the end of the experiment.

Observation content: the animal's death or dying, mental state, behavioral activity, feces property, feeding, drinking conditions and the like were observed at the side of the cage.

2.4.2 Animal Body Weight

The animals were weighed once every three days from the time of feeding with HFD feed until the end of the experiment.

2.4.3 Food Intake of Animal

The food intake of the animals was recorded from the time of feeding with HFD feed until the end of the experiment. The remaining amount was weighed before administration each time.

2.4.4 Animal Fasting Blood Glucose

The fasting blood glucose was determined using the Roche blood glucose meter after 4 weeks of breast-feeding by the female mouse (that is, before HFD feeding), before administration, and 1 week, 2 weeks, 3 weeks, 4 weeks, 5 weeks, 6 weeks and 7 weeks after administration and at the end point of experiment.

2.4.5 Clinical Biochemical Determination 3 days after the last administration, the animals were weighed and fasted for 6 hours; all experimental animals were anesthetized by intraperitoneal injection of pentobarbital sodium, non-anticoagulated whole blood was collected through the orbital venous plexus, stood at room temperature for 30 minutes, and centrifuged at 5000 rpm for 5 minutes, the serum was separated and frozen at −80° C. for the biochemical determination; and EDTA-K2 anticoagulated whole blood was collected through the orbital venous plexus and placed on wet ice for the determination of HbA1C content.

The serum sample was taken from −80° C., and the contents of ALT, AST, TG, TC, HDL-c and LDL-c in serum and HbA1C in whole blood were determined by Hitachi 7060 automatic biochemical detector, and the content of insulin was determined by enzyme-linked immunosorbent assay kit. The determination parameters are shown in Table 13 below:

TABLE 13

| Parameter | Unit |
|---|---|
| Alanine aminotransferase (ALT) | U/L |
| Aspartate aminotransferase (AST) | U/L |
| Triglyceride (TG) | mmol/L |
| Total cholesterol (TC) | mmol/L |
| High-density lipoprotein (HDL-c) | mmol/L |
| Low-density lipoprotein (LDL-c) | mmol/L |
| Glycosylated hemoglobin (HbA1C) | % |
| Insulin | nIU/ml |

2.4.6 Liver NAS Analysis

The mice were dissected according to procedure. After perfusion with pre-cooled normal saline, the liver was taken, photographed, weighed, soaked in 10% formalin and fixed for pathological HE staining. Liver paraffin sections of all animals were stained with HE according to KCI pathological staining standard SOP. All the stained sections were panoramically scanned by NanoZoomer Digital Pathology (S210, Hamamaci, Japan) scanner, and then observed at different magnifications by selecting different fields of view. Different liver lobules in the sections were scored and the scoring criteria are shown in Table 14.

TABLE 14

NAS scoring criteria for nonalcoholic steatohepatitis

| Pathological finding | Evaluation criteria | Score |
|---|---|---|
| Liver cell swelling | None | 0 |
|  | Small amount of cell swelling | 1 |
|  | Large amount of cell swelling | 2 |
| Inflammation within liver lobule: | None | 0 |
| Inflammatory foci | <2 inflammatory foci/200x field of view | 1 |
|  | 2-4 inflammatory foci/200x field of view | 2 |
|  | >4 inflammatory foci/200x field of view | 3 |

TABLE 14-continued

NAS scoring criteria for nonalcoholic steatohepatitis

| Pathological finding | Evaluation criteria | Score |
|---|---|---|
| Hepatic steatosis: Area occupied in the whole slice | <5% | 0 |
| | 5%-33% | 1 |
| | >33%-66% | 2 |
| | >66% | 3 |
| Pathological diagnosis basis | | Total score (NAS) |
| NASH or at risk of developing NASH | | >5 |
| Suspected NASH | | 3-4 |
| Non-NASH | | <2 |

2.4.7 Liver Fibrosis Analysis

The mice were dissected according to procedure. After perfusion with pre-cooled normal saline, the liver was taken, photographed, weighed, soaked in 10% formalin and fixed for pathological sirius red (SR) staining. Liver paraffin sections were stained with SR according to KCI pathological staining standard SOP. All the stained sections were panoramically scanned by NanoZoomer Digital Pathology (S210, Hamamaci, Japan) scanner, and the area of liver fibrosis was analyzed on the panoramically scanned SR stained sections by using VIS7.0 software to calculate the percentage of the area of liver fibrosis in the whole section area.

3. Data Analysis

The data was organized in Office Excel 2013 and GraphPad Prism6.0, and the data was expressed as Mean±SEM. One-way ANOVA and Two-way ANOVA were used for analysis, and test methods suitable for comparing significance of difference between groups, such as Tukey and Dunnett were selected as the analysis method; when the two groups were compared, T-test was used for two-tailed test between the two groups. When $p<0.05$, there was a significant difference between the two groups.

4. Results 4.1 Change in Animal Number

The NASH model animals created by STZ+HFD induction have a certain mortality rate. The clinical manifestations of the animals before death were white limbs and decreased activity, the manifestations are due to decreased blood circulation caused by metabolic disorders, are the normal performance of the model and are consistent with historical background data. The animals in the Tirzepatide—0.15 mg/kg, BG128—0.15 mg/kg and BG128—0.50 mg/kg groups have a good tolerance, indicating that the positive control Tirzepatide and BG128 have certain protective effects on the model animals. In the experiment design, 3 animals were added to each group (except the normal control group), and all animals that survived to the end of the experiment were included in the data statistics. The details are shown in Table 15.

TABLE 15

| | | | Number of animals | | | | |
|---|---|---|---|---|---|---|---|
| Grouping | Planned number | Enrolled number | Number at the end point | STZ + HFD | Compound | Number and date of animal deaths | Animal death cause |
| Group-1 | 10 | 10 | 10 | NO | Vehicle | 0 | — |
| Group-2 | 10 | 13 | 9 | Yes | Vehicle | 3 (Day 30, 42 and 45) | Model itself |
| Group-3 | 10 | 13 | 13 | Yes | Tirzepatide | 0 | — |
| Group-4 | 10 | 13 | 11 | Yes | BG128 | 2 (Day 45, 51) | Model itself |
| Group-5 | 10 | 13 | 13 | Yes | BG128 | 0 | — |
| Group-6 | 10 | 13 | 13 | Yes | BG128 | 0 | — |

Note:
—: Not applicable.

4.2 Animal Body Weight

Figure 16:
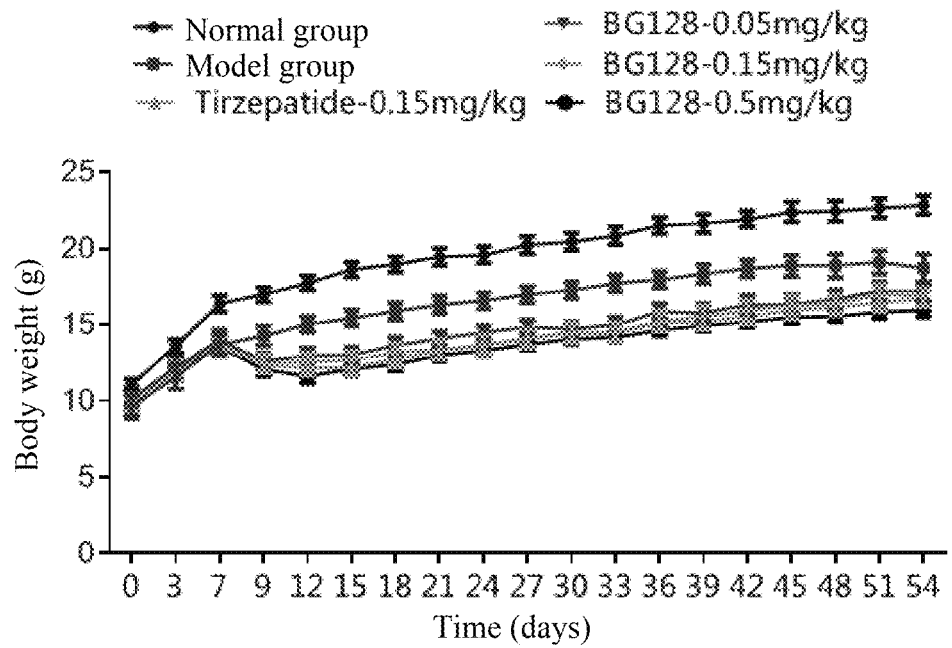
FIG. 16 shows the changes in the body weight of the animals in normal group, model group, Tirzepatide—0.15 mg/kg group, BG128—0.05 mg/kg group, BG128—0.15 mg/kg group and BG128—0.5 mg/kg group during the experiment.

The results of changes in animal body weight (FIG. 16) showed: after the first administration, the body weight of the animals in each administration group showed a trend of significant decrease, and the body weight decrease in the groups administered with different doses of BG128 was positively correlated with the administration dose; and after day 12, the body weight of the animals in each administration group returned to a steady increase, but were significantly lower than that in the model group overall. In the later stage of administration, there was no significant difference in the body weight changes of the animals in each administration group ($p>0.05$).

4.3 Food Intake

Figure 17:
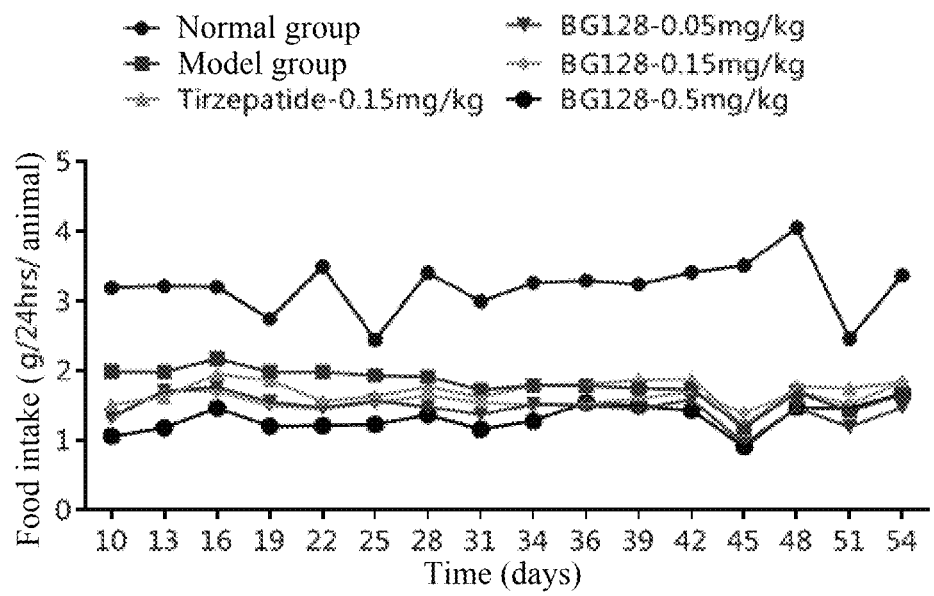
FIG. 17 shows the changes in the food intake of the animals in normal group, model group, Tirzepatide—0.15 mg/kg group, BG128—0.05 mg/kg group, BG128—0.15 mg/kg group and BG128—0.5 mg/kg group.

The results of changes in animal food intake (FIG. 17) showed: compared with the normal group, the food intake of the animals in each group to the high-fat feed was lower than the food intake of the animals in the normal group to the normal feed, and during the whole experiment period, there was no statistical difference in food intake between the model group and each administration group ($p>0.05$). It can be seen from FIG. 17 that the food intake of the BG128 administration animals in the group with the equal dose is lower than that of the Trizepatide administration animals in the group with the equal dose.

4.4 Fasting Blood Glucose

Figure 18:
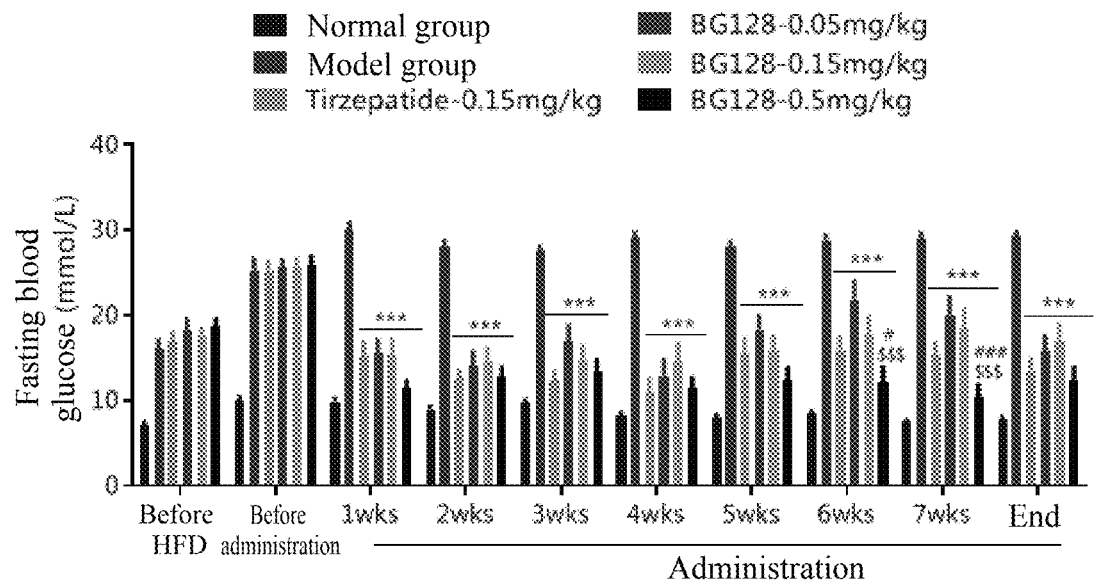
FIG. 18 shows the changes in the fasting blood glucose of the animals in normal group, model group, Tirzepatide—0.15 mg/kg group, BG128—0.05 mg/kg group, BG128—0.15 mg/kg group and BG128—0.5 mg/kg group; and in FIG. 18, the histograms shown at each time point of before HFD, before administration, 1 wks, 2 wks, 3 wks, 4 wks, 5 wks, 6 wks, 7 wks and end point sequentially represent normal group, model group, Tirzepatide—0.15 mg/kg group, BG128—0.05 mg/kg group, BG128—0.15 mg/kg group and BG128—0.5 mg/kg group from left to right.

The fasting blood glucose determination results of the animals showed: compared with the normal group, the fasting blood glucose of the model animals increased significantly before giving HFD; the blood glucose of the model animals after giving HFD for one week was significantly higher than that before HFD feeding; and from the beginning of administration to the end of the experiment, the fasting blood glucose of the animals in all administration groups was significantly lower compared with the model group (p<0.001) (Table 16 and FIG. 18). At the end of the experiment, the fasting blood glucose of each dose group of BG128 was significantly decreased compared with that of the db/db-ND group in a dose dependent manner. The effects of the BG128 group and the Tirzepatide group at an equal dose are comparable.

TABLE 16

Fasting blood glucose (mmol/L) (Mean ± SEM)

| Group | Normal control group | Model group | Tirzepatide 0.15 mg/kg | BG128 0.05 mg/kg | BG128 0.15 mg/kg | BG128 0.5 mg/kg |
|---|---|---|---|---|---|---|
| Number | n = 10 | n = 9 | n = 13 | n = 11 | n = 13 | n = 13 |
| Before HFD | 7.07 ± 0.37 | 15.90 ± 0.91 | 16.95 ± 0.98 | 18.28 ± 1.18 | 17.69 ± 0.81 | 18.59 ± 0.88 |
| Before administration | 10.02 ± 0.40 | 25.29 ± 1.01 | 25.33 ± 1.01 | 25.59 ± 0.91 | 25.71 ± 0.91 | 25.81 ± 1.08 |
| Administration for 1 week | 9.82 ± 0.39 | 29.43 ± 0.63 | 15.15 ± 1.63$^a$ | 15.62 ± 1.42$^a$ | 15.43 ± 1.66$^a$ | 11.39 ± 0.86$^a$ |
| Administration for 2 weeks | 8.98 ± 0.30 | 27.98 ± 0.46 | 12.58 ± 0.96$^a$ | 14.13 ± 1.61$^a$ | 14.61 ± 1.45$^a$ | 12.82 ± 1.12$^a$ |
| Administration for 3 weeks | 9.78 ± 0.26 | 27.42 ± 0.52 | 12.32 ± 1.07$^a$ | 16.89 ± 1.85$^a$ | 14.83 ± 1.49$^a$ | 13.35 ± 1.37$^a$ |
| Administration for 4 weeks | 8.14 ± 0.43 | 29.02 ± 0.46 | 11.08 ± 1.43$^a$ | 12.89 ± 1.83$^a$ | 14.52 ± 2.09$^a$ | 11.39 ± 1.20$^a$ |
| Administration for 5 weeks | 7.91 ± 0.31 | 27.67 ± 0.61 | 15.58 ± 1.58$^a$ | 18.32 ± 1.62$^a$ | 15.75 ± 1.81$^a$ | 12.31 ± 1.47$^a$ |
| Administration for 6 weeks | 8.47 ± 0.26 | 28.79 ± 0.56 | 15.90 ± 1.50$^a$ | 21.82 ± 2.11$^a$ | 17.88 ± 2.05$^a$ | 12.17 ± 1.70$^{abd}$ |
| Administration for 7 weeks | 7.50 ± 0.13 | 28.37 ± 0.61 | 15.49 ± 1.26$^a$ | 18.89 ± 1.89$^a$ | 17.26 ± 1.97$^a$ | 10.45 ± 1.34$^{acd}$ |
| Endpoint | 7.87 ± 0.21 | 29.31 ± 0.42 | 13.55 ± 1.25$^a$ | 15.81 ± 1.83$^a$ | 16.85 ± 2.04$^a$ | 12.27 ± 1.61$^a$ |

Figure 19:
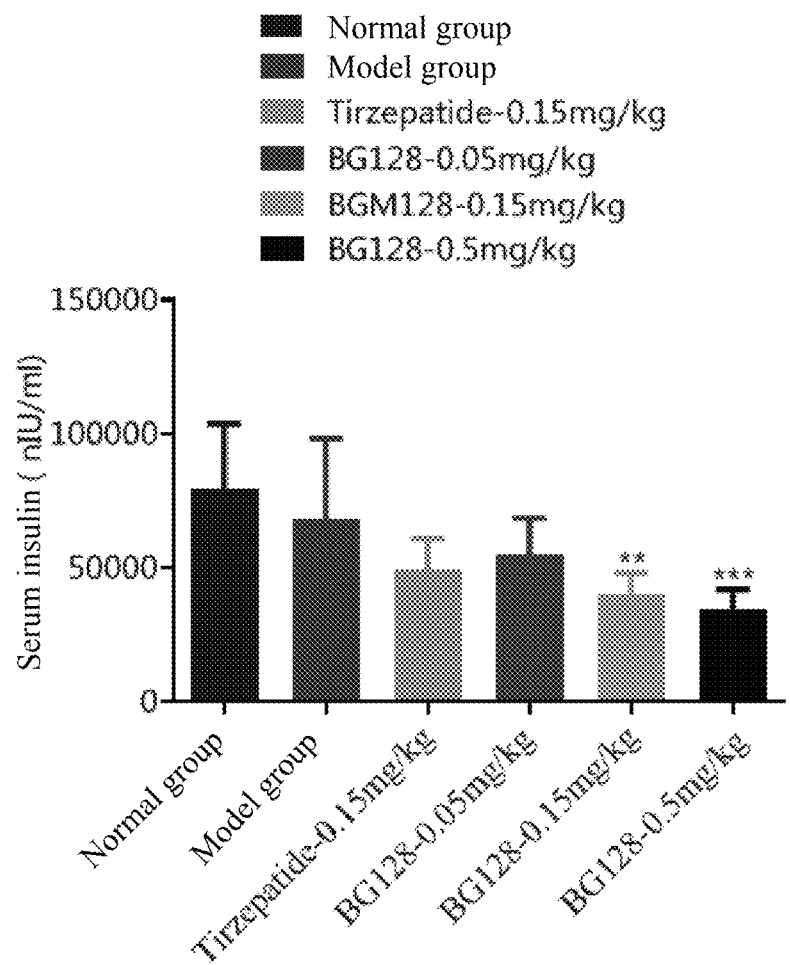
FIG. 19 shows the changes in the insulin of the animals in model group, Tirzepatide—0.15 mg/kg group, BG128—0.05 mg/kg group, BG128—0.15 mg/kg group and BG128—0.5 mg/kg group; One-Way ANOVA: $p<0.05$ vs. model group; *$p<0.001$ vs. model group.

$^a$***p < 0.001 vs. model group, by Two way-ANOVA, Tukey's test
$^b$#p < 0.05 vs. BG128-0.05 mg/kg, by Two way-ANOVA, Tukey's test
$^c$###p < 0.001 vs. BG128-0.05 mg/kg, by Two way-ANOVA, Tukey's test
$^d$$$$p < 0.001 vs. BG 128-0.15 mg/kg, by Two way-ANOVA, Tukey's test 4.5 Insulin The results of insulin changes (FIG. 19) showed that: serum insulin concentrations of the animals in the Tirzepatide—0.15 mg/kg group and each dose group of BG128 were decreased, and the serum insulin of the BG128—0.15 mg/kg and BG128—0.5 mg/kg groups was statistically significant compared with the db/db-NDJ group (p<0.05). The effect of the BG128 group was better than that of the Tirzepatide group at an equal dose.

4.6 HbA1C %

Figure 20:
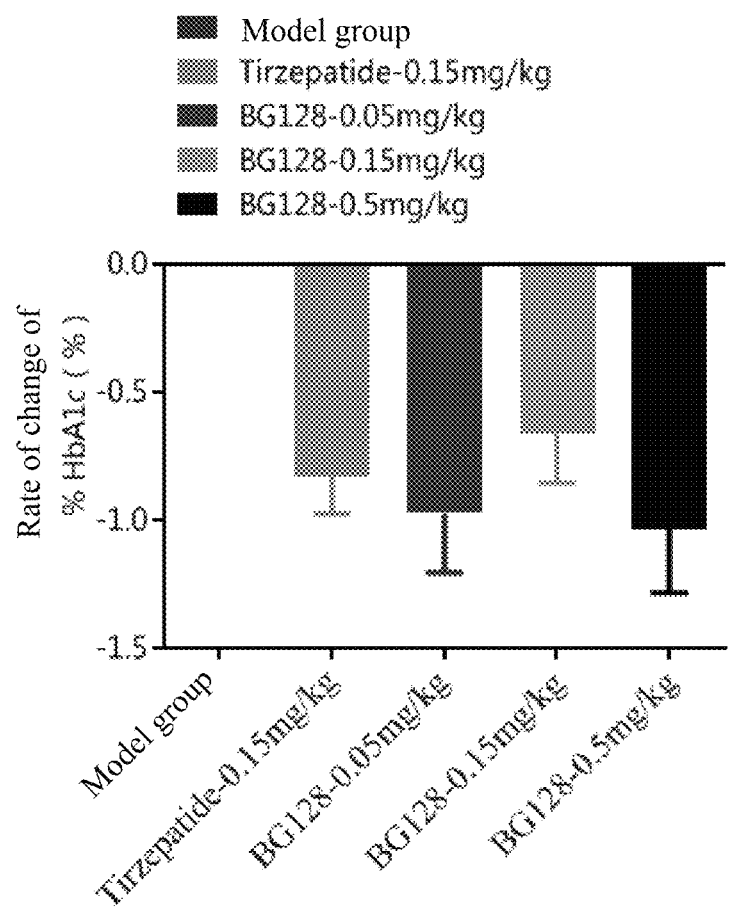
FIG. 20 shows the percent change in % HbA1C in the peripheral blood of the animals in model group, Tirzepatide—0.15 mg/kg group, BG128—0.05 mg/kg group, BG128—0.15 mg/kg group and BG128—0.5 mg/kg group; One-Way ANOVA: *$p<0.05$ vs. model group.

The result of the change in HbA1C %$_0$ in peripheral blood (Table 17) showed: after the administration, HbA1c % of the model group was increased significantly compared with that of the normal control group; HbA1c % of the Tirzepatide group and each dose group of BG128 was decreased to varying degrees and HbA1c % of the BG128—0.5 mg/kg group was significantly decreased compared with that of the model group (p<0.05); and taking the HbA1C % of the model group as the baseline value, HbA1c % of the Tirzepatide group and each dose group BG128 was decreased by 0.83%, 0.97%, 0.66% and 1.04%, respectively (FIG. 20). The effects of the BG128 group and the Tirzepatide group at an equal dose are comparable.

TABLE 17

Change in glycosylated hemoglobin (Mean ± SEM)

| Group | Normal control group | Model group | Tirzepatide 0.15 mg/kg | BG128 0.05 mg/kg | BG128 0.15 mg/kg | BG128 0.5 mg/kg |
|---|---|---|---|---|---|---|
| Number | n = 10 | n = 9 | n = 13 | n = 11 | n = 13 | n = 13 |
| % HbAC | 1.35 ± 0.03 | 1.97 ± 0.47 | 1.14 ± 0.14 | 1.00 ± 0.23 | 1.31 ± 0.19 | 0.94 ± 0.25$^a$ |
| Percentage of decrease in % HbAC | — | — | −0.83 ± 0.14 | −0.97 ± 0.23 | −0.66 ± 0.19 | −1.04 ± 0.25 |

Figure 21:
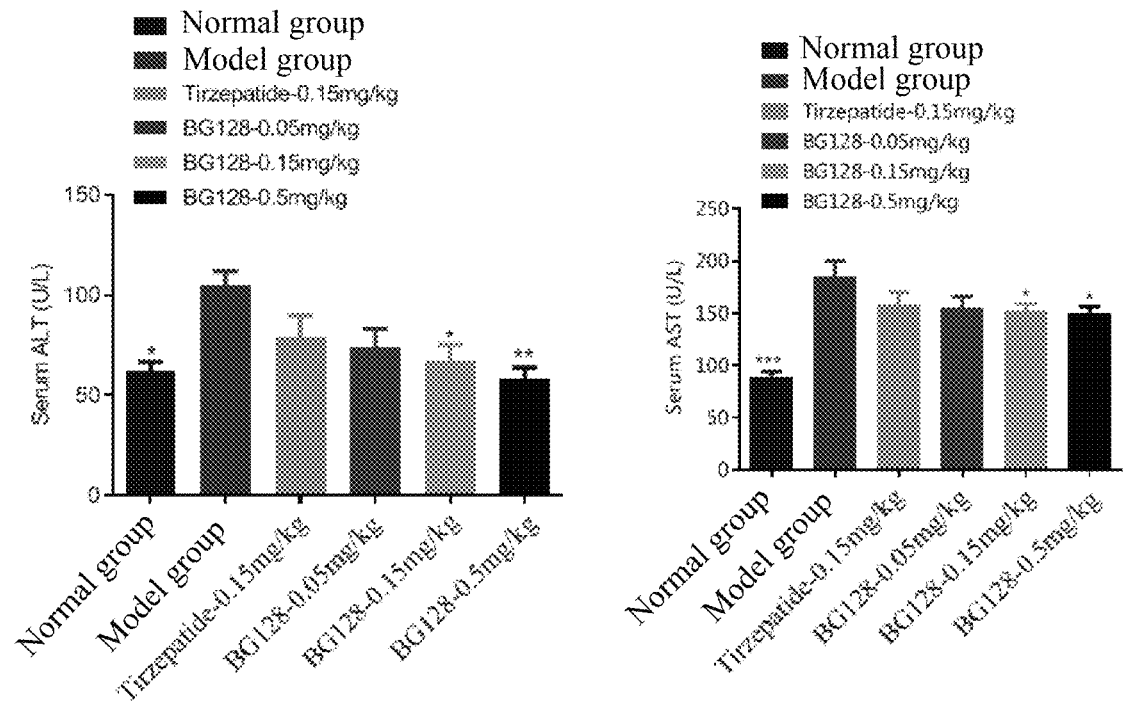
FIG. 21 shows the changes in the ALT and AST in the blood of the animals in normal group, model group, Tirzepatide—0.15 mg/kg group, BG128—0.05 mg/kg group, BG128—0.15 mg/kg group and BG128—0.5 mg/kg group.
Figure 22:
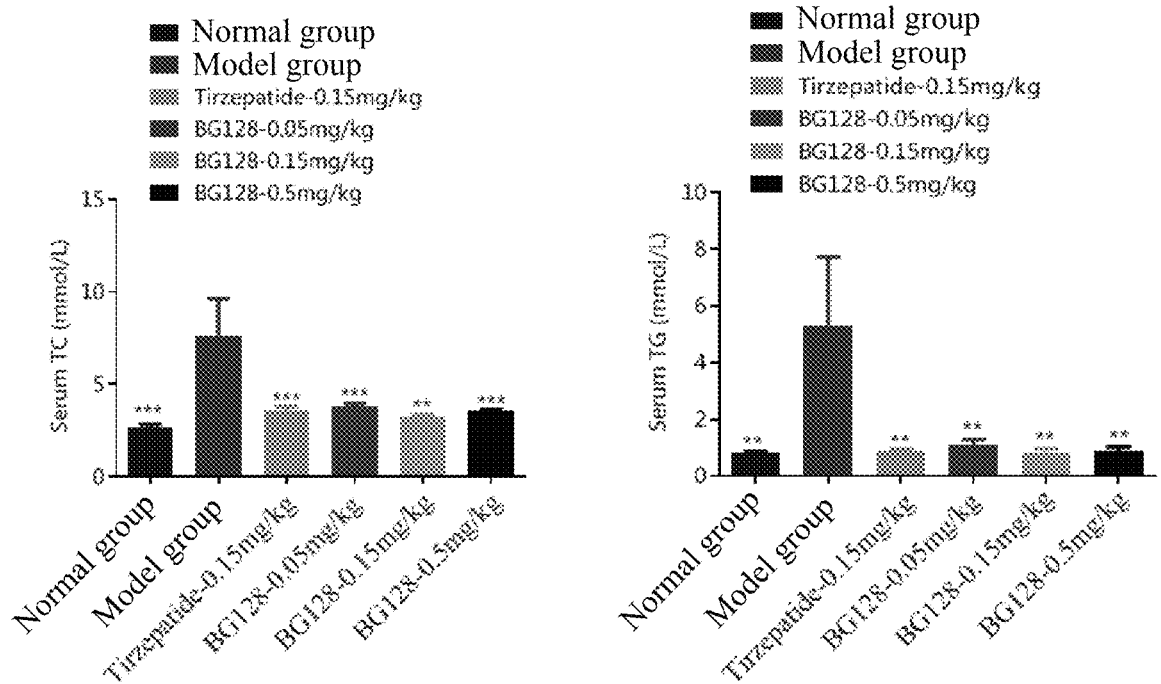
FIG. 22 shows the changes in the TC and TG in the blood of the animals in normal group, model group, Tirzepatide—0.15 mg/kg group, BG128—0.05 mg/kg group, BG128—0.15 mg/kg group and BG128—0.5 mg/kg group.
Figure 23:
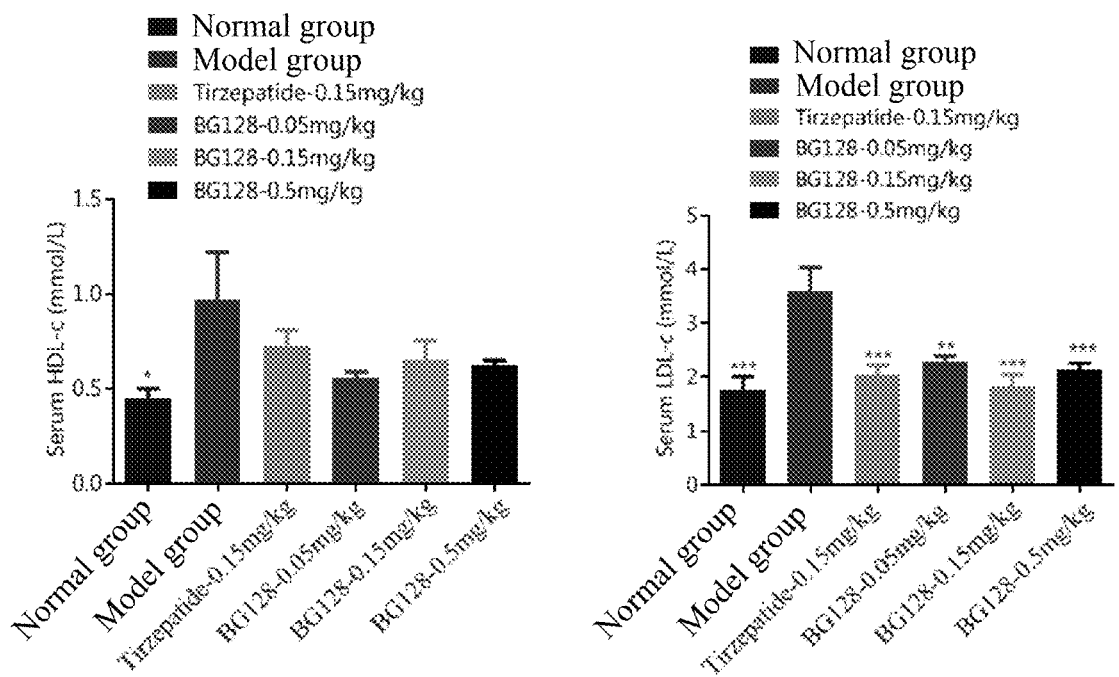
FIG. 23 shows the changes in the high and low density lipoprotein in the blood of the animals in normal group, model group, Tirzepatide—0.15 mg/kg group, BG128—0.05 mg/kg group, BG128—0.15 mg/kg group and BG128—0.5 mg/kg group.

$^a$*p < 0.05 vs. model group, by One way-ANOVA, Tukey's test 4.7 Liver Function and Blood Lipid-Related Biochemical Indicators The results of liver function and blood lipid-related biochemical indicators showed (Table 18 and FIGS. 21-23): compared with the model group, the ALT and AST of the Tirzepatide—0.15 mg/kg group and each dose group of BG128 were all decreased, and there was a significant difference between the decrease of the BG128—0.15 mg/kg group and the decrease of the 0.5 mg/kg dose group (FIG. 21); the total cholesterol and triglyceride of the Tirzepatide—0.15 mg/kg group and each dose group of BG128 were significantly decreased (FIG. 22); and the low-density lipoprotein of the Tirzepatide—0.15 mg/kg group and each dose group of BG128 was significantly decreased, while the high-density lipoprotein had no significant change (FIG. 23). The effect of the BG128 group was better than that of the Tirzepatide group at an equal dose.

TABLE 18

Clinical biochemical determination results (Mean ± SEM)

| Group | Normal control group | Model group | Tirzepatide 0.15 mg/kg | BG128 0.05 mg/kg | BG128 0.15 mg/kg | BG128 0.5 mg/kg |
|---|---|---|---|---|---|---|
| Number | n = 10 | n = 9 | n = 13 | n = 11 | n = 13 | n = 13 |
| ALT (U/L) | 62.08 ± 4.56$^a$ | 104.67 ± 7.22 | 79.23 ± 10.51 | 73.97 ± 9.20 | 67.58 ± 7.73$^a$ | 58.46 ± 5.38$^b$ |
| AST (U/L) | 89.55 ± 4.70$^c$ | 185.44 ± 14.85 | 158.77 ± 11.64 | 155.44 ± 10.85 | 152.48 ± 6.56$^a$ | 150.54 ± 6.26$^a$ |
| TC (mmol/L) | 2.68 ± 0.16$^c$ | 7.64 ± 1.98 | 3.58 ± 0.21$^c$ | 3.81 ± 0.15$^c$ | 3.25 ± 0.12$^c$ | 3.53 ± 0.09$^c$ |
| TG (mmol/L) | 0.83 ± 0.02$^b$ | 5.33 ± 2.39 | 0.86 ± 0.08$^b$ | 1.09 ± 0.20$^b$ | 0.84 ± 0.12$^b$ | 0.88 ± 0.14$^b$ |
| HDL-c (mmol/L) | 1.76 ± 0.25$^a$ | 3.59 ± 0.45 | 2.04 ± 0.19 | 2.30 ± 0.09 | 1.83 ± 0.22 | 2.13 ± 0.13 |
| LDL-c (mmol/L) | 0.45 ± 0.05$^c$ | 0.97 ± 0.25 | 0.73 ± 0.09$^c$ | 0.56 ± 0.03$^b$ | 0.65 ± 0.10$^c$ | 0.62 ± 0.03$^c$ |

Figure 24:
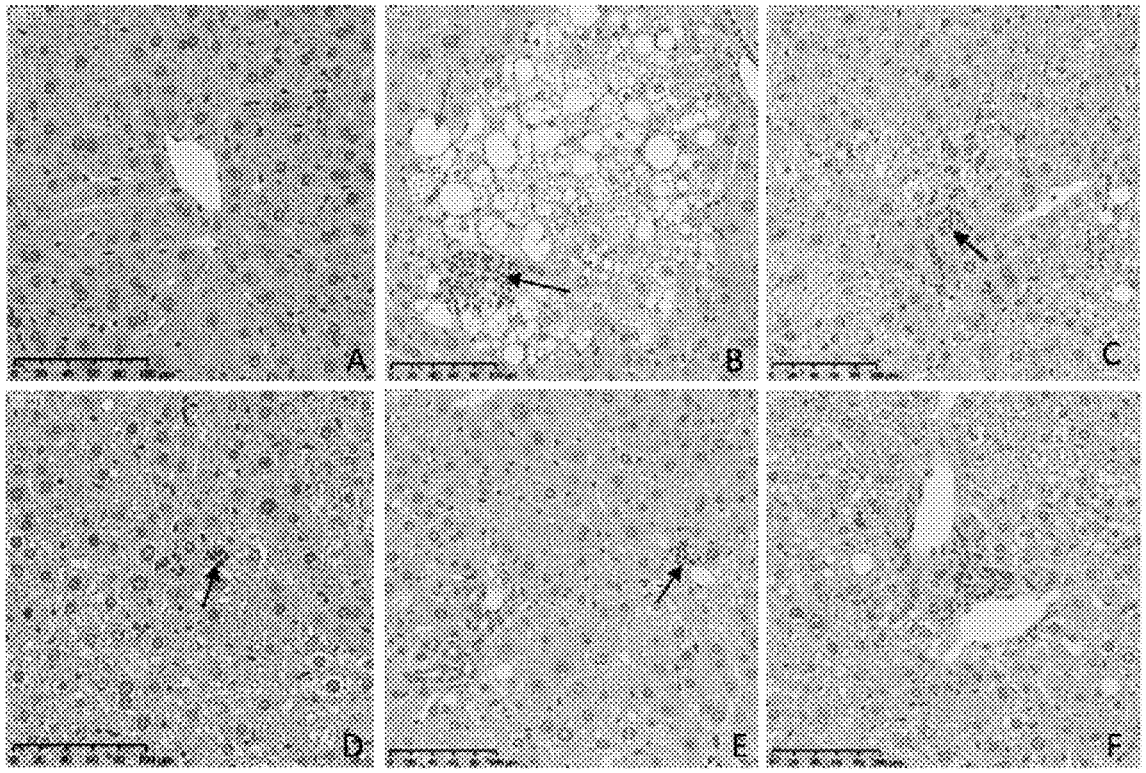
FIG. 24 shows the HE stained pictures (×400) of the liver tissues of the animals in normal group, model group, Tirzepatide—0.15 mg/kg group, BG128—0.05 mg/kg group, BG128—0.15 mg/kg group and BG128—0.5 mg/kg group; A: normal control group; B: model group; C: Tirzepatide—0.15 mg/kg; D: BG128—0.05 mg/kg; E: BG128—0.15 mg/kg; F: BG128—0.5 mg/kg.

$^a$*p < 0.05 vs. model group, by One-way ANOVA, Tukey's test
$^b$**p < 0.01 vs. model group, by One-way ANOVA, Tukey's test
$^c$***p < 0.001 vs. model group, by One-way ANOVA, Tukey's test
$^{d\&\&}$p < 0.01 vs. model group; e: $^{\&\&\&}$p < 0.01 vs. model group, by T-test 4.8 Liver Histopathology
4.8.1 NAS Evaluation The liver pathological changes were assessed using H&E staining. The hepatic steatosis in the model group showed hepatic vacuolar degeneration, which were widely distributed in the liver lobes; the hepatic interlobular inflammation showed scattered focal inflammatory cell infiltration in the hepatic lobules; and no ballooning lesion was observed (Table 19 and FIG. 24). In FIG. 24, A: normal control group; B: model group; C: Tirzepatide—0.15 mg/kg; D: BG128—0.05 mg/kg; E: BG128—0.15 mg/kg; F: BG128—0.5 mg/kg. It can be seen from FIG. A that hepatocytes were neatly arranged and the cell structure was complete, hepatic steatosis (yellow arrow) and inflammatory cell infiltration (black arrow) can be seen from FIG. B, and different degrees of inflammatory cell infiltration and reduction of hepatic steatosis can be seen from FIGS. C, D, E, and F.

According to the NAS scoring standard listed in Table 14, the hepatic steatosis, hepatic interlobular inflammation and NAS score of the model group were significantly higher than those of the normal group (P<0.001).

Figure 25:
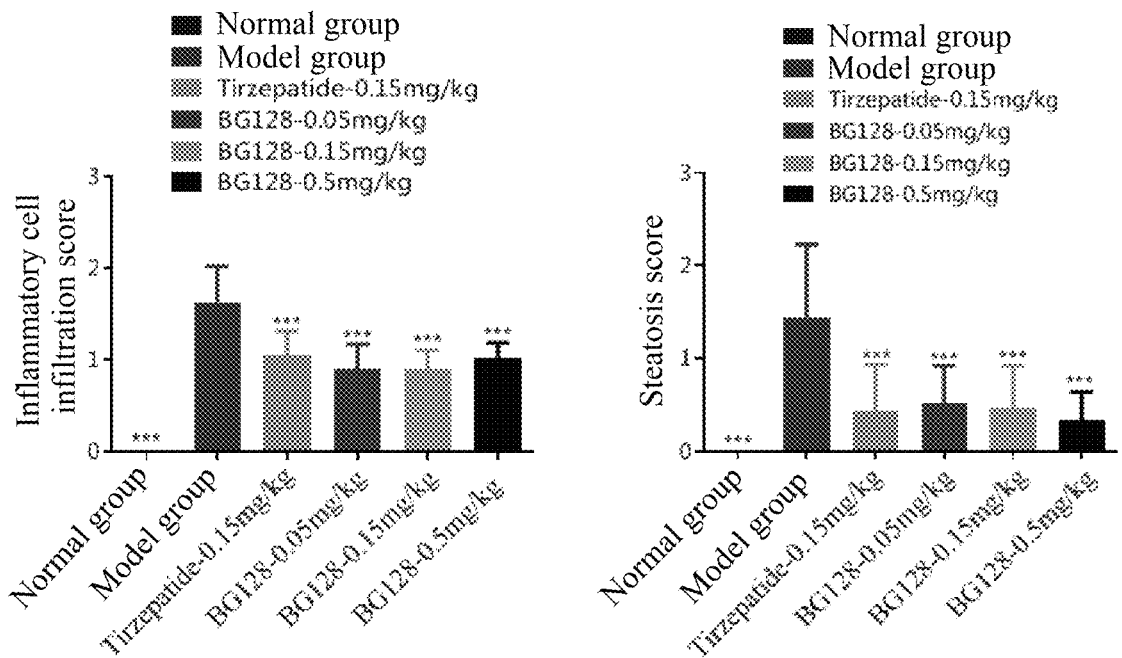
FIG. 25 shows the changes in inflammatory cell infiltration and steatosis of the animals in normal group, model group, Tirzepatide—0.15 mg/kg group, BG128—0.05 mg/kg group, BG128—0.15 mg/kg group and BG128—0.5 mg/kg group.

Compared with the model group, the Tirzepatide—0.15 mg/kg group and each dose group of BG128 have significantly reduced liver inflammatory cell infiltration and hepatic steatosis scores (FIG. 25).

Figure 26:
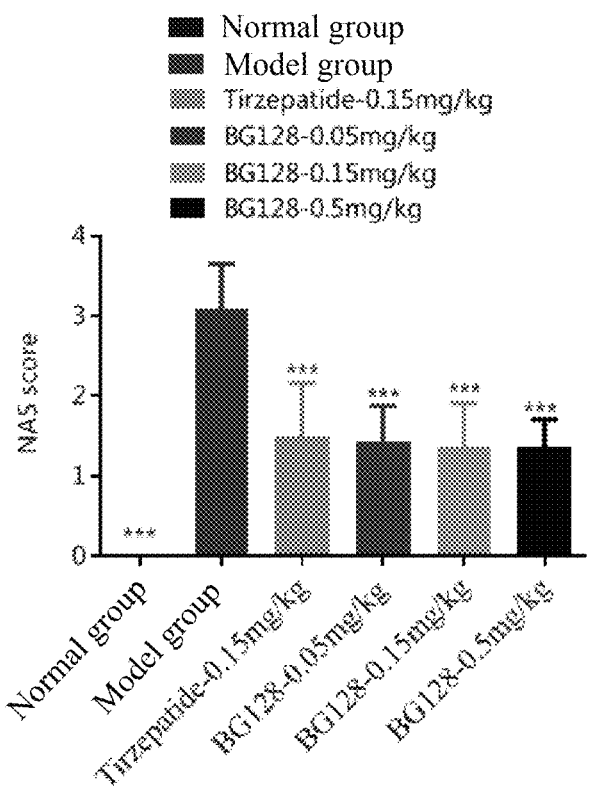
FIG. 26 shows the NAS scoring results of the animals in normal group, model group, Tirzepatide—0.15 mg/kg group, BG128—0.05 mg/kg group, BG128—0.15 mg/kg group and BG128—0.5 mg/kg group.

Compared with the model group, the Tirzepatide—0.15 mg/kg group and each dose group of BG128 have significantly reduced total score of NAS (p<0.001) (FIG. 26).

TABLE 19

Histopathological results (Mean ± SEM)

| Group | Number | Steatosis | Inflammatory cell infiltration | Ballooning lesion | Total score of NAS |
|---|---|---|---|---|---|
| Normal control group | 10 | 0.00 ± 0.00$^a$ | 0.00 ± 0.00$^a$ | 0.00 ± 0.00 | 0.00 ± 0.00$^a$ |
| Model group | 9 | 1.44 ± 0.26 | 1.63 ± 0.13 | 0.00 ± 0.00 | 3.07 ± 0.19 |
| Tirzepatide-0.15 mg/kg | 13 | 0.44 ± 0.14$^a$ | 1.05 ± 0.07$^a$ | 0.00 ± 0.00 | 1.49 ± 0.19$^a$ |
| BG128-0.05 mg/kg | 11 | 0.52 ± 0.12$^a$ | 0.91 ± 0.08$^a$ | 0.00 ± 0.00 | 1.42 ± 0.14$^a$ |
| BG128-0.15 mg/kg | 13 | 0.46 ± 0.13$^a$ | 0.90 ± 0.06$^a$ | 0.00 ± 0.00$^a$ | 1.36 ± 0.15$^a$ |
| BG128-0.5 mg/kg | 13 | 0.33 ± 0.08$^a$ | 1.03 ± 0.05$^a$ | 0.00 ± 0.00 | 1.36 ± 0.10$^a$ |

$^a$***p < 0.001 vs. model group, by One-way ANOVA, Tukey's test

4.8.2 Liver Fibrosis Evaluation

Figure 27:
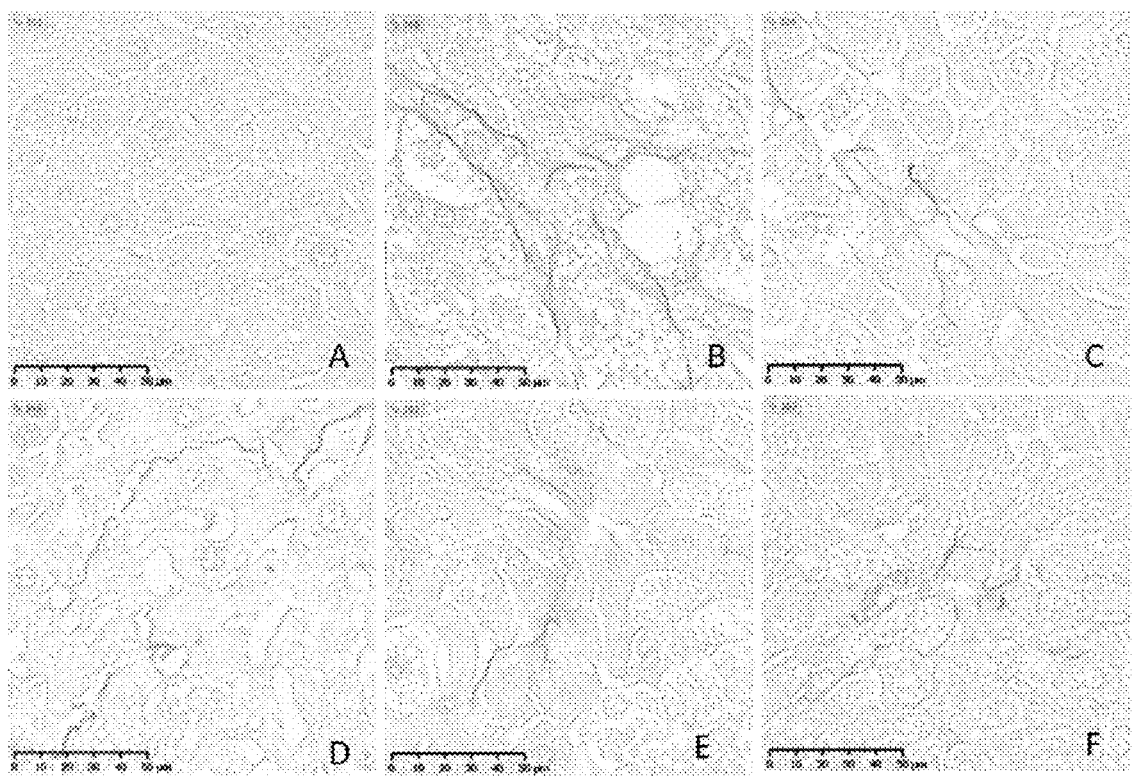
FIG. 27 shows the sirius red stained pictures (×200) of the liver tissues of the animals in normal group, model group, Tirzepatide—0.15 mg/kg group, BG128—0.05 mg/kg group, BG128—0.15 mg/kg group and BG128—0.5 mg/kg group; A: normal control group; B: model group; C: Tirzepatide—0.15 mg/kg; D: BG128—0.05 mg/kg; E: BG128—0.15 mg/kg; F: BG128—0.5 mg/kg.

Sirius red staining showed that the fibrosis was mainly distributed in the portal vein, central vein and intercellular region (FIG. 27). In FIG. 27, A: normal control group; B: model group; C: Tirzepatide—0.15 mg/kg; D: BG128—0.05 mg/kg; E: BG128—0.15 mg/kg; F: BG128—0.5 mg/kg. It can be seen from FIG. A that there is no fibrosis formation between the hepatic cell cords, and it can be seen from FIGS. B, C, D, E and F there are red fibers formed between the hepatic cell cords.

Figure 28:
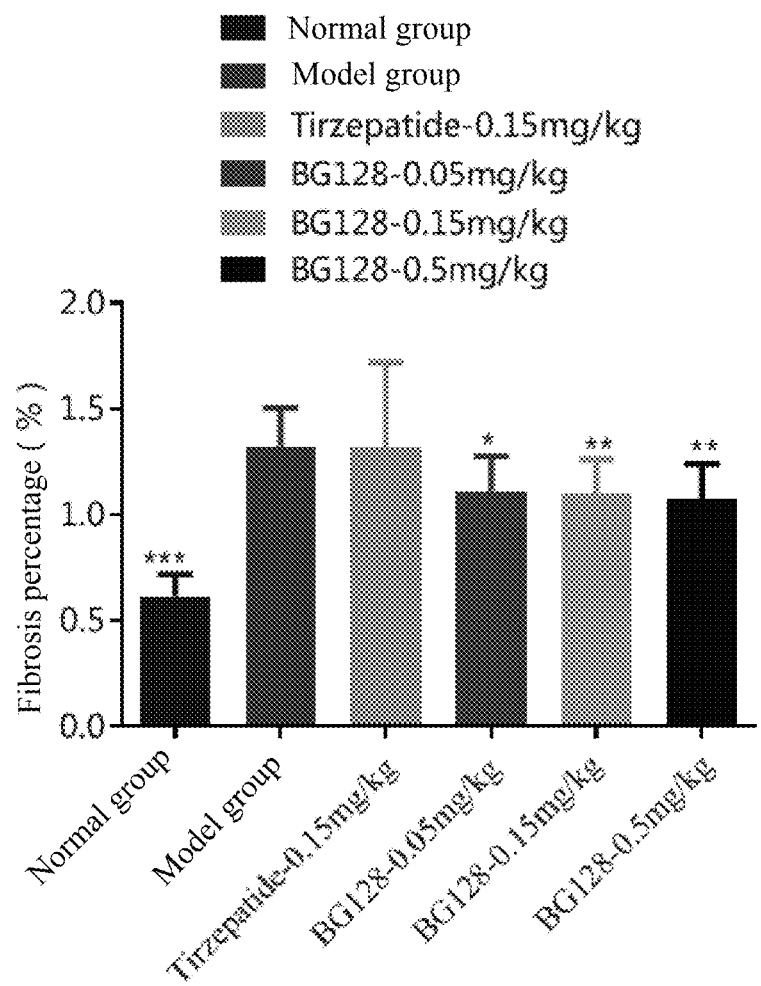
FIG. 28 shows the fibrosis percentages of the liver tissues of the animals in normal group, model group, Tirzepatide—0.15 mg/kg group, BG128—0.05 mg/kg group, BG128—0.15 mg/kg group and BG128—0.5 mg/kg group.

Semi-quantitative analysis of liver fibrosis showed (Table 20) that the fibrosis rate of the model group was 1.32±0.02%, which was significantly higher than that of the normal control group (p<0.001). The fibrosis rate of each dose group of BG128 was significantly reduced compared with that of the model group (Table 20 and FIG. 28).

TABLE 20

Fibrosis percentage (Mean ± SEM)

| Group | Normal control group | Model group | Tirzepatide 0.15 mg/kg | BG128 0.05 mg/kg | BG128 0.15 mg/kg | BG128 0.5 mg/kg |
|---|---|---|---|---|---|---|
| Number | n=10 | n = 9 | n = 13 | n = 11 | n = 13 | n = 13 |
| Fibrosis (%) | 0.61 ± 0.03$^c$ | 1.32 ± 0.06 | 1.32 ± 0.11 | 1.11 ± 0.05$^a$ | 1.10 ± 0.04$^b$ | 1.07 ± 0.05$^c$ |

$^a$*p < 0.05 vs. model group, by T-test
$^b$**p < 0.01 vs. model group, by T-test
$^c$***p < 0.001 vs. model group, by T-test

5. Conclusion

In the experiment, the male C57 BL/6 mouse model with STZ-HFD feed-induced diabetes combined NASH was used. In the model group, the fasting blood glucose and HbA1c % were increased significantly, the serum biochemical indicators related to liver function and blood lipids were increased significantly, and the liver histopathological indicators changed significantly, including hepatic steatosis, increased hepatic interlobular inflammation, elevated NAS score, and exacerbated liver fibrosis. The symptoms were similar to clinical features of hyperglycemia and NASH in humans, indicating that the model is stable and reliable.

BG128 has obvious therapeutic effect on C57BL/6 model having STZ-HFD-induced diabetes combined NASH, and each dose group of BG128 can significantly reduce the fasting blood glucose, insulin and HbA1c %, and has a certain protective effect on the model animals in a dose dependent manner. BG128 can significantly improve liver function and blood lipid-related clinical biochemical indicators, reduces liver NAS score and fibrosis rate, and significantly delays the progress of NASH and fibrosis process. Overall, the efficacy of BG128 is better than that of the control drug Tirzepatide group at an equal dose.

All technical features disclosed in the specification can be combined in any combination. Each feature disclosed in the specification can also be replaced with other features having the same, equivalent or similar effect. Therefore, unless specially indicated, each feature disclosed is only an example of a series of equivalent or similar features.

In addition, according the above-mentioned description, a person skilled in the art can easily understand the key features of the present disclosure from the present disclosure. Many modifications can be made to the present invention to adapt to various purposes and conditions of use without departing from the spirit and scope of the present disclosure, and therefore such modifications are also intended to fall within the scope of the appended claims.

What is claimed is:

1. A compound represented by any one of the following formulas I-3 or I-4 or a pharmaceutically acceptable salt, ester, optical isomer, tautomer, isotopically labeled compound or prodrug thereof:

(SEQ ID NO: 5)

I-3

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser

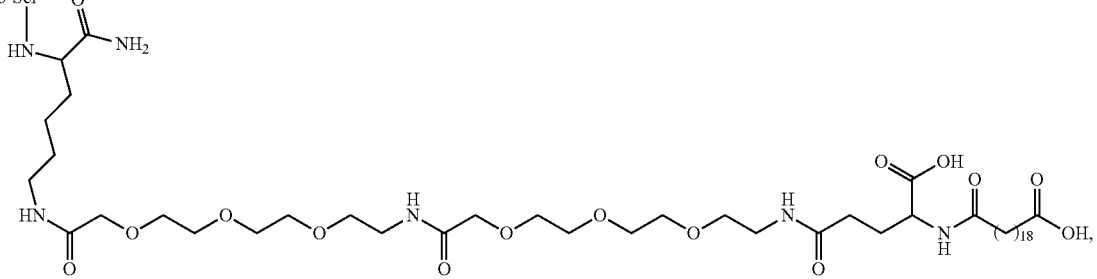

or (SEQ ID NO: 6)

I-4

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser

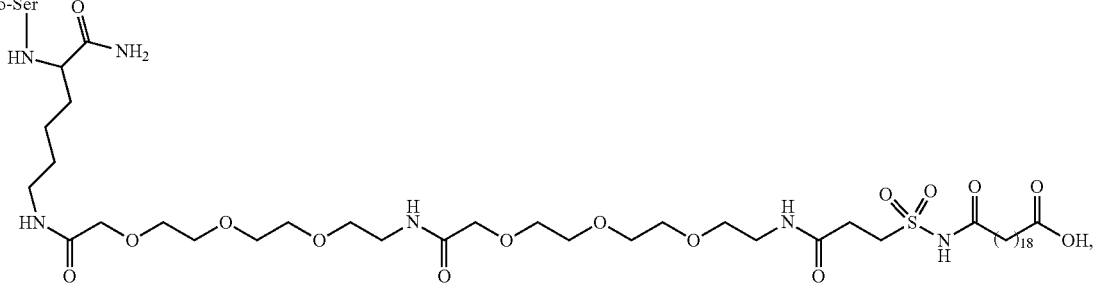

2. A GIP and GLP-1 dual receptor agonist, wherein, the GIP and GLP-1 dual receptor agonist is a compound represented by formula I-3 or a pharmaceutically acceptable salt, ester, optical isomer, tautomer, isotopically labeled compound or prodrug thereof:

I-3 (SEQ ID NO: 5)

Tyr-Aib-Glu-Gly-Thr-Phe-Thr-Ser-Asp-Tyr-Ser-Ile-Aib-Leu-Asp-Lys-Ile-Ala-Gln-Lys-Ala-Phe-Val-Gln-Trp-Leu-Ile-Ala-Gly-Gly-Pro-Ser-Ser-Gly-Ala-Pro-Pro-Pro-Ser

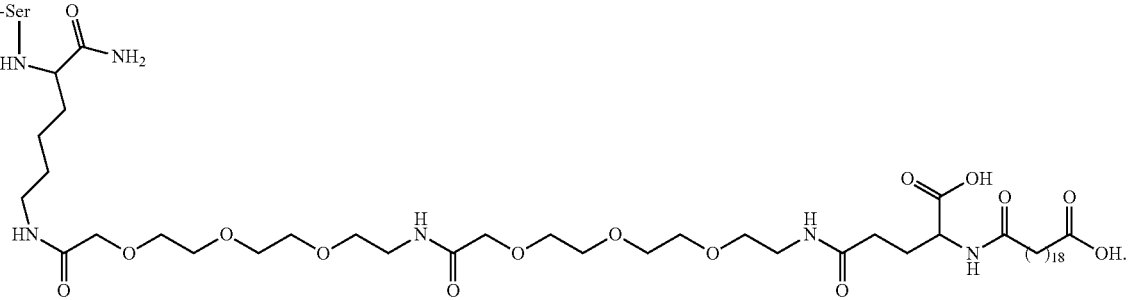

3. A pharmaceutical composition comprising the compound or the pharmaceutically acceptable salt, ester, optical isomer, tautomer, isotopically labeled compound or prodrug thereof according to claim 1; wherein the pharmaceutical composition further comprises one or more pharmaceutically acceptable carriers.

4. A method for preventing and/or treating diseases associated with metabolic disorders, comprising administering a prophylactically and/or therapeutically effective amount of the compound or the pharmaceutically acceptable salt, ester, optical isomer, tautomer, isotopically labeled compound or prodrug thereof according to claim 1 to a subject; wherein the diseases associated with metabolic disorders are diabetes or obesity.

5. A pharmaceutical composition comprising the GIP and GLP-1 dual receptor agonist according to claim 2; wherein the pharmaceutical composition further comprises one or more pharmaceutically acceptable carriers.

6. A method for preventing and/or treating diseases associated with metabolic disorders, comprising administering a prophylactically and/or therapeutically effective amount of the GIP and GLP-1 dual receptor agonist according to claim 2 to a subject; wherein
the diseases associated with metabolic disorders are diabetes or obesity.

7. A method for preventing and/or treating diseases associated with metabolic disorders, comprising administering a prophylactically and/or therapeutically effective amount of the pharmaceutical composition according to claim 3 to a subject; wherein
the diseases associated with metabolic disorders are diabetes or obesity.

8. A method for preventing and/or treating diseases associated with metabolic disorders, comprising administering a prophylactically and/or therapeutically effective amount of the pharmaceutical composition according to claim 5 to a subject; wherein
the diseases associated with metabolic disorders are diabetes or obesity.

* * * * *